United States Patent
Iida et al.

(10) Patent No.: US 11,261,249 B2
(45) Date of Patent: Mar. 1, 2022

(54) ANTI-GPR20 ANTIBODY

(71) Applicant: DAIICHI SANKYO COMPANY, LIMITED, Tokyo (JP)

(72) Inventors: Kenji Iida, Tokyo (JP); Tomoko Shibutani, Tokyo (JP); Kensuke Nakamura, Tokyo (JP); Masato Amano, Tokyo (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 195 days.

(21) Appl. No.: 16/490,472

(22) PCT Filed: Mar. 29, 2018

(86) PCT No.: PCT/JP2018/013106
§ 371 (c)(1),
(2) Date: Aug. 30, 2019

(87) PCT Pub. No.: WO2018/181656
PCT Pub. Date: Oct. 4, 2018

(65) Prior Publication Data
US 2020/0017583 A1 Jan. 16, 2020

(30) Foreign Application Priority Data
Mar. 30, 2017 (JP) .............................. 2017-067164

(51) Int. Cl.
| | |
|---|---|
| G01N 33/53 | (2006.01) |
| C07K 16/00 | (2006.01) |
| C07K 16/46 | (2006.01) |
| C07K 16/28 | (2006.01) |
| C12N 5/16 | (2006.01) |
| C12N 15/85 | (2006.01) |
| G01N 33/574 | (2006.01) |
| G01N 33/577 | (2006.01) |

(52) U.S. Cl.
CPC ............... *C07K 16/28* (2013.01); *C12N 5/16* (2013.01); *C12N 15/85* (2013.01); *G01N 33/577* (2013.01); *G01N 33/57446* (2013.01); *C07K 2317/24* (2013.01); *C07K 2317/34* (2013.01); *C07K 2317/622* (2013.01); *C07K 2317/76* (2013.01); *G01N 2333/705* (2013.01); *G01N 2800/06* (2013.01)

(58) Field of Classification Search
None
See application file for complete search history.

(56) References Cited

U.S. PATENT DOCUMENTS 10,906,974 B2 * 2/2021 Iida .................... A61K 47/64
2003/0018989 A1 1/2003 Brennan et al.

FOREIGN PATENT DOCUMENTS

| JP | 2004-321184 A | 11/2004 |
|---|---|---|
| WO | WO-02/061087 A2 | 8/2002 |
| WO | WO-2005/040825 A2 | 5/2005 |
| WO | WO-2008/138536 A2 | 11/2008 |
| WO | WO-2018/135501 A1 | 7/2018 |

OTHER PUBLICATIONS

Edwards et al., The remarkable flexibility of the human antibody repertoire; isolation of over one thousand different antibodies to a single protein, BLyS. J Mol Biol. Nov. 14, 2003;334(1): 103-18. (Year: 2003).*
Lloyd et al., Modelling the human immune response: performance of a 1011 human antibody repertoire against a broad panel of therapeutically relevant antigens. Protein Eng Des Sel. Mar. 2009;22(3):159-68. (Year: 2009).*
Goel et al., Plasticity within the antigen-combining site may manifest as molecular mimicry in the humoral immune response. J Immunol. Dec. 15, 2004; 173(12):7358-67. (Year: 2004).*
Kanyavuz et al., Breaking the law: unconventional strategies for antibody diversification. Nat Rev Immunol. Jun. 2019; 19(6):355-368. (Year: 2019).*
Lida et al. Identification and Therapeutic Targeting of GPR20, Selectively Expressed in Gastrointestinal Stromal Tumors, with DS-6157a, a First-in-Class Antibody-Drug Conjugate. Cancer Discov Jun. 2021;11(6):1508-1523. (Year: 2021).*
Lida et al. Therapeutic targeting of GPR20, selectively expressed in gastrointestinal stromal tumor (GIST), with DS-6157a, an antibody-drug conjugate (ADC). Abstract 5181: Cancer Res Aug. 15, 2020 (80) (16 Supplement) 5181. (Year: 2020).*
Hase et al., "Characterization of an Orphan G Protein-coupled Receptor, GPR20, That Constitutively Activates G, Proteins," Journal of Biological Chemistry, vol. 283, No. 19, May 9, 2008, pp. 12747-12755.
O'Dowd et al., "Cloning and chromosomal mapping of four putative novel human G-protein-coupled receptor genes," Gene. vol. 187, 1997, pp. 75-81.
Allander et al., "Gastrointestinal Stromal Tumors with *KIT* Mutations Exhibit a Remarkably Homogeneous Gene Expression Profile," Cancer Research, vol. 61, pp. 8624-8628, Dec. 15, 2001.
Chi et al., "ETV1 is a lineage survival factor that cooperates with KIT in gastrointestinal stromal tumours," Nature, vol. 467, Oct. 14, 2010, pp. 849-855.

(Continued)

*Primary Examiner* — Maher M Haddad
(74) *Attorney, Agent, or Firm* — Foley & Lardner LLP

(57) ABSTRACT

It is an object of the present invention to provide an anti-GPR20 antibody that can be used in the detection of GPR20, a reagent for GPR20 detection comprising the antibody, a reagent for diagnosis or a composition for testing of a disease related to the expression of GPR20, etc. The present invention provides an antibody specifically binding to a peptide comprising the amino acid sequence at amino acid positions 1 to 48 in SEQ ID NO: 1, or an antigen-binding fragment of the antibody, a chimeric antibody of the antibody, a rabbit type antibody of the antibody, etc. The present invention also provides a composition comprising the antibody, etc.

17 Claims, 17 Drawing Sheets
Specification includes a Sequence Listing.

(56) References Cited

OTHER PUBLICATIONS

International Searching Authority, "International Search Report," issued in connection with International Patent Application No. PCT/JP2018/013106, dated Jun. 26, 2018.
International Searching Authority, "Written Opinion," issued in connection with International Patent Application No. PCT/JP2018/013106, dated Jun. 26, 2018.
Extended European Search Report dated Nov. 5, 2020 for corresponding European Patent Application No. 18776022.8.

* cited by examiner

[Figure 1]

SEQ ID NO 3: Amino acid sequence of 04-093 antibody heavy chain
MDIRLSLVFLVLFIKGVQCEVQLVESGGGLVQPGRSLKLSCVASGFTFNNYWMTWIRQAPGKGL
EWVASITNIDGSSYYPDSVKGRFTISRDNVKSTLYLQMNSLRSEDTATYYCTRGSFDYWGQGVM
VTVSSAQTTAPSVYPLAPGCGDTTSSTVTLGCLVKGYFPEPVTVTWNSGALSSDVHTFPAVLQS
GLYTLTSSVTSSTWPSQTVTCNVAHPASSTKVDKKVERRNGGIGHKCPTCPTCHKCPVPELLGG
PSVFIFPPKPKDILLISQNAKVTCVVVDVSEEEPDVQFSWFVNNVEVHTAQTQPREEQYNSTFR
VVSALPIQHQDWMSGKEFKCKVNNKALPSPIEKTISKPKGLVRKPQVYVMGPPTEQLTEQTVSL
TCLTSGFLPNDIGVEWTSNGHIEKNYKNTEPVMDSDGSFFMYSKLNVERSRWDSRAPFVCSVVH
EGLHNHHVEKSISRPPGK
Signal sequence (1-19), heavy chain variable region (20-133),
heavy chain constant region (134-466)
CDRH1 (45-54), CDRH2 (69-78), CDRH3 (118-122)

SEQ ID NO 2: Nucleotide sequence of 04-093 antibody heavy chain
ATGGACATCAGGCTCAGCTTGGTTTTCCTTGTCCTTTTCATAAAAGGTGTCCAGTGTGAGGTGC
AGCTGGTGGAGTCTGGGGGAGGCCTAGTGCAGCCTGGAAGGTCTCTGAAACTATCCTGTGTAGC
CTCTGGATTCACATTCAACAACTACTGGATGACCTGGATCCGCCAGGCTCCAGGGAAGGGGCTG
GAGTGGGTTGCATCCATTACTAATATTGATGGTAGCAGTTACTATCCAGACTCTGTGAAGGGCC
GATTCACTATCTCCAGAGATAATGTAAAAAGCACCCTATACCTGCAAATGAACAGTCTGAGGTC
TGAGGACACGGCCACTTATTACTGTACAAGAGGATCCTTTGATTACTGGGGCCAAGGAGTCATG
GTCACAGTCTCCTCAGCCCAAACAACAGCCCCATCTGTCTATCCACTGGCTCCTGGATGTGGTG
ATACAACCAGCTCCACGGTGACTCTGGGATGCCTGGTCAAGGGCTATTTCCTGAGCCAGTCAC
CGTGACCTGGAACTCTGGAGCCCTGTCCAGCGATGTGCACACCTTTCCAGCTGTCCTGCAGTCT
GGGCTCTACACTCTCACCAGCTCAGTGACCTCCAGCACCTGGCCCAGCCAGACCGTCACCTGCA
ACGTAGCCCACCCGGCCAGCAGCACCAAGGTGGACAAGAAAGTTGAGCGCAGAAATGGCGGCAT
TGGACACAAATGCCCTACATGCCCTACATGTCACAAATGCCCAGTTCCTGAACTCTTGGGTGGA
CCATCTGTCTTCATCTTCCCGCCAAAGCCCAAGGACATCCTCTTGATCTCCCAGAACGCCAAGG
TCACGTGTGTGGTGGTGGATGTGAGCGAGGAGGAGCCGGACGTCCAGTTCAGCTGGTTTGTGAA
CAACGTAGAAGTACACACAGCTCAGACACAACCCCGTGAGGAGCAGTACAACAGCACCTTCAGA
GTGGTCAGTGCCCTCCCCATCCAGCACCAGGACTGGATGAGCGGCAAGGAGTTCAAATGCAAGG
TCAACAACAAAGCCCTCCCAAGCCCCATCGAGAAACCATCTCAAAACCCAAAGGGCTAGTCAG
AAAACCACAGGTATACGTCATGGGTCCACCGACAGAGCAGTTGACTGAGCAAACGGTCAGTTTG
ACCTGCTTGACCTCAGGCTTCCTCCCTAACGACATCGGTGTGGAGTGGACCAGCAACGGGCATA
TAGAAAAGAACTACAAGAACACCGAGCCAGTGATGGACTCTGACGGTTCTTTCTTCATGTACAG
CAAGCTCAATGTGGAAAGGAGCAGGTGGGATAGCAGAGCGCCCTTCGTCTGCTCCGTGGTCCAC
GAGGGTCTGCACAATCACCACGTGGAGAAGAGCATCTCCCGGCCTCCGGGTAAA
Signal sequence (1-57), heavy chain variable region (58-399),
heavy chain constant region (400-1398)
CDRH1 (133-162), CDRH2 (205-234), CDRH3 (352-366)

[Figure 2]

SEQ ID NO 11: Amino acid sequence of 04-093 antibody light chain
MAPVQLLGLLLLWLPAMRCDIQMTQSPSVLSASVGDRVTLNCKASQNVNKYLNWFQQKLGEPPK
LLIYNTNNLQTGIPSRFSGSGSGTDYTLTISSLQPEDVATYFCFQHVSWLTFGSGTKLEIKRAD
AAPTVSIFPPSTEQLATGGASVVCLMNNFYPRDISVKWKIDGTERRDGVLDSVTDQDSKDSTYS
MSSTLSLTKADYESHNLYTCEVVHKTSSSPVVKSFNRNEC
Signal sequence (1-19), light chain variable region (20-126),
light chain constant region (127-232)
CDRL1 (43-53), CDRL2 (69-75), CDRL3 (108-115)

SEQ ID NO 10: Nucleotide sequence of 04-093 antibody light chain
ATGGCTCCAGTTCAACTCTTAGGGCTGCTGCTGCTCTGGCTCCCAGCCATGAGATGTGACATCC
AGATGACCCAGTCTCCTTCAGTCCTCTCTGCATCTGTGGGAGACAGAGTCACTCTCAACTGCAA
AGCAAGTCAGAATGTTAACAAGTACTTAAACTGGTTTCAGCAAAAGCTTGGAGAACCTCCCAAA
CTCCTGATATATAATACAAACAATTTGCAAACGGGCATCCCATCAAGGTTCAGTGGCAGTGGAT
CTGGTACAGATTACACACTCACCATCAGCAGCCTGCAGCCTGAAGATGTTGCCACATATTTCTG
CTTTCAGCATGTTAGTTGGCTCACGTTCGGTTCTGGGACCAAGCTGGAGATCAAACGGGCTGAT
GCTGCACCAACTGTATCTATCTTCCCACCATCCACGGAACAGTTAGCAACTGGAGGTGCCTCAG
TCGTGTGCCTCATGAACAACTTCTATCCCAGAGACATCAGTGTCAAGTGGAAGATTGATGGCAC
TGAACGACGAGATGGTGTCCTGGACAGTGTTACTGATCAGGACAGCAAAGACAGCACGTACAGC
ATGAGCAGCACCCTCTCGTTGACCAAGGCTGACTATGAAAGTCATAACCTCTATACCTGTGAGG
TTGTTCATAAGACATCATCCTCACCCGTCGTCAAGAGCTTCAACAGGAATGAGTGT
Signal sequence (1-57), light chain variable region (58-378),
light chain constant region (379-696)
CDRL1 (127-159), CDRL2 (205-225), CDRL3 (322-345)

[Figure 3]

Amino acid sequences of CDRs of rat anti-GPR20 antibody 04-093

| | | | |
|---|---|---|---|
| CDRH1(abm) | : GFTFNNYWMT | (SEQ ID NO: | 5) |
| CDRH2(abm) | : SITNIDGSSY | (SEQ ID NO: | 6) |
| CDRH3 | : GSFDY | (SEQ ID NO: | 7) |
| CDRH1(kabat) | : NYWMT | (SEQ ID NO: | 8) |
| CDRH2(kabat) | : SITNIDGSSYYPDSVKG | (SEQ ID NO: | 9) |
| CDRL1 | : KASQNVNKYLN | (SEQ ID NO: | 13) |
| CDRL2 | : NTNNLQT | (SEQ ID NO: | 14) |
| CDRL3 | : FQHVSWLT | (SEQ ID NO: | 15) |

[Figure 4]

SEQ ID NO 19: Amino acid sequence of rabbit chimeric antibody heavy chain OcHch

MKHLWFFLLLVAAPRWVLSEVQLVESGGGLVQPGRSLKLSCVASGFTFNNYWMTWIRQAPGKGL
EWVASITNIDGSSYYPDSVKGRFTISRDNVKSTLYLQMNSLRSEDTATYYCTRGSFDYWGQGVM
VTVSSGQPKAPSVFPLAPCCGDTPSSTVTLGCLVKGYLPEPVTVTWNSGTLTNGVRTFPSVRQS
SGLYSLSSVVSVTSSSQPVTCNVAHPATNTKVDKTVAPSTCSKPTCPPPELLGGPSVFIFPPKP
KDTLMISRTPEVTCVVVDVSQDDPEVQFTWYINNEQVRTARPPLREQQFNSTIRVVSTLPITHQ
DWLRGKEFKCKVHNKALPAPIEKTISKARGQPLEPKVYTMGPPREELSSRSVSLTCMINGFYPS
DISVEWEKNGKAEDNYKTTPAVLDSDGSYFLYNKLSVPTSEWQRGDVFTCSVMHEALHNHYTQK
SISRSPGK

Signal sequence (1-19), heavy chain variable region (20-133),
heavy chain constant region (134-456)

[Figure 5]

SEQ ID NO 21: Amino acid sequence of rabbit chimeric antibody light chain OcLch

MVLQTQVFISLLLWISGAYGDIQMTQSPSVLSASVGDRVTLNCKASQNVNKYLNWFQQKLGEPP
KLLIYNTNNLQTGIPSRFSGSGSGTDYTLTISSLQPEDVATYFCFQHVSWLTFGSGTKLEIKRD
PVAPSVLLFPPSKEELTTGTATIVCVANKFYPSDITVTWKVDGTTQQSGIENSKTPQSPEDNTY
SLSSTLSLTSAQYNSHSVYTCEVVQGSASPIVQSFNRGDC

Signal sequence (1-20), light chain variable region (21-127),
light chain constant region (128-232)

[Figure 6]

SEQ ID NO 23: Amino acid sequence of rabbit type antibody heavy chain OcH01

MKHLWFFLLLVAAPRWVLSEVQLKESGGGLVKPGGSLKLCCKASGFTFNNYWMTWIRQAPGKGL
EWIASITNIDGSSYYASWVNGRFTLSRDNAQSTVCLQLNSLTAADTATYFCTRGSFDYWGQGTL
VTVSSGQPKAPSVFPLAPCCGDTPSSTVTLGCLVKGYLPEPVTVTWNSGTLTNGVRTFPSVRQS
SGLYSLSSVVSVTSSSQPVTCNVAHPATNTKVDKTVAPSTCSKPTCPPPELLGGPSVFIFPPKP
KDTLMISRTPEVTCVVVDVSQDDPEVQFTWYINNEQVRTARPPLREQQFNSTIRVVSTLPITHQ
DWLRGKEFKCKVHNKALPAPIEKTISKARGQPLEPKVYTMGPPREELSSRSVSLTCMINGFYPS
DISVEWEKNGKAEDNYKTTPAVLDSDGSYFLYNKLSVPTSEWQRGDVFTCSVMHEALHNHYTQK
SISRSPGK

Signal sequence (1-19), heavy chain variable region (20-133),
heavy chain constant region (134-456)

[Figure 7]

SEQ ID NO 25: Amino acid sequence of rabbit type antibody heavy chain OcH02

MKHLWFFLLLVAAPRWVLSEVQLKESGGGLVKPGGSLKLSCKASGFTFNNYWMTWIRQAPGKGL
EWIASITNIDGSSYYPDSVKGRFTISRDNAQSTLYLQLNSLTAADTATYFCTRGSFDYWGQGTL
VTVSSGQPKAPSVFPLAPCCGDTPSSTVTLGCLVKGYLPEPVTVTWNSGTLTNGVRTFPSVRQS
SGLYSLSSVVSVTSSSQPVTCNVAHPATNTKVDKTVAPSTCSKPTCPPPELLGGPSVFIFPPKP
KDTLMISRTPEVTCVVVDVSQDDPEVQFTWYINNEQVRTARPPLREQQFNSTIRVVSTLPITHQ
DWLRGKEFKCKVHNKALPAPIEKTISKARGQPLEPKVYTMGPPREELSSRSVSLTCMINGFYPS
DISVEWEKNGKAEDNYKTTPAVLDSDGSYFLYNKLSVPTSEWQRGDVFTCSVMHEALHNHYTQK
SISRSPGK

Signal sequence (1-19), heavy chain variable region (20-133),
heavy chain constant region (134-456)

[Figure 8]

SEQ ID NO 27: Amino acid sequence of rabbit type antibody light chain OcL01

MVLQTQVFISLLLWISGAYGDIVMTQTPSPVSAAVGGTVTINCKASQNVNKYLNWFQQKPGQPP
KLLIYNTNNLQTGVPSRFSGSGSGTDYTLTISGVQCDDAATYYCFQHVSWLTFGGGTEVVVKGD
PVAPTVLIFPPAADQVATGTVTIVCVANKYFPDVTVTWEVDGTTQTTGIENSKTPQNSADCTYN
LSSTLTLTSTQYNSHKEYTCKVTQGTTSVVQSFNRGDC

Signal sequence (1-20), light chain variable region (21-127),
light chain constant region (128-230)

[Figure 9]
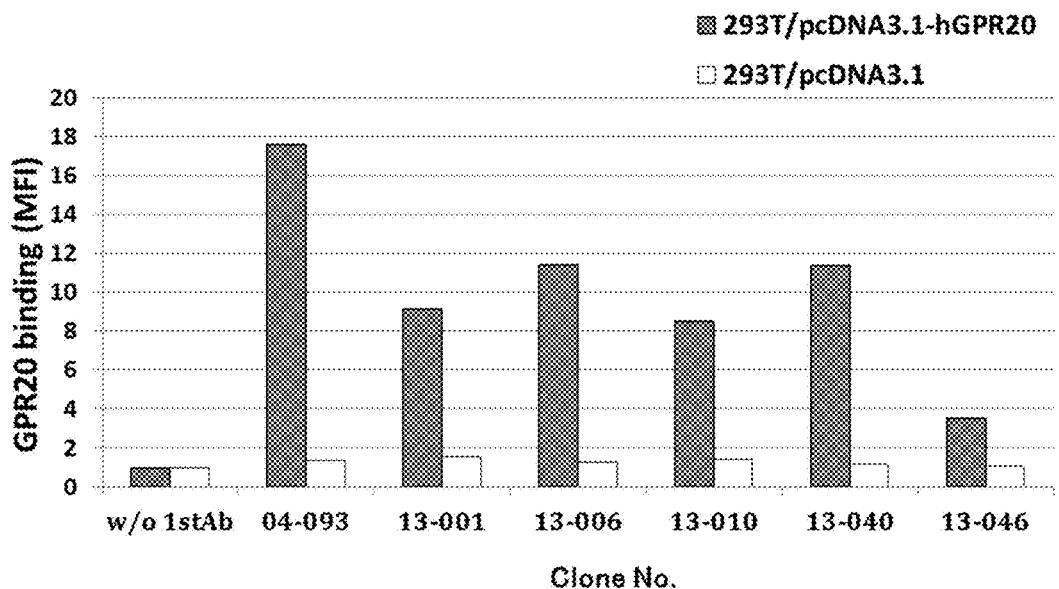
[Figure 10]
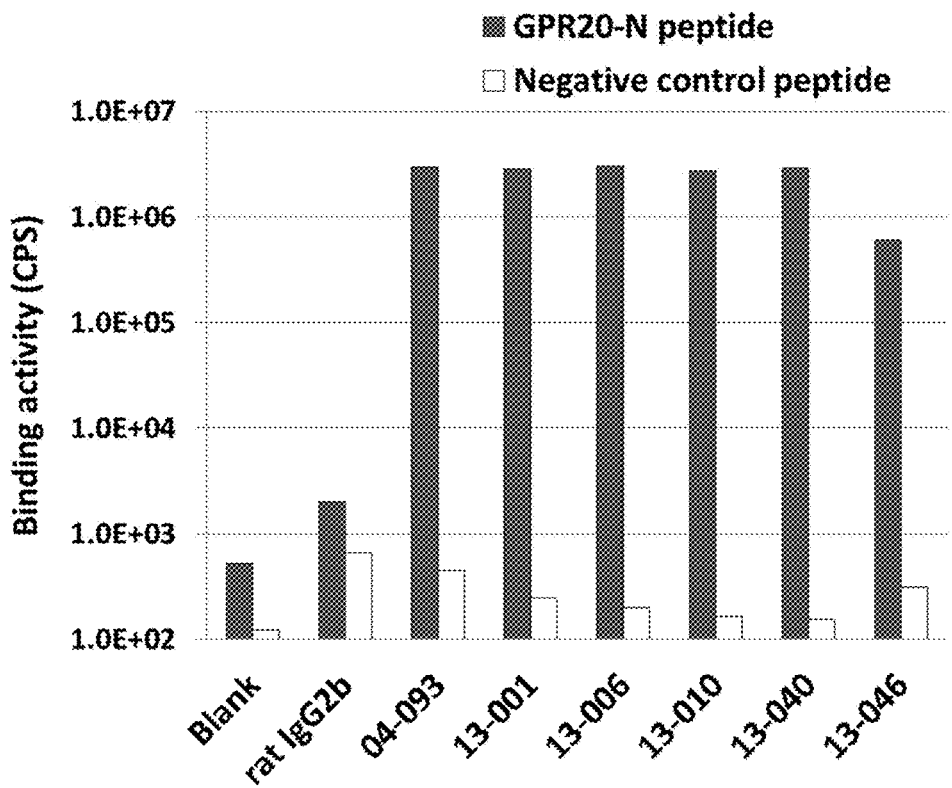

[Figure 11-1]
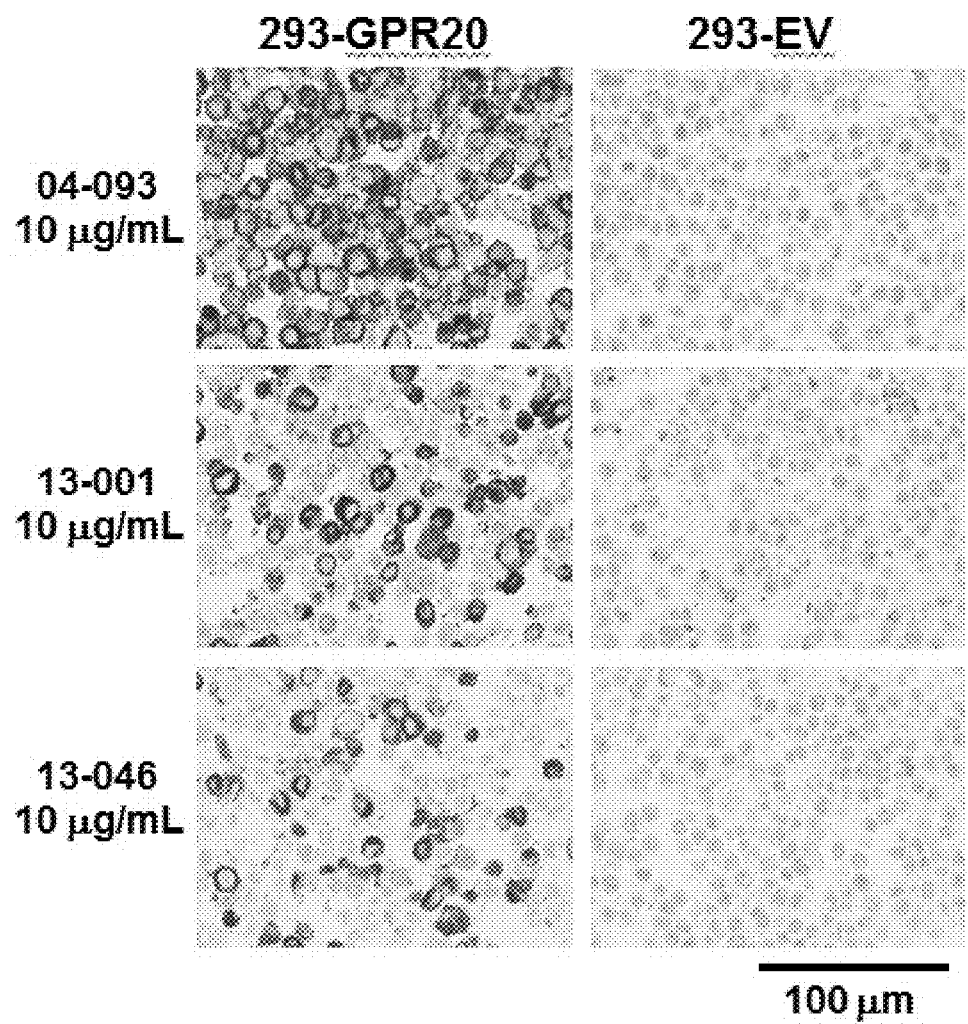

[Figure 11-2]
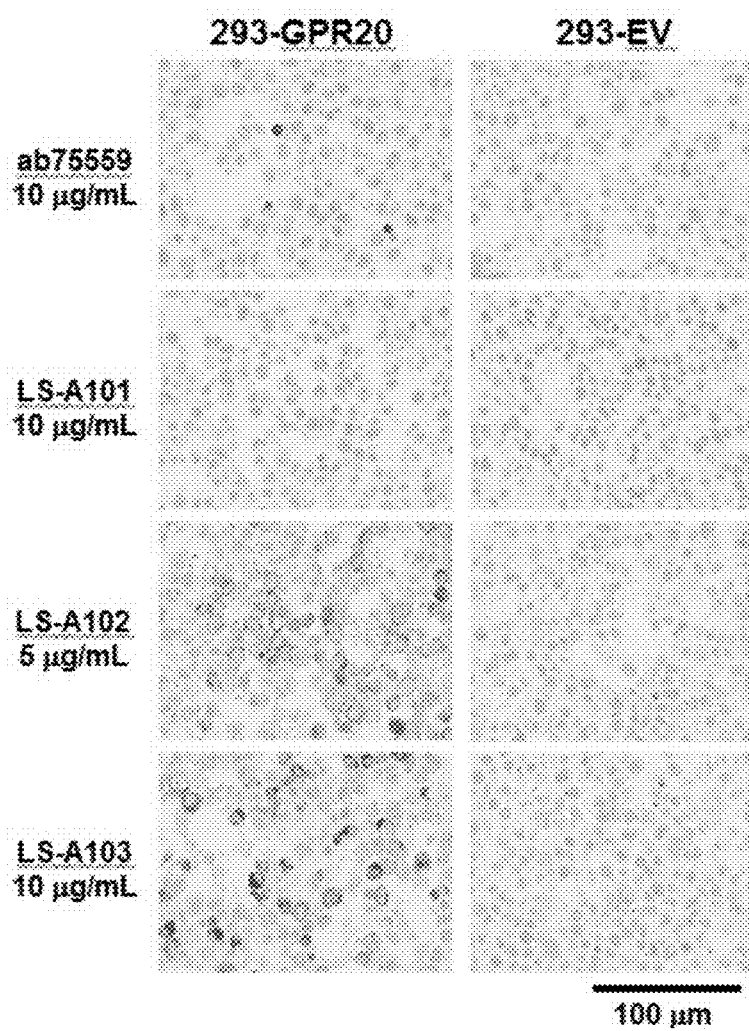

[Figure 11-3]
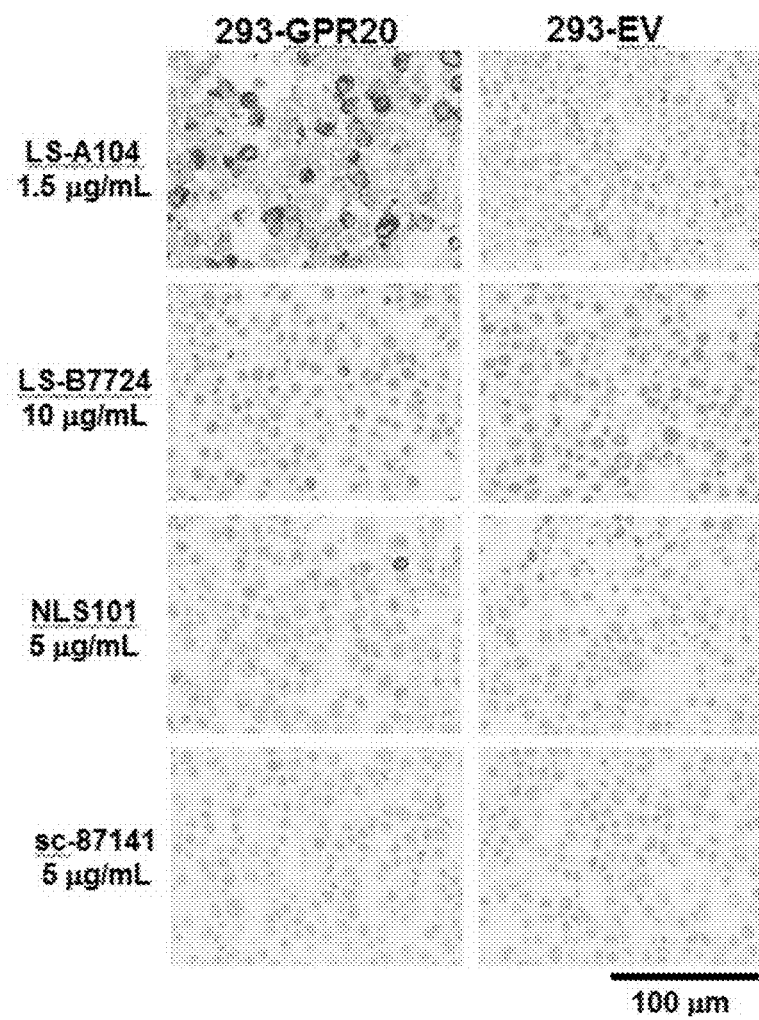

[Figure 12-1]
Stomach-derived GIST
04-093 10 μg/mL
13-001 10 μg/mL
13-046 10 μg/mL
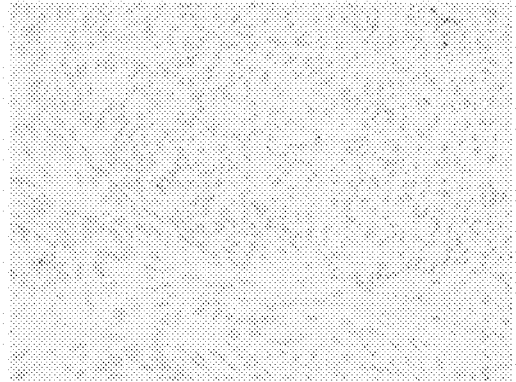
LS-A102 5 μg/mL
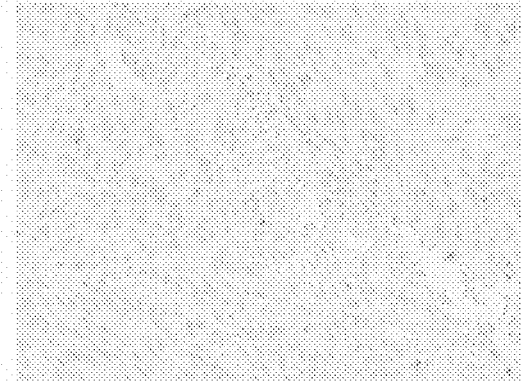
100 μm

[Figure 12-2]
Small intestine-derived GIST
04-093 10 µg/mL
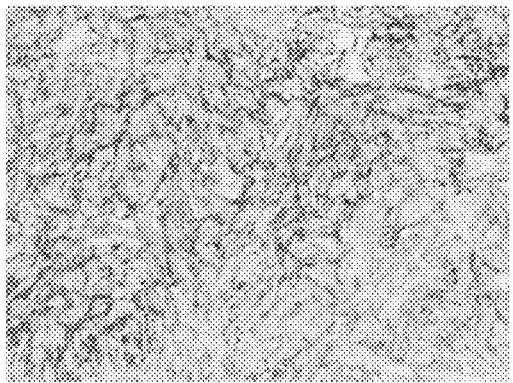
13-001 10 µg/mL
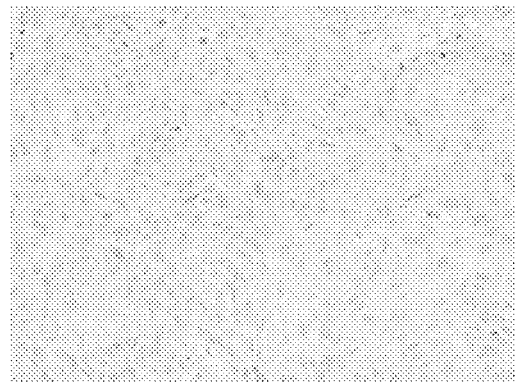
13-046 10 µg/mL
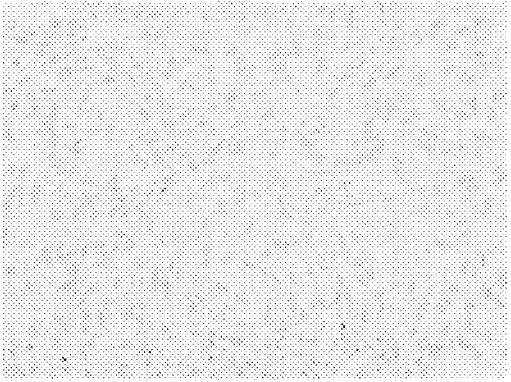
LS-A102 5 µg/mL
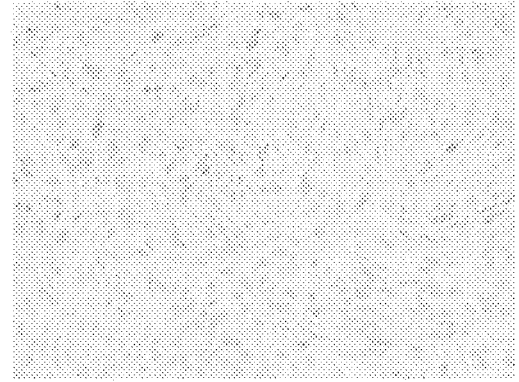
100 µm

[Figure 12-3]
Large intestine-derived GIST
04-093 10 µg/mL
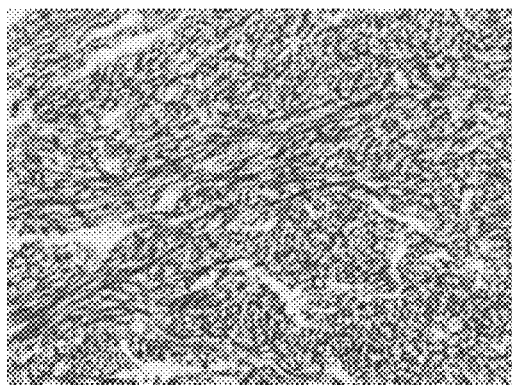
13-001 10 µg/mL
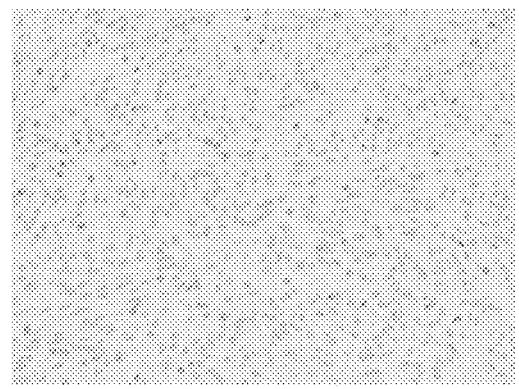
13-046 10 µg/mL
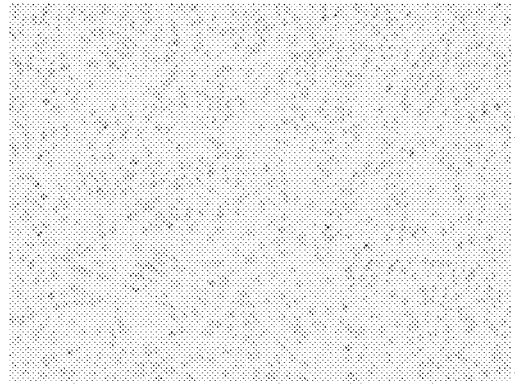
LS-A102 5 µg/mL
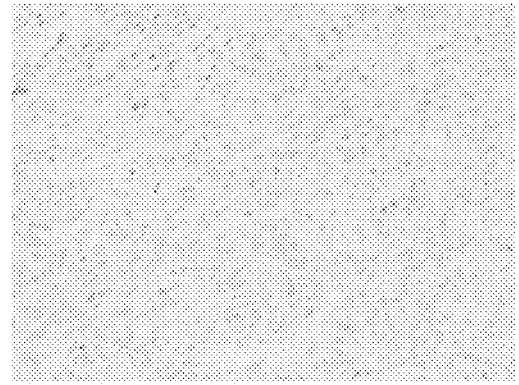
100 µm

[Figure 13]
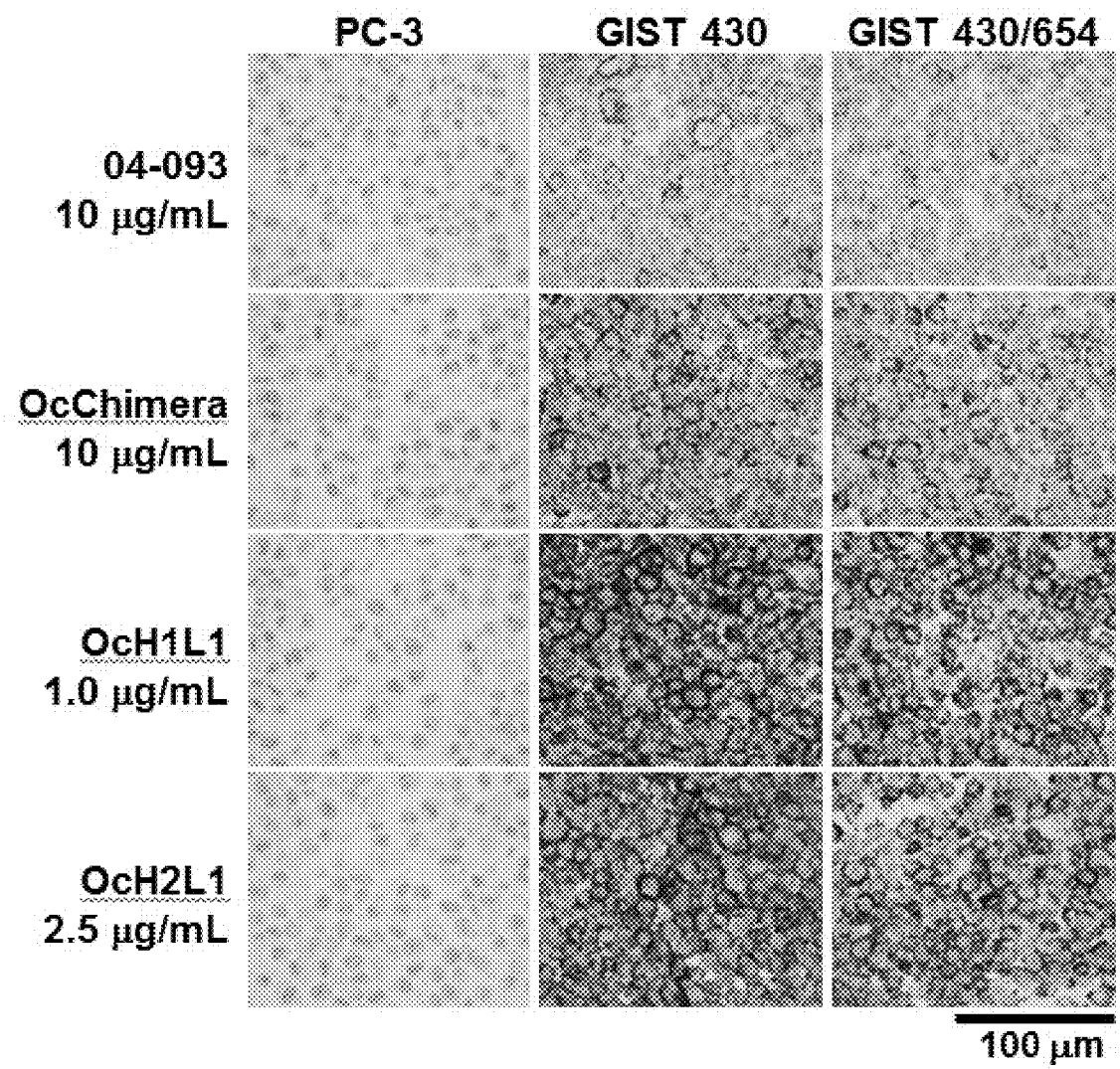

[Figure 14-1]
Stomach-derived GIST
04-093 10 μg/mL
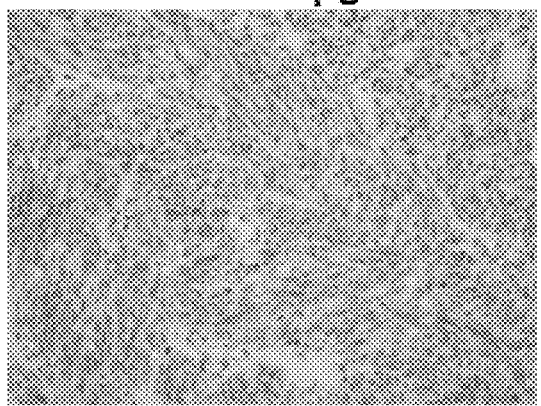
OcChimera 10 μg/mL
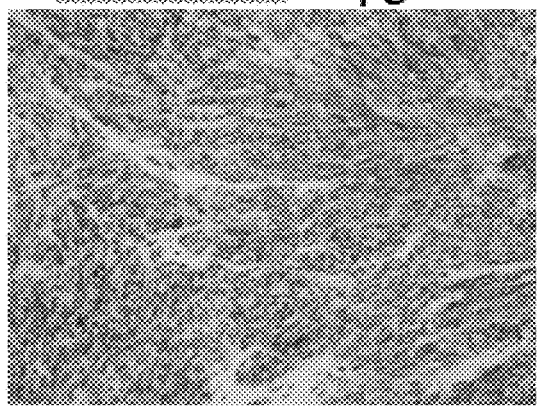
OcH1L1 1.0 μg/mL
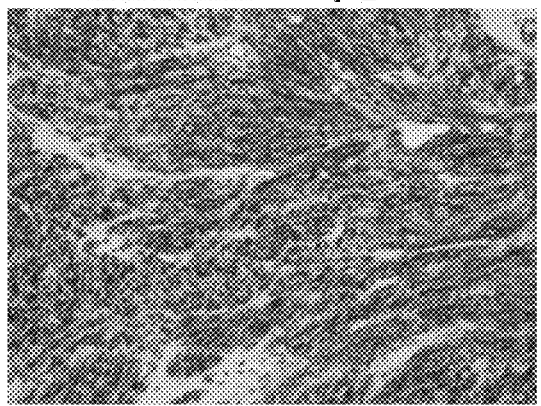
OcH2L1 2.5 μg/mL
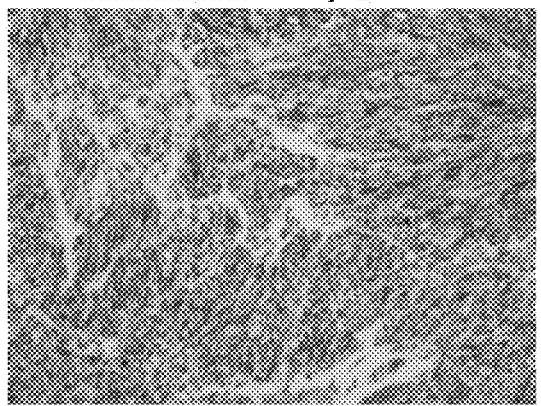
100 μm

[Figure 14-2]
Small intestine-derived GIST
04-093 10 μg/mL
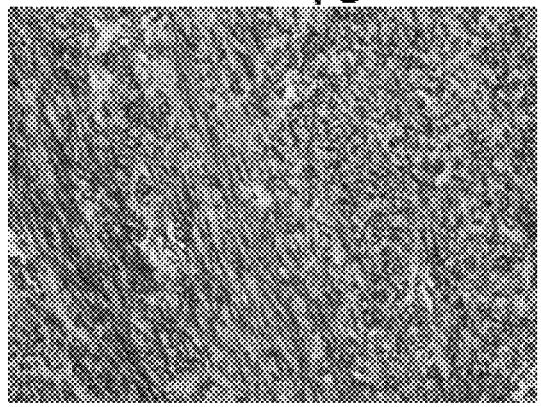
OcChimera 10 μg/mL
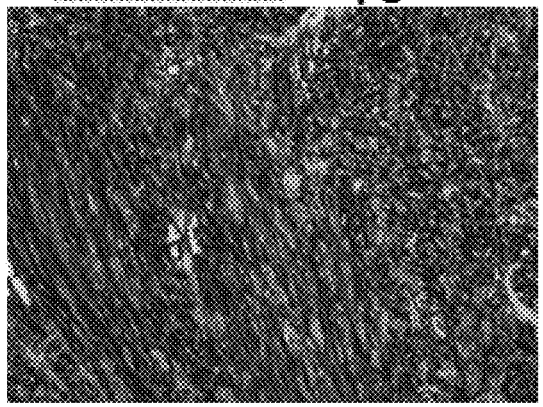
OcH1L1 1.0 μg/mL
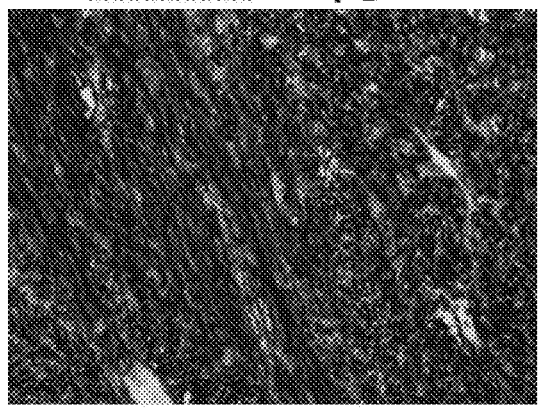
OcH2L1 2.5 μg/mL
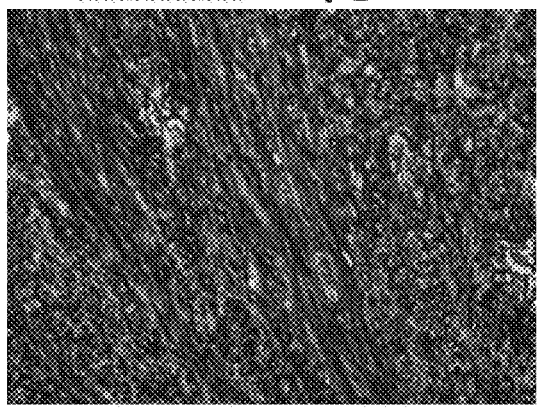
100 μm

[Figure 14-3]
Large intestine-derived GIST
04-093 10 μg/mL
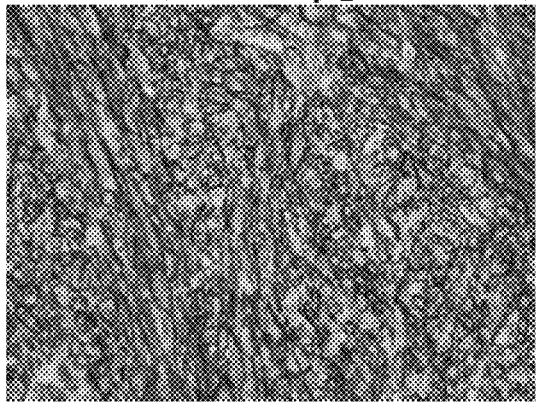
OcChimera 10 μg/mL
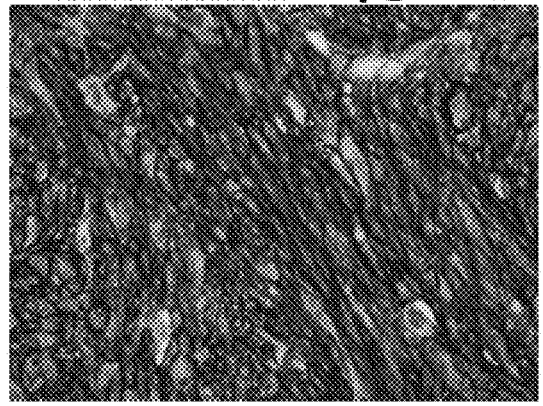
OcH1L1 1.0 μg/mL
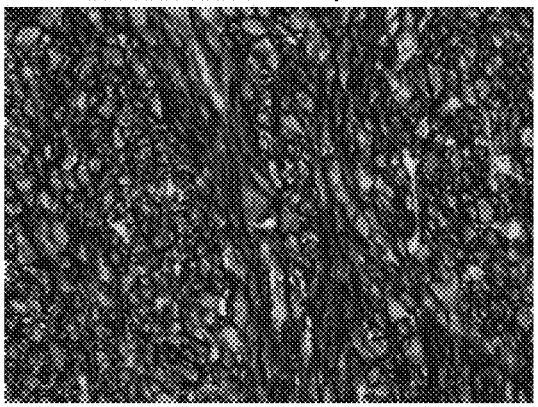
OcH2L1 2.5 μg/mL
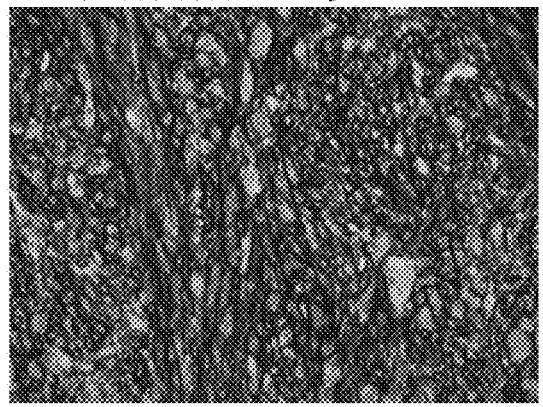
100 μm

[Figure 15]
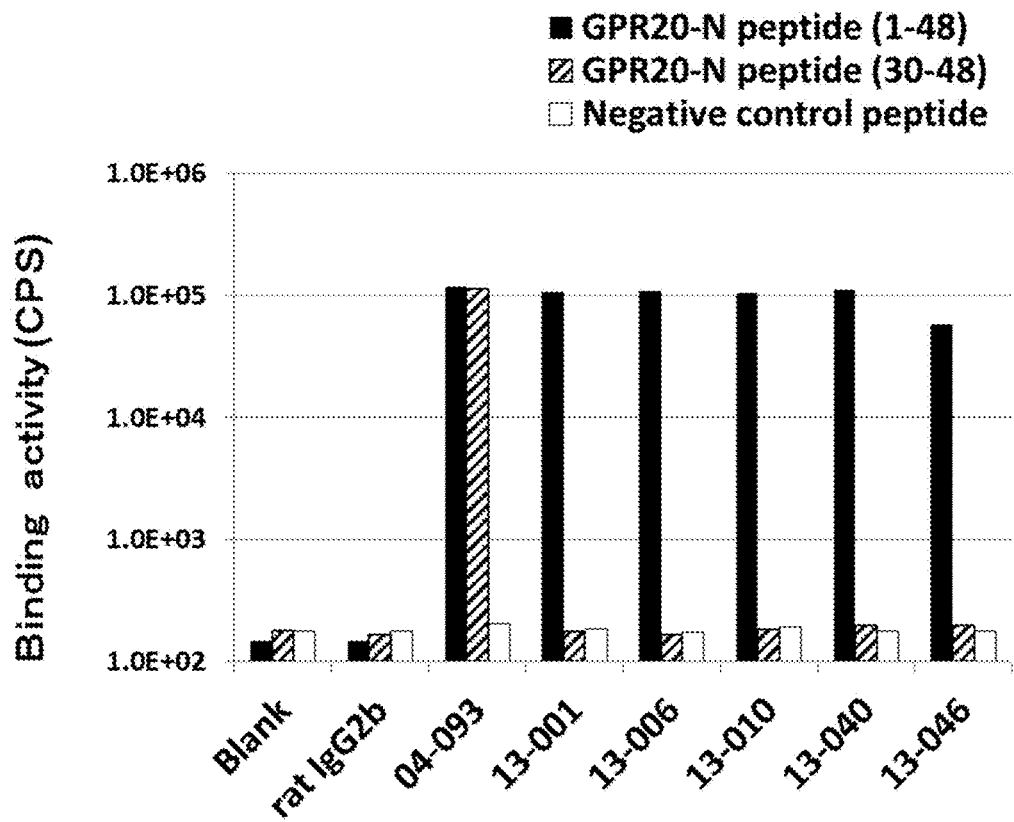
[Figure 16]
SEQ ID NO 31: Epitope of 04-093 antibody, amino acid sequence at positions 30 to 42 of human GPR20
LEVPLFHLFARLD

[Figure 17]
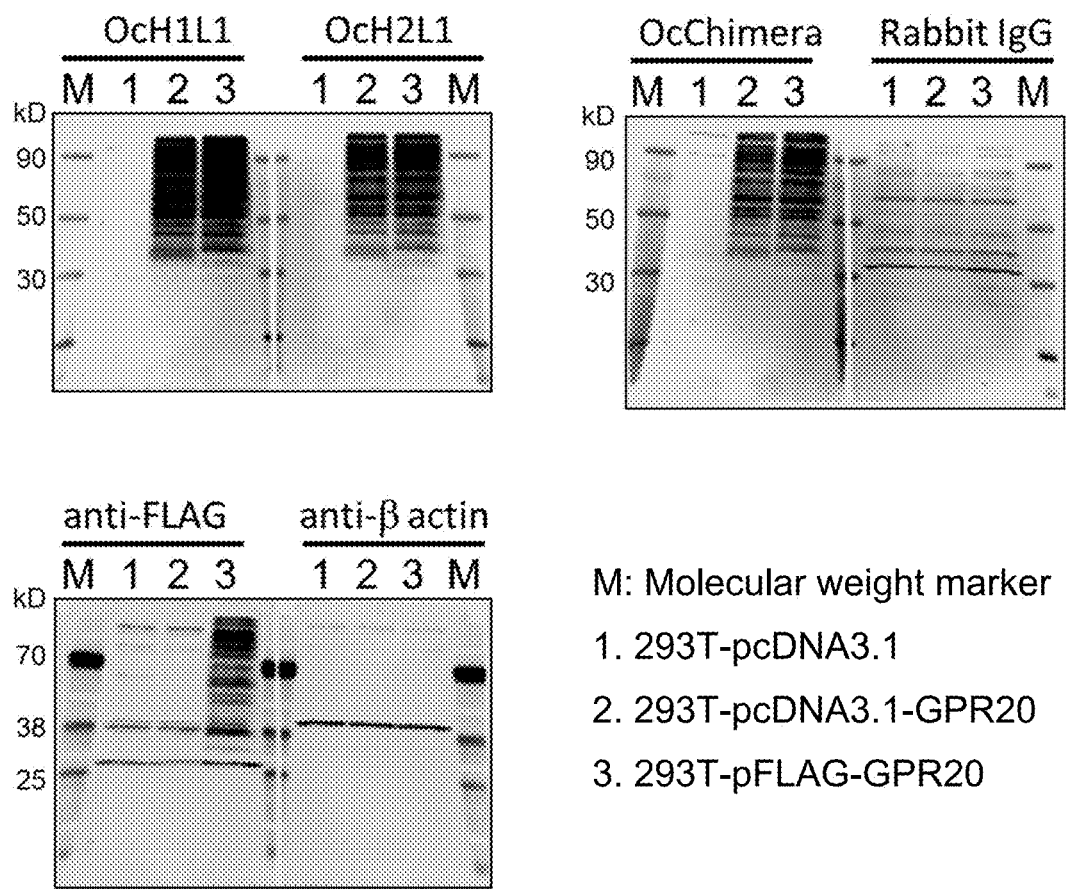
M: Molecular weight marker
1. 293T-pcDNA3.1
2. 293T-pcDNA3.1-GPR20
3. 293T-pFLAG-GPR20

SEQUENCE LISTING

<160> NUMBER OF SEQ ID NOS: 31

<210> SEQ ID NO 1
<211> LENGTH: 358
<212> TYPE: PRT
<213> ORGANISM: Homo sapiens

<400> SEQUENCE: 1

```
Met Pro Ser Val Ser Pro Ala Gly Pro Ser Ala Gly Ala Val Pro Asn
1               5                   10                  15

Ala Thr Ala Val Thr Thr Val Arg Thr Asn Ala Ser Gly Leu Glu Val
            20                  25                  30

Pro Leu Phe His Leu Phe Ala Arg Leu Asp Glu Glu Leu His Gly Thr
        35                  40                  45

Phe Pro Gly Leu Trp Leu Ala Leu Met Ala Val His Gly Ala Ile Phe
    50                  55                  60

Leu Ala Gly Leu Val Leu Asn Gly Leu Ala Leu Tyr Val Phe Cys Cys
65                  70                  75                  80

Arg Thr Arg Ala Lys Thr Pro Ser Val Ile Tyr Thr Ile Asn Leu Val
                85                  90                  95

Val Thr Asp Leu Leu Val Gly Leu Ser Leu Pro Thr Arg Phe Ala Val
            100                 105                 110

Tyr Tyr Gly Ala Arg Gly Cys Leu Arg Cys Ala Phe Pro His Val Leu
        115                 120                 125

Gly Tyr Phe Leu Asn Met His Cys Ser Ile Leu Phe Leu Thr Cys Ile
    130                 135                 140

Cys Val Asp Arg Tyr Leu Ala Ile Val Arg Pro Glu Gly Ser Arg Arg
145                 150                 155                 160

Cys Arg Gln Pro Ala Cys Ala Arg Ala Val Cys Ala Phe Val Trp Leu
                165                 170                 175

Ala Ala Gly Ala Val Thr Leu Ser Val Leu Gly Val Thr Gly Ser Arg
            180                 185                 190

Pro Cys Cys Arg Val Phe Ala Leu Thr Val Leu Glu Phe Leu Leu Pro
        195                 200                 205

Leu Leu Val Ile Ser Val Phe Thr Gly Arg Ile Met Cys Ala Leu Ser
    210                 215                 220

Arg Pro Gly Leu Leu His Gln Gly Arg Gln Arg Val Arg Ala Met
225                 230                 235                 240

Gln Leu Leu Leu Thr Val Leu Ile Ile Phe Leu Val Cys Phe Thr Pro
                245                 250                 255

Phe His Ala Arg Gln Val Ala Val Ala Leu Trp Pro Asp Met Pro His
            260                 265                 270

His Thr Ser Leu Val Val Tyr His Val Ala Val Thr Leu Ser Ser Leu
        275                 280                 285

Asn Ser Cys Met Asp Pro Ile Val Tyr Cys Phe Val Thr Ser Gly Phe
    290                 295                 300

Gln Ala Thr Val Arg Gly Leu Phe Gly Gln His Gly Glu Arg Glu Pro
305                 310                 315                 320

Ser Ser Gly Asp Val Val Ser Met His Arg Ser Ser Lys Gly Ser Gly
                325                 330                 335

Arg His His Ile Leu Ser Ala Gly Pro His Ala Leu Thr Gln Ala Leu
            340                 345                 350

Ala Asn Gly Pro Glu Ala
        355
```

<210> SEQ ID NO 2
<211> LENGTH: 1398
<212> TYPE: DNA
<213> ORGANISM: rat
<220> FEATURE:
<221> NAME/KEY: sig_peptide
<222> LOCATION: (1)..(57)

<400> SEQUENCE: 2

```
atggacatca ggctcagctt ggttttcctt gtccttttca taaaaggtgt ccagtgtgag    60
gtgcagctgg tggagtctgg gggaggccta gtgcagcctg gaaggtctct gaaactatcc   120
tgtgtagcct ctggattcac attcaacaac tactggatga cctggatccg ccaggctcca   180
gggaaggggc tggagtgggt tgcatccatt actaatattg atggtagcag ttactatcca   240
gactctgtga agggccgatt cactatctcc agagataatg taaaaagcac cctatacctg   300
caaatgaaca gtctgaggtc tgaggacacg gccacttatt actgtacaag aggatccttt   360
gattactggg gccaaggagt catggtcaca gtctcctcag cccaaacaac agccccatct   420
gtctatccac tggctcctgg atgtggtgat acaaccagct ccacggtgac tctgggatgc   480
ctggtcaagg ctatttccc tgagccagtc accgtgacct ggaactctgg agccctgtcc   540
agcgatgtgc acaccttcc agctgtcctg cagtctgggc tctacactct caccagctca   600
gtgacctcca gcacctggcc cagccagacc gtcacctgca acgtagccca cccggccagc   660
agcaccaagg tggacaagaa agttgagcgc agaaatggcg gcattgggca caaatgccct   720
acatgcccta catgtcacaa atgcccagtt cctgaactct gggtggacc atctgtcttc   780
atcttcccgc caaagcccaa ggacatcctc ttgatctccc agaacgccaa ggtcacgtgt   840
gtggtggtgg atgtgagcga ggaggagccg gacgtccagt tcagctggtt tgtgaacaac   900
gtagaagtac acacagctca gacacaaccc cgtgaggagc agtacaacag caccttcaga   960
gtggtcagtg ccctccccat ccagcaccag gactggatga gcggcaagga gttcaaatgc  1020
aaggtcaaca acaaagccct cccaagcccc atcgagaaaa ccatctcaaa acccaaaggg  1080
ctagtcagaa aaccacaggt atacgtcatg ggtccaccga cagagcagtt gactgagcaa  1140
acggtcagtt tgacctgctt gacctcaggc ttcctcccta cgacatcgg tgtggagtgg  1200
accagcaacg ggcatataga aaagaactac aagaacaccg agccagtgat ggactctgac  1260
ggttctttct tcatgtacag caagctcaat gtggaaagga caggtggga tagcagagcg  1320
cccttcgtct gctccgtggt ccacgagggt ctgcacaatc accacgtgga agagcatc   1380
tcccggcctc cgggtaaa                                               1398
```

<210> SEQ ID NO 3
<211> LENGTH: 466
<212> TYPE: PRT
<213> ORGANISM: rat
<220> FEATURE:
<221> NAME/KEY: SIGNAL
<222> LOCATION: (1)..(19)

<400> SEQUENCE: 3

```
Met Asp Ile Arg Leu Ser Leu Val Phe Leu Val Leu Phe Ile Lys Gly
1               5                   10                  15

Val Gln Cys Glu Val Gln Leu Val Glu Ser Gly Gly Gly Leu Val Gln
            20                  25                  30

Pro Gly Arg Ser Leu Lys Leu Ser Cys Val Ala Ser Gly Phe Thr Phe
        35                  40                  45
```

```
Asn Asn Tyr Trp Met Thr Trp Ile Arg Gln Ala Pro Gly Lys Gly Leu
     50                  55                  60

Glu Trp Val Ala Ser Ile Thr Asn Ile Asp Gly Ser Ser Tyr Tyr Pro
 65                  70                  75                  80

Asp Ser Val Lys Gly Arg Phe Thr Ile Ser Arg Asp Asn Val Lys Ser
                 85                  90                  95

Thr Leu Tyr Leu Gln Met Asn Ser Leu Arg Ser Glu Asp Thr Ala Thr
             100                 105                 110

Tyr Tyr Cys Thr Arg Gly Ser Phe Asp Tyr Trp Gly Gln Gly Val Met
         115                 120                 125

Val Thr Val Ser Ser Ala Gln Thr Thr Ala Pro Ser Val Tyr Pro Leu
 130                 135                 140

Ala Pro Gly Cys Gly Asp Thr Thr Ser Ser Thr Val Thr Leu Gly Cys
 145                 150                 155                 160

Leu Val Lys Gly Tyr Phe Pro Glu Pro Val Thr Val Thr Trp Asn Ser
                 165                 170                 175

Gly Ala Leu Ser Ser Asp Val His Thr Phe Pro Ala Val Leu Gln Ser
             180                 185                 190

Gly Leu Tyr Thr Leu Thr Ser Ser Val Thr Ser Ser Thr Trp Pro Ser
         195                 200                 205

Gln Thr Val Thr Cys Asn Val Ala His Pro Ala Ser Ser Thr Lys Val
 210                 215                 220

Asp Lys Lys Val Glu Arg Arg Asn Gly Gly Ile Gly His Lys Cys Pro
 225                 230                 235                 240

Thr Cys Pro Thr Cys His Lys Cys Pro Val Pro Glu Leu Leu Gly Gly
                 245                 250                 255

Pro Ser Val Phe Ile Phe Pro Pro Lys Pro Lys Asp Ile Leu Leu Ile
             260                 265                 270

Ser Gln Asn Ala Lys Val Thr Cys Val Val Asp Val Ser Glu Glu
         275                 280                 285

Glu Pro Asp Val Gln Phe Ser Trp Phe Val Asn Asn Val Glu Val His
 290                 295                 300

Thr Ala Gln Thr Gln Pro Arg Glu Glu Gln Tyr Asn Ser Thr Phe Arg
 305                 310                 315                 320

Val Val Ser Ala Leu Pro Ile Gln His Gln Asp Trp Met Ser Gly Lys
                 325                 330                 335

Glu Phe Lys Cys Lys Val Asn Asn Lys Ala Leu Pro Ser Pro Ile Glu
             340                 345                 350

Lys Thr Ile Ser Lys Pro Lys Gly Leu Val Arg Lys Pro Gln Val Tyr
         355                 360                 365

Val Met Gly Pro Pro Thr Glu Gln Leu Thr Glu Gln Thr Val Ser Leu
 370                 375                 380

Thr Cys Leu Thr Ser Gly Phe Leu Pro Asn Asp Ile Gly Val Glu Trp
 385                 390                 395                 400

Thr Ser Asn Gly His Ile Glu Lys Asn Tyr Lys Asn Thr Glu Pro Val
                 405                 410                 415

Met Asp Ser Asp Gly Ser Phe Phe Met Tyr Ser Lys Leu Asn Val Glu
             420                 425                 430

Arg Ser Arg Trp Asp Ser Arg Ala Pro Phe Val Cys Ser Val Val His
         435                 440                 445

Glu Gly Leu His Asn His His Val Glu Lys Ser Ile Ser Arg Pro Pro
 450                 455                 460

Gly Lys
```

<210> SEQ ID NO 4
<211> LENGTH: 114
<212> TYPE: PRT
<213> ORGANISM: rat

<400> SEQUENCE: 4

Glu Val Gln Leu Val Glu Ser Gly Gly Gly Leu Val Gln Pro Gly Arg
1               5                   10                  15

Ser Leu Lys Leu Ser Cys Val Ala Ser Gly Phe Thr Phe Asn Asn Tyr
            20                  25                  30

Trp Met Thr Trp Ile Arg Gln Ala Pro Gly Lys Gly Leu Glu Trp Val
        35                  40                  45

Ala Ser Ile Thr Asn Ile Asp Gly Ser Ser Tyr Tyr Pro Asp Ser Val
    50                  55                  60

Lys Gly Arg Phe Thr Ile Ser Arg Asp Asn Val Lys Ser Thr Leu Tyr
65                  70                  75                  80

Leu Gln Met Asn Ser Leu Arg Ser Glu Asp Thr Ala Thr Tyr Tyr Cys
                85                  90                  95

Thr Arg Gly Ser Phe Asp Tyr Trp Gly Gln Gly Val Met Val Thr Val
            100                 105                 110

Ser Ser

<210> SEQ ID NO 5
<211> LENGTH: 10
<212> TYPE: PRT
<213> ORGANISM: rat

<400> SEQUENCE: 5

Gly Phe Thr Phe Asn Asn Tyr Trp Met Thr
1               5                   10

<210> SEQ ID NO 6
<211> LENGTH: 10
<212> TYPE: PRT
<213> ORGANISM: rat

<400> SEQUENCE: 6

Ser Ile Thr Asn Ile Asp Gly Ser Ser Tyr
1               5                   10

<210> SEQ ID NO 7
<211> LENGTH: 5
<212> TYPE: PRT
<213> ORGANISM: rat

<400> SEQUENCE: 7

Gly Ser Phe Asp Tyr
1               5

<210> SEQ ID NO 8
<211> LENGTH: 5
<212> TYPE: PRT
<213> ORGANISM: rat

<400> SEQUENCE: 8

Asn Tyr Trp Met Thr
1               5

<210> SEQ ID NO 9

-continued

<211> LENGTH: 17
<212> TYPE: PRT
<213> ORGANISM: rat

<400> SEQUENCE: 9

Ser Ile Thr Asn Ile Asp Gly Ser Ser Tyr Tyr Pro Asp Ser Val Lys
1               5                   10                  15

Gly

<210> SEQ ID NO 10
<211> LENGTH: 696
<212> TYPE: DNA
<213> ORGANISM: rat
<220> FEATURE:
<221> NAME/KEY: sig_peptide
<222> LOCATION: (1)..(57)

<400> SEQUENCE: 10
atggctccag ttcaactctt agggctgctg ctgctctggc tcccagccat gagatgtgac        60
atccagatga cccagtctcc ttcagtcctc tctgcatctg tgggagacag agtcactctc       120
aactgcaaag caagtcagaa tgttaacaag tacttaaact ggtttcagca aaagcttgga       180
gaacctccca actcctgat atataataca acaatttgc aaacgggcat ccatcaagg          240 ttcagtggca gtggatctgg tacagattac acactcacca tcagcagcct gcagcctgaa       300
gatgttgcca catatttctg cttttcagcat gttagttggc tcacgttcgg ttctgggacc      360
aagctggaga tcaaacgggc tgatgctgca ccaactgtat ctatcttccc accatccacg       420
gaacagttag caactggagg tgcctcagtc gtgtgcctca tgaacaactt ctatcccaga       480
gacatcagtg tcaagtggaa gattgatggc actgaacgac gagatggtgt cctggacagt       540
gttactgatc aggacagcaa agacagcacg tacagcatga gcagcaccct ctcgttgacc       600
aaggctgact atgaaagtca taacctctat acctgtgagg ttgttcataa gacatcatcc       660
tcacccgtcg tcaagagctt caacaggaat gagtgt                                 696

<210> SEQ ID NO 11
<211> LENGTH: 232
<212> TYPE: PRT
<213> ORGANISM: rat
<220> FEATURE:
<221> NAME/KEY: SIGNAL
<222> LOCATION: (1)..(19)

<400> SEQUENCE: 11

Met Ala Pro Val Gln Leu Leu Gly Leu Leu Leu Trp Leu Pro Ala
1               5                   10                  15

Met Arg Cys Asp Ile Gln Met Thr Gln Ser Pro Ser Val Leu Ser Ala
                20                  25                  30

Ser Val Gly Asp Arg Val Thr Leu Asn Cys Lys Ala Ser Gln Asn Val
            35                  40                  45

Asn Lys Tyr Leu Asn Trp Phe Gln Gln Lys Leu Gly Glu Pro Pro Lys
        50                  55                  60

Leu Leu Ile Tyr Asn Thr Asn Asn Leu Gln Thr Gly Ile Pro Ser Arg
65                  70                  75                  80

Phe Ser Gly Ser Gly Ser Gly Thr Asp Tyr Thr Leu Thr Ile Ser Ser
                85                  90                  95

Leu Gln Pro Glu Asp Val Ala Thr Tyr Phe Cys Phe Gln His Val Ser
                100                 105                 110

Trp Leu Thr Phe Gly Ser Gly Thr Lys Leu Glu Ile Lys Arg Ala Asp

```
            115                 120                 125
Ala Ala Pro Thr Val Ser Ile Phe Pro Pro Ser Thr Glu Gln Leu Ala
    130                 135                 140

Thr Gly Gly Ala Ser Val Val Cys Leu Met Asn Asn Phe Tyr Pro Arg
145                 150                 155                 160

Asp Ile Ser Val Lys Trp Lys Ile Asp Gly Thr Glu Arg Arg Asp Gly
                165                 170                 175

Val Leu Asp Ser Val Thr Asp Gln Asp Ser Lys Asp Ser Thr Tyr Ser
            180                 185                 190

Met Ser Ser Thr Leu Ser Leu Thr Lys Ala Asp Tyr Glu Ser His Asn
        195                 200                 205

Leu Tyr Thr Cys Glu Val Val His Lys Thr Ser Ser Ser Pro Val Val
    210                 215                 220

Lys Ser Phe Asn Arg Asn Glu Cys
225                 230

<210> SEQ ID NO 12
<211> LENGTH: 107
<212> TYPE: PRT
<213> ORGANISM: rat

<400> SEQUENCE: 12

Asp Ile Gln Met Thr Gln Ser Pro Ser Val Leu Ser Ala Ser Val Gly
1               5                   10                  15

Asp Arg Val Thr Leu Asn Cys Lys Ala Ser Gln Asn Val Asn Lys Tyr
            20                  25                  30

Leu Asn Trp Phe Gln Gln Lys Leu Gly Glu Pro Pro Lys Leu Leu Ile
        35                  40                  45

Tyr Asn Thr Asn Asn Leu Gln Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Phe Cys Phe Gln His Val Ser Trp Leu Thr
                85                  90                  95

Phe Gly Ser Gly Thr Lys Leu Glu Ile Lys Arg
            100                 105

<210> SEQ ID NO 13
<211> LENGTH: 11
<212> TYPE: PRT
<213> ORGANISM: rat

<400> SEQUENCE: 13

Lys Ala Ser Gln Asn Val Asn Lys Tyr Leu Asn
1               5                   10

<210> SEQ ID NO 14
<211> LENGTH: 7
<212> TYPE: PRT
<213> ORGANISM: rat

<400> SEQUENCE: 14

Asn Thr Asn Asn Leu Gln Thr
1               5

<210> SEQ ID NO 15
<211> LENGTH: 8
<212> TYPE: PRT
<213> ORGANISM: rat
```

<400> SEQUENCE: 15

Phe Gln His Val Ser Trp Leu Thr
1               5

<210> SEQ ID NO 16
<211> LENGTH: 399
<212> TYPE: DNA
<213> ORGANISM: rat
<220> FEATURE:
<221> NAME/KEY: sig_peptide
<222> LOCATION: (1)..(57)

<400> SEQUENCE: 16

```
atggacatca ggctcagctt ggttttcctt gtccttttca taaaaggtgt ccagtgtgag      60
gtgcagctgg tggagtctgg gggaggccta gtgcagcctg aaggtctct gaaactatcc     120 tgtgtagcct ctggattcac attcaacaac tactggatga cctggatccg ccaggctcca    180
gggaaggggc tggagtgggt tgcatccatt actaatattg atggtagcag ttactatcca    240
gactctgtga agggccgatt cactatctcc agagataatg taaaaagcac cctatacctg    300
caaatgaaca gtctgaggtc tgaggacacg gccacttatt actgtacaag aggatccttt    360
gattactggg gccaaggagt catggtcaca gtctcctca                           399
```

<210> SEQ ID NO 17
<211> LENGTH: 381
<212> TYPE: DNA
<213> ORGANISM: rat
<220> FEATURE:
<221> NAME/KEY: sig_peptide
<222> LOCATION: (1)..(57)

<400> SEQUENCE: 17

```
atggctccag ttcaactctt agggctgctg ctgctctggc tcccagccat gagatgtgac      60
atccagatga cccagtctcc ttcagtcctc tctgcatctg tgggagacag agtcactctc    120
aactgcaaag caagtcagaa tgttaacaag tacttaaact ggtttcagca aaagcttgga    180
gaacctccca aactcctgat atataataca acaatttgc aaacgggcat cccatcaagg     240
ttcagtggca gtggatctgg tacagattac acactcacca tcagcagcct gcagcctgaa    300
gatgttgcca catatttctg cttcagcat gttagttggc tcacgttcgg ttctgggacc     360
aagctggaga tcaaacgggc t                                               381
```

<210> SEQ ID NO 18
<211> LENGTH: 1418
<212> TYPE: DNA
<213> ORGANISM: Artificial Sequence
<220> FEATURE:
<223> OTHER INFORMATION: nucleotide sequence for chimeric rabbit
      antibody heavy chain OcHch
<220> FEATURE:
<221> NAME/KEY: sig_peptide
<222> LOCATION: (26)..(82)

<400> SEQUENCE: 18

```
ccagcctccg gactctagag ccaccatgaa gcacctgtgg ttctttctgc tgctggtggc      60
cgctcctaga tgggtgctgt ctgaagtgca gctggtggaa tctggcggag gactggttca    120
gcctggcaga agcctgaagc tgagctgtgt ggccagcggc ttcaccttca caaactactg    180
gatgacctgg atccggcagg cccctggcaa aggacttgaa tgggtcgcca gcatcaccaa    240
catcgacggc agcagctact accccgacag cgtgaagggc agattcacca tcagccggga    300
```

```
caacgtgaag tctaccctgt acctgcagat gaacagcctg cggagcgagg ataccgccac    360
ctactactgt accagaggca gcttcgacta ctggggccag ggcgtgatgg tcacagttag    420
ctctggacag cccaaggctc ccagcgtttt ccctctggct ccttgctgtg cgataccec    480
tagcagcaca gtgacactgg gctgtctggt caagggctac ctgcctgaac ctgtgaccgt    540
gacctggaat agcggcaccc tgaccaacgg cgtgcggaca tttcctagcg tcagacagag    600
cagcggcctg tactctctga gcagcgtggt gtctgtgacc agcagctctc agcctgtgac    660
ctgcaatgtg gcccatcctg ccaccaacac caaggtggac aaaaccgtgg ctccctccac    720
ctgtagcaag cccacatgtc ctccaccaga gctgctcgga ggccccagcg tgttcatctt    780
tccacctaag cctaaggaca ccctgatgat cagcagaacc cctgaagtga cctgcgtggt    840
ggtggacgtg tcccaggatg atcctgaggt gcagttcacc tggtacatca acaacgagca    900
agtgcggacc gccagacctc ctctgagaga gcagcagttc aacagcacca tcagagtggt    960
gtccacactg cccatcacac accaggattg gctgcggggc aaagaattca gtgcaaggt    1020
gcacaacaag gccctgcctg ctcctatcga gaaaaccatc agcaaggcca gaggccagcc    1080
actggaaccc aaggtgtaca caatgggccc tccaagagag gaactgagca gcagatccgt    1140
gtctctgacc tgcatgatca acggcttcta ccccagcgac atcagcgtgg aatgggagaa    1200
gaatggcaag gccgaggaca actacaagac aaccCCtgcc gtgctggaca gcgacggctc    1260
ctacttcctg tacaacaagc tgagcgtgcc caccagcgaa tggcaacggg agatgtgtt    1320
tacctgcagc gtgatgcacg aggccctgca caaccactac acccagaagt ccatcagcag    1380
gtccccaggc aaatgagttt aaacggggga ggctaact                            1418
```

<210> SEQ ID NO 19
<211> LENGTH: 456
<212> TYPE: PRT
<213> ORGANISM: Artificial Sequence
<220> FEATURE:
<223> OTHER INFORMATION: amino acid sequnce for chimeric rabbit antibody heavy chain OcHch
<220> FEATURE:
<221> NAME/KEY: SIGNAL
<222> LOCATION: (1)..(19)

<400> SEQUENCE: 19

Met Lys His Leu Trp Phe Phe Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Arg Ser Leu Lys Leu Ser Cys Val Ala Ser Gly Phe Thr Phe
        35                  40                  45

Asn Asn Tyr Trp Met Thr Trp Ile Arg Gln Ala Pro Gly Lys Gly Leu
    50                  55                  60

Glu Trp Val Ala Ser Ile Thr Asn Ile Asp Gly Ser Ser Tyr Tyr Pro
65                  70                  75                  80

Asp Ser Val Lys Gly Arg Phe Thr Ile Ser Arg Asp Asn Val Lys Ser
                85                  90                  95

Thr Leu Tyr Leu Gln Met Asn Ser Leu Arg Ser Glu Asp Thr Ala Thr
            100                 105                 110

Tyr Tyr Cys Thr Arg Gly Ser Phe Asp Tyr Trp Gly Gln Gly Val Met
        115                 120                 125

Val Thr Val Ser Ser Gly Gln Pro Lys Ala Pro Ser Val Phe Pro Leu
    130                 135                 140

Ala Pro Cys Cys Gly Asp Thr Pro Ser Ser Thr Val Thr Leu Gly Cys
145                 150                 155                 160

Leu Val Lys Gly Tyr Leu Pro Glu Pro Val Thr Val Thr Trp Asn Ser
            165                 170                 175

Gly Thr Leu Thr Asn Gly Val Arg Thr Phe Pro Ser Val Arg Gln Ser
        180                 185                 190

Ser Gly Leu Tyr Ser Leu Ser Ser Val Val Ser Val Thr Ser Ser Ser
        195                 200                 205

Gln Pro Val Thr Cys Asn Val Ala His Pro Ala Thr Asn Thr Lys Val
    210                 215                 220

Asp Lys Thr Val Ala Pro Ser Thr Cys Ser Lys Pro Thr Cys Pro Pro
225                 230                 235                 240

Pro Glu Leu Leu Gly Gly Pro Ser Val Phe Ile Phe Pro Pro Lys Pro
                245                 250                 255

Lys Asp Thr Leu Met Ile Ser Arg Thr Pro Glu Val Thr Cys Val Val
            260                 265                 270

Val Asp Val Ser Gln Asp Asp Pro Glu Val Gln Phe Thr Trp Tyr Ile
        275                 280                 285

Asn Asn Glu Gln Val Arg Thr Ala Arg Pro Pro Leu Arg Glu Gln Gln
290                 295                 300

Phe Asn Ser Thr Ile Arg Val Val Ser Thr Leu Pro Ile Thr His Gln
305                 310                 315                 320

Asp Trp Leu Arg Gly Lys Glu Phe Lys Cys Lys Val His Asn Lys Ala
                325                 330                 335

Leu Pro Ala Pro Ile Glu Lys Thr Ile Ser Lys Ala Arg Gly Gln Pro
            340                 345                 350

Leu Glu Pro Lys Val Tyr Thr Met Gly Pro Pro Arg Glu Glu Leu Ser
        355                 360                 365

Ser Arg Ser Val Ser Leu Thr Cys Met Ile Asn Gly Phe Tyr Pro Ser
370                 375                 380

Asp Ile Ser Val Glu Trp Glu Lys Asn Gly Lys Ala Glu Asp Asn Tyr
385                 390                 395                 400

Lys Thr Thr Pro Ala Val Leu Asp Ser Asp Gly Ser Tyr Phe Leu Tyr
                405                 410                 415

Asn Lys Leu Ser Val Pro Thr Ser Glu Trp Gln Arg Gly Asp Val Phe
            420                 425                 430

Thr Cys Ser Val Met His Glu Ala Leu His Asn His Tyr Thr Gln Lys
        435                 440                 445

Ser Ile Ser Arg Ser Pro Gly Lys
    450                 455

<210> SEQ ID NO 20
<211> LENGTH: 746
<212> TYPE: DNA
<213> ORGANISM: Artificial Sequence
<220> FEATURE:
<223> OTHER INFORMATION: nucleotide sequnece for chimeric rabbit
      antibody light chain OcLch
<220> FEATURE:
<221> NAME/KEY: sig_peptide
<222> LOCATION: (26)..(85)

<400> SEQUENCE: 20
ccagcctccg gactctagag ccaccatggt tctgcagaca caggtgttca tcagcctgct      60
gctgtggatc tctggcgcct acggcgacat ccagatgaca cagtctccaa gcgtgctgag     120

```
cgccagcgtg ggagatagag tgaccctgaa ttgcaaggcc agccagaacg tgaacaagta    180
cctgaactgg ttccagcaga agctgggcga gcctcctaag ctgctgatct acaacaccaa    240
caacctgcag acaggcatcc ccagcagatt ttctggcagc ggctctggca ccgactacac    300
cctgaccata tctagcctgc agcctgagga cgtggcaacc tacttctgct tccaacacgt    360
gtcctggctg accttcggca gcggcacaaa gctggaaatc aagagggacc ccgtggctcc    420
ttccgtgctg ctgtttcctc caagcaaaga ggaactgacc accggcaccg ccaccattgt    480
gtgtgtggcc aacaagttct accccagcga catcaccgtg acctggaagg tggacggcac    540
aacacagcag agcggcatcg agaacagcaa gaccccctcag agccccgagg acaacacata    600
cagcctgagc agcaccctga gcctgacaag cgcccagtac aatagccaca gcgtgtacac    660
atgcgaggtg gtgcagggaa gcgcctctcc tatcgtgcag agcttcaaca gaggcgactg    720
ctgagtttaa acgggggagg ctaact                                         746
```

<210> SEQ ID NO 21
<211> LENGTH: 232
<212> TYPE: PRT
<213> ORGANISM: Artificial Sequence
<220> FEATURE:
<223> OTHER INFORMATION: amino acid sequence for chimeric rabbit
      antibody light chain OcLch
<220> FEATURE:
<221> NAME/KEY: SIGNAL
<222> LOCATION: (1)..(20)

<400> SEQUENCE: 21

```
Met Val Leu Gln Thr Gln Val Phe Ile Ser Leu Leu Trp Ile Ser
1               5                   10                  15

Gly Ala Tyr Gly Asp Ile Gln Met Thr Gln Ser Pro Ser Val Leu Ser
            20                  25                  30

Ala Ser Val Gly Asp Arg Val Thr Leu Asn Cys Lys Ala Ser Gln Asn
        35                  40                  45

Val Asn Lys Tyr Leu Asn Trp Phe Gln Gln Lys Leu Gly Glu Pro Pro
    50                  55                  60

Lys Leu Leu Ile Tyr Asn Thr Asn Asn Leu Gln Thr Gly Ile Pro Ser
65                  70                  75                  80

Arg Phe Ser Gly Ser Gly Ser Gly Thr Asp Tyr Thr Leu Thr Ile Ser
                85                  90                  95

Ser Leu Gln Pro Glu Asp Val Ala Thr Tyr Phe Cys Phe Gln His Val
            100                 105                 110

Ser Trp Leu Thr Phe Gly Ser Gly Thr Lys Leu Glu Ile Lys Arg Asp
        115                 120                 125

Pro Val Ala Pro Ser Val Leu Leu Phe Pro Pro Ser Lys Glu Glu Leu
    130                 135                 140

Thr Thr Gly Thr Ala Thr Ile Val Cys Val Ala Asn Lys Phe Tyr Pro
145                 150                 155                 160

Ser Asp Ile Thr Val Thr Trp Lys Val Asp Gly Thr Thr Gln Gln Ser
                165                 170                 175

Gly Ile Glu Asn Ser Lys Thr Pro Gln Ser Pro Glu Asp Asn Thr Tyr
            180                 185                 190

Ser Leu Ser Ser Thr Leu Ser Leu Thr Ser Ala Gln Tyr Asn Ser His
        195                 200                 205

Ser Val Tyr Thr Cys Glu Val Val Gln Gly Ser Ala Ser Pro Ile Val
    210                 215                 220

Gln Ser Phe Asn Arg Gly Asp Cys
```

<210> SEQ ID NO 22
<211> LENGTH: 1418
<212> TYPE: DNA
<213> ORGANISM: Artificial Sequence
<220> FEATURE:
<223> OTHER INFORMATION: nucleotide sequence for rabbit type antibody heavy chain OcH01
<220> FEATURE:
<221> NAME/KEY: sig_peptide
<222> LOCATION: (26)..(82)

<400> SEQUENCE: 22

```
ccagcctccg gactctagag ccaccatgaa gcacctgtgg ttctttctgc tgctggtggc      60
cgctcctaga tgggtgctgt ctgaggtgca gctgaaagag tctggcggcg acttgtgaa     120
gcctggcgga tctctgaagc tgtgctgtaa agccagcggc ttcaccttca caactactg     180
gatgacctgg atccggcagg cccctggcaa aggactggaa tggatcgcca gcatcaccaa     240
catcgacggc agcagctact acgcctcttg ggtcaacggc agattcaccc tgagcagaga     300
caacgcccag agcaccgttt gcctgcagct caattctctg acagccgccg acaccgccac     360
ctatttctgt accagaggca gcttcgacta ctggggccag ggaacactgg tcaccgttag     420
ctctggacag cccaaggctc ctagcgtgtt ccctctggct ccttgctgtg cgataccc     480
tagcagcaca gtgacactgg gctgtctggt caagggctac tgcctgaac ctgtgaccgt     540
gacctggaat agcggcaccc tgaccaacgg cgtgcggaca tttcctagcg tcagacagag     600
cagcggcctg tactctctga gcagcgtggt gtctgtgacc agcagctctc agcctgtgac     660
ctgcaatgtg gcccatcctg ccaccaacac caaggtggac aaaaccgtgg ctcccagcac     720
ctgtagcaag cccacatgtc ctccacctga gctgctcgga ggcccagcg tgttcatctt     780
tccacctaag cctaaggaca ccctgatgat cagcagaacc cctgaagtga cctgcgtggt     840
ggtggacgtg tcccaggatg atcccgaggt gcagttcacc tggtacatca acaacgagca     900
agtgcggacc gccagacctc tctgagaga gcagcagttc aacagcacca tcagagtggt     960
gtccacactg cccatcacac accaggattg gctgcgggc aaagaattca gtgcaaggt    1020
gcacaacaag gccctgcctg ctcctatcga gaaaaccatc agcaaggcca gggccagcc    1080
actggaaccc aaggtgtaca caatgggccc tccaagagag gaactgagca gcagatccgt    1140
gtctctgacc tgcatgatca cggcttcta ccccagcgac atcagcgtgg aatgggagaa    1200
gaatggcaag gccgaggaca actacaagac aacccctgcc gtgctggaca gcgacggctc    1260
ttacttcctg tacaacaagc tgagcgtgcc caccagcgaa tggcaacggg agatgtgtt    1320
tacctgcagc gtgatgcacg aggccctgca caaccactac acccagaagt ccatcagcag    1380
gtccccaggc aaatgagttt aaacggggga ggctaact                           1418
```

<210> SEQ ID NO 23
<211> LENGTH: 456
<212> TYPE: PRT
<213> ORGANISM: Artificial Sequence
<220> FEATURE:
<223> OTHER INFORMATION: amino acid sequence for rabbit type antibody heavy chain OcH01
<220> FEATURE:
<221> NAME/KEY: SIGNAL
<222> LOCATION: (1)..(19)

<400> SEQUENCE: 23

Met Lys His Leu Trp Phe Phe Leu Leu Leu Val Ala Ala Pro Arg Trp

-continued

```
  1               5                  10                 15
Val Leu Ser Glu Val Gln Leu Lys Glu Ser Gly Gly Gly Leu Val Lys
            20                  25                  30
Pro Gly Gly Ser Leu Lys Leu Cys Cys Lys Ala Ser Gly Phe Thr Phe
            35                  40                  45
Asn Asn Tyr Trp Met Thr Trp Ile Arg Gln Ala Pro Gly Lys Gly Leu
            50                  55                  60
Glu Trp Ile Ala Ser Ile Thr Asn Ile Asp Gly Ser Ser Tyr Tyr Ala
65                  70                  75                  80
Ser Trp Val Asn Gly Arg Phe Thr Leu Ser Arg Asp Asn Ala Gln Ser
            85                  90                  95
Thr Val Cys Leu Gln Leu Asn Ser Leu Thr Ala Ala Asp Thr Ala Thr
            100                 105                 110
Tyr Phe Cys Thr Arg Gly Ser Phe Asp Tyr Trp Gly Gln Gly Thr Leu
            115                 120                 125
Val Thr Val Ser Ser Gly Gln Pro Lys Ala Pro Ser Val Phe Pro Leu
            130                 135                 140
Ala Pro Cys Cys Gly Asp Thr Pro Ser Ser Thr Val Thr Leu Gly Cys
145                 150                 155                 160
Leu Val Lys Gly Tyr Leu Pro Glu Pro Val Thr Val Thr Trp Asn Ser
            165                 170                 175
Gly Thr Leu Thr Asn Gly Val Arg Thr Phe Pro Ser Val Arg Gln Ser
            180                 185                 190
Ser Gly Leu Tyr Ser Leu Ser Ser Val Val Ser Val Thr Ser Ser Ser
            195                 200                 205
Gln Pro Val Thr Cys Asn Val Ala His Pro Ala Thr Asn Thr Lys Val
            210                 215                 220
Asp Lys Thr Val Ala Pro Ser Thr Cys Ser Lys Pro Thr Cys Pro Pro
225                 230                 235                 240
Pro Glu Leu Leu Gly Gly Pro Ser Val Phe Ile Phe Pro Pro Lys Pro
            245                 250                 255
Lys Asp Thr Leu Met Ile Ser Arg Thr Pro Glu Val Thr Cys Val Val
            260                 265                 270
Val Asp Val Ser Gln Asp Asp Pro Glu Val Gln Phe Thr Trp Tyr Ile
            275                 280                 285
Asn Asn Glu Gln Val Arg Thr Ala Arg Pro Pro Leu Arg Glu Gln Gln
            290                 295                 300
Phe Asn Ser Thr Ile Arg Val Val Ser Thr Leu Pro Ile Thr His Gln
305                 310                 315                 320
Asp Trp Leu Arg Gly Lys Glu Phe Lys Cys Lys Val His Asn Lys Ala
            325                 330                 335
Leu Pro Ala Pro Ile Glu Lys Thr Ile Ser Lys Ala Arg Gly Gln Pro
            340                 345                 350
Leu Glu Pro Lys Val Tyr Thr Met Gly Pro Pro Arg Glu Glu Leu Ser
            355                 360                 365
Ser Arg Ser Val Ser Leu Thr Cys Met Ile Asn Gly Phe Tyr Pro Ser
            370                 375                 380
Asp Ile Ser Val Glu Trp Glu Lys Asn Gly Lys Ala Glu Asp Asn Tyr
385                 390                 395                 400
Lys Thr Thr Pro Ala Val Leu Asp Ser Asp Gly Ser Tyr Phe Leu Tyr
            405                 410                 415
Asn Lys Leu Ser Val Pro Thr Ser Glu Trp Gln Arg Gly Asp Val Phe
            420                 425                 430
```

Thr Cys Ser Val Met His Glu Ala Leu His Asn His Tyr Thr Gln Lys
        435                 440                 445

Ser Ile Ser Arg Ser Pro Gly Lys
        450                 455

<210> SEQ ID NO 24
<211> LENGTH: 1418
<212> TYPE: DNA
<213> ORGANISM: Artificial Sequence
<220> FEATURE:
<223> OTHER INFORMATION: nucleotide sequence for rabbit type antibody
      heavy chain OcH02
<220> FEATURE:
<221> NAME/KEY: sig_peptide
<222> LOCATION: (26)..(82)

<400> SEQUENCE: 24
ccagcctccg gactctagag ccaccatgaa gcacctgtgg ttctttctgc tgctggtggc      60
cgctcctaga tgggtgctgt ctgaggtgca gctgaaagag tctggcggcg acttgtgaa     120 gcctggcgga tctctgaagc tgagctgtaa agccagcggc ttcaccttca caactactg     180 gatgacctgg atccggcagg cccctggcaa aggactggaa tggatcgcca gcatcaccaa     240
catcgacggc agcagctact accccgacag cgtgaagggc agattcacca tcagcagaga     300
caacgcccag agcaccctgt acctgcagct caattctctg acagccgccg acaccgccac     360
ctatttctgt accagaggca gcttcgacta ctggggccag ggaacactgg tcaccgttag     420
ctctggacag cccaaggctc ctagcgtgtt ccctctggct ccttgctgtg cgataccc     480 tagcagcaca gtgacactgg gctgtctggt caagggctac ctgcctgaac ctgtgaccgt     540
gacctggaat agcggcaccc tgaccaacgg cgtgcggaca tttcctagcg tcagacagag     600
cagcggcctg tactctctga gcagcgtggt gtctgtgacc agcagctctc agcctgtgac     660
ctgcaatgtg gccatcctg ccaccaacac caaggtggaa aaaccgtggt ctcccagcac     720
ctgtagcaag cccacatgtc ctccacctga gctgctcgga ggccccagcg tgttcatctt     780
tccacctaag cctaaggaca ccctgatgat cagcagaacc cctgaagtga cctgcgtggt     840
ggtggacgtg tcccaggatg atcccgaggt gcagttcacc tggtacatca acaacgagca     900
agtgcggacc gccagacctc tctgagaga gcagcagttc aacagcacca tcagagtggt     960
gtccacactg cccatcacac accaggattg gctgcggggc aaagaattca gtgcaaggt    1020 gcacaacaag gccctgcctg ctcctatcga gaaaccatc tccaaggcca gaggccagcc    1080
actggaaccc aaggtgtaca caatgggccc tccaagagag gaactgagca gcagatccgt    1140
gtctctgacc tgcatgatca cggcttcta ccccagcgac atcagcgtgg aatgggagaa    1200
gaatggcaag gccgaggaca actacaagac aaccccctgcc gtgctggaca cgacggctc    1260 ttacttcctg tacaacaagc tgagcgtgcc caccagcgaa tggcaacggg gagatgtgtt    1320
cacatgcagc gtgatgcacg aggccctgca caaccactac acccagaagt ccatctctcg    1380
gagccccggc aaatgagttt aaacggggga ggctaact                            1418

<210> SEQ ID NO 25
<211> LENGTH: 456
<212> TYPE: PRT
<213> ORGANISM: Artificial Sequence
<220> FEATURE:
<223> OTHER INFORMATION: amino acid sequence for rabbit type antobody
      heavy chain OcH02
<220> FEATURE:
<221> NAME/KEY: SIGNAL

<222> LOCATION: (1)..(19)

<400> SEQUENCE: 25

```
Met Lys His Leu Trp Phe Phe Leu Leu Leu Val Ala Ala Pro Arg Trp
1               5                   10                  15

Val Leu Ser Glu Val Gln Leu Lys Glu Ser Gly Gly Gly Leu Val Lys
            20                  25                  30

Pro Gly Gly Ser Leu Lys Leu Ser Cys Lys Ala Ser Gly Phe Thr Phe
        35                  40                  45

Asn Asn Tyr Trp Met Thr Trp Ile Arg Gln Ala Pro Gly Lys Gly Leu
    50                  55                  60

Glu Trp Ile Ala Ser Ile Thr Asn Ile Asp Gly Ser Ser Tyr Tyr Pro
65                  70                  75                  80

Asp Ser Val Lys Gly Arg Phe Thr Ile Ser Arg Asp Asn Ala Gln Ser
                85                  90                  95

Thr Leu Tyr Leu Gln Leu Asn Ser Leu Thr Ala Ala Asp Thr Ala Thr
            100                 105                 110

Tyr Phe Cys Thr Arg Gly Ser Phe Asp Tyr Trp Gly Gln Gly Thr Leu
        115                 120                 125

Val Thr Val Ser Ser Gly Gln Pro Lys Ala Pro Ser Val Phe Pro Leu
    130                 135                 140

Ala Pro Cys Cys Gly Asp Thr Pro Ser Ser Thr Val Thr Leu Gly Cys
145                 150                 155                 160

Leu Val Lys Gly Tyr Leu Pro Glu Pro Val Thr Val Thr Trp Asn Ser
                165                 170                 175

Gly Thr Leu Thr Asn Gly Val Arg Thr Phe Pro Ser Val Arg Gln Ser
            180                 185                 190

Ser Gly Leu Tyr Ser Leu Ser Ser Val Val Ser Val Thr Ser Ser Ser
        195                 200                 205

Gln Pro Val Thr Cys Asn Val Ala His Pro Ala Thr Asn Thr Lys Val
    210                 215                 220

Asp Lys Thr Val Ala Pro Ser Thr Cys Ser Lys Pro Thr Cys Pro Pro
225                 230                 235                 240

Pro Glu Leu Leu Gly Gly Pro Ser Val Phe Ile Phe Pro Pro Lys Pro
                245                 250                 255

Lys Asp Thr Leu Met Ile Ser Arg Thr Pro Glu Val Thr Cys Val Val
            260                 265                 270

Val Asp Val Ser Gln Asp Asp Pro Glu Val Gln Phe Thr Trp Tyr Ile
        275                 280                 285

Asn Asn Glu Gln Val Arg Thr Ala Arg Pro Pro Leu Arg Glu Gln Gln
    290                 295                 300

Phe Asn Ser Thr Ile Arg Val Val Ser Thr Leu Pro Ile Thr His Gln
305                 310                 315                 320

Asp Trp Leu Arg Gly Lys Glu Phe Lys Cys Lys Val His Asn Lys Ala
                325                 330                 335

Leu Pro Ala Pro Ile Glu Lys Thr Ile Ser Lys Ala Arg Gly Gln Pro
            340                 345                 350

Leu Glu Pro Lys Val Tyr Thr Met Gly Pro Pro Arg Glu Glu Leu Ser
        355                 360                 365

Ser Arg Ser Val Ser Leu Thr Cys Met Ile Asn Gly Phe Tyr Pro Ser
    370                 375                 380

Asp Ile Ser Val Glu Trp Glu Lys Asn Gly Lys Ala Glu Asp Asn Tyr
385                 390                 395                 400
```

```
Lys Thr Thr Pro Ala Val Leu Asp Ser Asp Gly Ser Tyr Phe Leu Tyr
            405                 410                 415

Asn Lys Leu Ser Val Pro Thr Ser Glu Trp Gln Arg Gly Asp Val Phe
        420                 425                 430

Thr Cys Ser Val Met His Glu Ala Leu His Asn His Tyr Thr Gln Lys
    435                 440                 445

Ser Ile Ser Arg Ser Pro Gly Lys
450                 455

<210> SEQ ID NO 26
<211> LENGTH: 740
<212> TYPE: DNA
<213> ORGANISM: Artificial Sequence
<220> FEATURE:
<223> OTHER INFORMATION: nucleotide sequnce for rabbit type antibody
      light chain OcL01
<220> FEATURE:
<221> NAME/KEY: sig_peptide
<222> LOCATION: (26)..(85)

<400> SEQUENCE: 26
ccagcctccg gactctagag ccaccatggt tctgcagaca caggtgttca tcagcctgct      60
gctgtggatc tctggcgcct acggcgacat cgtgatgacc cagacacctt ctccagtgtc     120
tgccgccgtt ggcggcaccg tgacaatcaa ttgcaaggcc agccagaacg tgaacaagta     180
cctgaactgg ttccagcaga gcccggcca gcctcctaag ctgctgatct acaacaccaa     240
caacctgcag accggcgtgc ccagcagatt ttctggctct ggcagcggca ccgactacac     300
cctgacaatt tctggcgtgc agtgcgacga tgccgccacc tactactgct ttcagcacgt     360
gtcctggctg acctttggcg gcggaacaga ggttgtggtc aagggcgatc tgtggctcc     420 taccgtgctg atctttccac cagccgctga tcaggtggcc acaggcacag tgaccattgt     480
gtgcgtggcc aacaagtact tccccgacgt gaccgtgacc tgggaagtcg atggcaccac     540
acagaccacc ggcatcgaga acagcaagac ccctcagaac agcgccgact gcacctacaa     600
cctgagcagc acactgaccc tgacctccac acagtacaac agccacaaag agtacacctg     660
taaagtcacc cagggcacca ccagcgtggt gcagagcttc aatagaggcg actgctgagt     720
ttaaacgggg gaggctaact                                                 740

<210> SEQ ID NO 27
<211> LENGTH: 230
<212> TYPE: PRT
<213> ORGANISM: Artificial Sequence
<220> FEATURE:
<223> OTHER INFORMATION: amino acid sequence for rabbit type antibody
      light chian OcL01
<220> FEATURE:
<221> NAME/KEY: SIGNAL
<222> LOCATION: (1)..(20)

<400> SEQUENCE: 27

Met Val Leu Gln Thr Gln Val Phe Ile Ser Leu Leu Trp Ile Ser
1               5                   10                  15

Gly Ala Tyr Gly Asp Ile Val Met Thr Gln Thr Pro Ser Pro Val Ser
            20                  25                  30

Ala Ala Val Gly Gly Thr Val Thr Ile Asn Cys Lys Ala Ser Gln Asn
        35                  40                  45

Val Asn Lys Tyr Leu Asn Trp Phe Gln Gln Lys Pro Gly Gln Pro Pro
    50                  55                  60

Lys Leu Leu Ile Tyr Asn Thr Asn Asn Leu Gln Thr Gly Val Pro Ser
```

```
            65                  70                  75                  80
    Arg Phe Ser Gly Ser Gly Ser Gly Thr Asp Tyr Thr Leu Thr Ile Ser
                        85                  90                  95

Gly Val Gln Cys Asp Asp Ala Ala Thr Tyr Tyr Cys Phe Gln His Val
                    100                 105                 110

Ser Trp Leu Thr Phe Gly Gly Gly Thr Glu Val Val Lys Gly Asp
                115                 120                 125

Pro Val Ala Pro Thr Val Leu Ile Phe Pro Pro Ala Ala Asp Gln Val
    130                 135                 140

Ala Thr Gly Thr Val Thr Ile Val Cys Val Ala Asn Lys Tyr Phe Pro
    145                 150                 155                 160

Asp Val Thr Val Thr Trp Glu Val Asp Gly Thr Thr Gln Thr Thr Gly
                    165                 170                 175

Ile Glu Asn Ser Lys Thr Pro Gln Asn Ser Ala Asp Cys Thr Tyr Asn
                180                 185                 190

Leu Ser Ser Thr Leu Thr Leu Thr Ser Thr Gln Tyr Asn Ser His Lys
                195                 200                 205

Glu Tyr Thr Cys Lys Val Thr Gln Gly Thr Thr Ser Val Val Gln Ser
        210                 215                 220

Phe Asn Arg Gly Asp Cys
    225                 230

<210> SEQ ID NO 28
<211> LENGTH: 449
<212> TYPE: DNA
<213> ORGANISM: Artificial Sequence
<220> FEATURE:
<223> OTHER INFORMATION: DNA fragment comprising human light chain
      signal sequence and human kappa chain constant region

<400> SEQUENCE: 28
gcctccggac tctagagcca ccatggtgct gcagacccag gtgttcatct ccctgctgct     60
gtggatctcc ggcgcgtacg gcgatatcgt gatgattaaa cgtacggtgg ccgcccctc    120
cgtgttcatc ttccccccct ccgacgagca gctgaagtcc ggcaccgcct ccgtggtgtg    180
cctgctgaat aacttctacc ccagagaggc caaggtgcag tggaaggtgg acaacgcccc    240
gcagtccggg aactcccagg agagcgtgac cgagcaggac agcaaggaca gcacctacag    300
cctgagcagc accctgaccc tgagcaaagc cgactacgag aagcacaagg tgtacgcctg    360
cgaggtgacc caccagggcc tgagctcccc cgtcaccaag agcttcaaca ggggggagtg    420
ttagggggcc gtttaaacgg gggaggcta                                      449

<210> SEQ ID NO 29
<211> LENGTH: 48
<212> TYPE: PRT
<213> ORGANISM: Homo sapiens

<400> SEQUENCE: 29

Met Pro Ser Val Ser Pro Ala Gly Pro Ser Ala Gly Ala Val Pro Asn
1               5                   10                  15

Ala Thr Ala Val Thr Thr Val Arg Thr Asn Ala Ser Gly Leu Glu Val
            20                  25                  30

Pro Leu Phe His Leu Phe Ala Arg Leu Asp Glu Glu Leu His Gly Thr
        35                  40                  45

<210> SEQ ID NO 30
<211> LENGTH: 19
```

```
<212> TYPE: PRT
<213> ORGANISM: Homo sapiens

<400> SEQUENCE: 30

Leu Glu Val Pro Leu Phe His Leu Phe Ala Arg Leu Asp Glu Glu Leu
1               5                   10                  15

His Gly Thr

<210> SEQ ID NO 31
<211> LENGTH: 13
<212> TYPE: PRT
<213> ORGANISM: Homo sapiens

<400> SEQUENCE: 31

Leu Glu Val Pro Leu Phe His Leu Phe Ala Arg Leu Asp
1               5                   10
```

ANTI-GPR20 ANTIBODY

CROSS-REFERENCE TO RELATED APPLICATIONS

The present application claims priority under 37 U.S.C. § 371 to International Patent Application No. PCT/JP2018/013106, filed Mar. 29, 2018, which claims priority to and the benefit of Japanese Patent Application No. 2017-067164, filed on Mar. 30, 2017. The contents of these applications are hereby incorporated by reference in their entireties.

SEQUENCE LISTING

The instant application contains a Sequence Listing which has been submitted in ASCII format via EFS-Web and is hereby incorporated by reference in its entirety. Said ASCII copy, created on Mar. 30, 2017, is named 098065-0236_SL.txt and is 43 kb in size.

TECHNICAL FIELD

The present invention relates to a novel anti-GPR20 antibody, a functional fragment of the antibody, a modification of the antibody, a nucleotide comprising a nucleotide sequence encoding the amino acid sequence of the antibody, a vector having an insert of the nucleotide, a cell transfected with the nucleotide or the vector, a method for producing the antibody, comprising a step of culturing the cell, a pharmaceutical composition, a composition for diagnosis or for testing, etc.

BACKGROUND ART

GPR20 (G protein-coupled receptor 20) is a seven-pass transmembrane protein composed of 358 amino acids, which belongs to class A of the G protein-coupled receptor (GPCR) family, and this protein has N-terminal extracellular and C-terminal intracellular domains. GPR20 has an amino acid sequence similar to that of GPCR which recognizes a nucleotide or a lipid. However, neither physiological functions nor in vivo ligands have been identified for GPR20. From an experiment that caused HEK293 cells to express GPR20, it has been reported that GPR20 constitutively activates Gi trimeric G proteins under conditions without ligand stimulation (Non Patent Literature 1).

GPR20 has been confirmed to have messenger RNA (mRNA) expression in the heart, the brain, placenta, the lung, the liver, skeletal muscle, the kidney, the pancreas, the spleen, the thymus, the prostate, the testis, the ovary, the small intestine, the rectum, and leukocytes, and, in particular, its high expression in the small intestine has been reported (Non Patent Literature 1). In the brain, the expression in the thalamus, the putamen, and the caudatum has been reported (Non Patent Literature 2). Also, the mRNA expression of GPR20 has been reported in gastrointestinal stromal tumor (GIST) (Non Patent Literature 3) or some interstitial cells of Cajal (ICCs) which are present in the plexus and the like in the gastrointestinal muscular layer and are involved in intestinal peristalsis. ICCs are the origin cells of GIST, and it has been reported that the expression of GPR20 is regulated by ets variant 1 (ETV1), which is a major transcriptional factor of GIST (Non Patent Literature 4).

GPR20-deficient mice have exhibited the phenotype of hyperactivity disorder characterized by an increase in total distance travelled in open field tests, suggesting that GPR20 is associated with spontaneous activity in the central nervous system (Patent Literature 1).

Thus, the provision of a method that can detect the expression of GPR20 is useful in testing or diagnosis that operates by identifying tumor (e.g., GIST) cells, normal interstitial cells of Cajal present in the gastrointestinal tract, cells present in the brain, and the like as GPR20-positive cells.

Polyclonal antibodies reportedly capable of detecting human GPR20 in formalin-fixed tissues have heretofore been known, but exhibit insufficient detection sensitivity or reaction specificity. There has been a problem for providing antibodies of uniform quality. Furthermore, no monoclonal antibody useful in the immunohistochemical staining of GPR20 is known.

CITATION LIST

Patent Literature

Patent Literature 1: US 2003/0018989 A1 Non Patent Literature

Non Patent Literature 1: Hase M., et al., J Biol Chem. (2008) 283, 12747-12755

Non Patent Literature 2: O'Dowd B. F., Gene 187 (1997) 75-81

Non Patent Literature 3: Allander S. V., et al., CANCER RESEARCH (2001) 61, 8624-8628

Non Patent Literature 4: Chi P., et al., Nature. (2010) 467 (7317): 849-853

SUMMARY OF INVENTION

Technical Problem

It is an object of the present invention to provide an antibody specifically binding to GPR20.

It is another object of the present invention to provide a reagent for GPR20 detection comprising an anti-GPR20 antibody. It is a further alternative object of the present invention to provide a reagent for diagnosis or a composition for testing, etc. of a disease related to the expression of GPR20, comprising an anti-GPR20 antibody.

The objects of the present invention also include a nucleotide encoding the amino acid sequence of the antibody, a vector having an insert of the nucleotide, a cell transfected with the nucleotide or the vector, a method for producing the antibody, comprising a step of culturing the cell, etc.

It is a further alternative object of the present invention to provide a pharmaceutical composition containing the anti-GPR20 antibody, and a method for treating a disease involving the expression of GPR20 using the pharmaceutical composition.

Solution to Problem

The inventors have conducted intensive studies directed towards achieving the above-described objects, and completed the present invention by developing a novel anti-GPR20 antibody and finding that GPR20 can be detected using the antibody. Specifically, the present invention includes the following aspects of the invention:

(1) an antibody specifically binding to a peptide comprising the amino acid sequence at amino acid positions 1 to 48 in SEQ ID NO: 1, or an antigen-binding fragment of the antibody;

(2) an antibody having competitive inhibitory activity, for binding to GPR20, against an antibody having a heavy chain consisting of the amino acid sequence at amino acid positions 20 to 466 in SEQ ID NO: 3 and a light chain consisting of the amino acid sequence at amino acid positions 20 to 232 in SEQ ID NO: 11, or an antigen-binding fragment of the antibody;

(3) the antibody or the antigen-binding fragment of the antibody according to (1) or (2), which binds to an epitope consisting of the amino acid sequence LEVPLFHLFARLD (SEQ ID NO: 31);

(4) the antibody or the antigen-binding fragment of the antibody according to any one of (1) to (3), wherein the heavy chain sequence comprises a variable region having CDRH1 consisting of the amino acid sequence shown in SEQ ID NO: 5 or 8, CDRH2 consisting of the amino acid sequence shown in SEQ ID NO: 6 or 9, and CDRH3 consisting of the amino acid sequence shown in SEQ ID NO: 7; and the light chain sequence comprises a variable region having CDRL1 consisting of the amino acid sequence shown in SEQ ID NO: 13, CDRL2 consisting of the amino acid sequence shown in SEQ ID NO: 14, and CDRL3 consisting of the amino acid sequence shown in SEQ ID NO: 15;

(5) the antibody or the antigen-binding fragment of the antibody according to any one of (1) to (4), which comprises a heavy chain variable region consisting of the amino acid sequence shown in SEQ ID NO: 4 and a light chain variable region consisting of the amino acid sequence shown in SEQ ID NO: 12;

(6) the antibody or the antigen-binding fragment of the antibody according to any one of (1) to (5), which consists of a heavy chain comprising the amino acid sequence at amino acid positions 20 to 466 in SEQ ID NO: 3, and a light chain comprising the amino acid sequence at amino acid positions 20 to 232 in SEQ ID NO: 11;

(7) the antibody or the antigen-binding fragment of the antibody according to any one of (1) to (5), which is a chimeric antibody;

(8) the chimeric antibody according to (7), wherein the constant region is derived from a rabbit antibody;

(9) the antibody or the antigen-binding fragment of the antibody according to any one of (1) to (5), (7) and (8), which comprises a heavy chain consisting of the amino acid sequence at amino acid positions 20 to 456 in SEQ ID NO: 19 and a light chain consisting of the amino acid sequence at amino acid positions 21 to 232 in SEQ ID NO: 21;

(10) the antibody or the antigen-binding fragment of the antibody according to any one of (1) to (5), which is of rabbit type;

(11) the antibody or the antigen-binding fragment of the antibody according to any one of (1) to (5), which is humanized;

(12) the antibody or the antigen-binding fragment of the antibody according to any one of (1) to (5) and (10), which comprises the following heavy chain (a) or (b) and light chain (c):

(a) a heavy chain consisting of the amino acid sequence at amino acid positions 20 to 456 in SEQ ID NO: 23, (b) a heavy chain consisting of the amino acid sequence at amino acid positions 20 to 456 in SEQ ID NO: 25, and (c) a light chain consisting of the amino acid sequence at amino acid positions 21 to 230 in SEQ ID NO: 27;

(13) the antibody or the antigen-binding fragment of the antibody according to any one of (1) to (5) and (10), which consists of a heavy chain comprising the amino acid sequence at amino acid positions 20 to 456 in SEQ ID NO: 23 and a light chain comprising the amino acid sequence at amino acid positions 21 to 230 in SEQ ID NO: 27;

(14) the antibody or the antigen-binding fragment of the antibody according to any one of (1) to (5) and (10), which consists of a heavy chain comprising the amino acid sequence at amino acid positions 20 to 456 in SEQ ID NO: 25 and a light chain comprising the amino acid sequence at amino acid positions 21 to 230 in SEQ ID NO: 27;

(15) the antigen-binding fragment of the antibody according to any one of (1) to (14), which is selected from the group consisting of Fab, F(ab')2, Fab' and Fv;

(16) the antibody according to any one of (1) to (14), which is scFv;

(17) a composition comprising the antibody or the antigen-binding fragment of the antibody according to any one of (1) to (16);

(18) the composition according to (17), which comprises the antibody or the antigen-binding fragment of the antibody according to any one of (1) to (16), and is used in a method for detecting or measuring GPR20 in a tissue preparation treated by paraffin embedding and then deparaffinization (hereinafter, simply referred to as a "preparation");

(19) the composition according to (17) or (18), which is used in a method for detecting or measuring GPR20 in a preparation, comprising a step of contacting the antibody or the antigen-binding fragment of the antibody according to any one of (1) to (16) with a test preparation;

(20) the composition according to (18) or (19), wherein the method for detecting or measuring GPR20 comprises a step of determining that a test preparation is positive when GPR20 has been detected or measured in the test preparation, or the expression level of GPR20 in the test preparation is equivalent to or higher than a predetermined reference, and determining that the test preparation is negative when GPR20 has not been detected or measured in the test preparation, or the expression level of GPR20 in the test preparation is equivalent to or lower than a predetermined reference;

(21) the composition according to any one of (17) to (20), which is used in a method for testing or diagnosing a GPR20-positive disease;

(22) the composition according to any one of (17) to (21), wherein the method for testing or diagnosing a GPR20-positive disease comprises: determining that a test subject originating a test preparation that has been determined to be positive in the detection or measurement of GPR20 is suitable for a method for treating or preventing the GPR20-positive disease, which method for treating or preventing the GPR20-positive disease comprises a step of administering an antibody specifically binding to GPR20 or an antigen-binding fragment of the antibody; and determining that a test subject originating a test preparation that has been determined to be negative is not suitable for the method for treating or preventing the GPR20-positive disease, which method for treating or preventing the GPR20-positive disease comprises a step of administering an antibody specifically binding to GPR20 or an antigen-binding fragment of the antibody;

(23) the composition according to (21) or (22), wherein the GPR20-positive disease is GPR20-positive cancer;

(24) the composition according to any one of (21) to (23), wherein the GPR20-positive disease is gastrointestinal stromal tumor (GIST);

(25) a pharmaceutical composition comprising an antibody specifically binding to GPR20 or an antigen-binding fragment of the antibody, the pharmaceutical composition being administered to any one of the following test subjects (a) to (c):

(a) a test subject originating a test preparation in which GPR20 has been detected or measured using the composition according to any one of (17) to (19) and (21);
(b) a test subject originating a test preparation that has been determined to be positive in the detection or measurement of GPR20 using the composition according to (20); and
(c) a test subject that has been determined to be suitable for the treatment or prevention of a GPR20-positive disease, comprising a step of administering an antibody specifically binding to GPR20 or an antigen-binding fragment of the antibody, using the composition according to (22) or (24);
(26) a method for treating a GPR20-positive disease, comprising the following steps (a) and (b):
(a) a step of detecting or measuring GPR20 in a specimen using the antibody or the antigen-binding fragment of the antibody according to any one of (1) to (16), or the composition according to any one of (17) to (19) and (21); and
(b) a step of administering an anti-GPR20 antibody or an antigen-binding fragment of the antibody to a test subject originating the specimen in which the expression of GPR20 has been detected or measured in step (a);
(27) a polynucleotide encoding the antibody or the antigen-binding fragment of the antibody according to any one of (1) to (16);
(28) a vector comprising the polynucleotide according to (27);
(29) a cell comprising the polynucleotide according to (27) or the vector according to (28); and
(30) a method for producing the antibody or the antigen-binding fragment of the antibody according to any one of (1) to (16), comprising the following steps (a) and (b):
(a) a step of culturing the cell according to (29); and
(b) a step of collecting a monoclonal antibody or an antigen-binding fragment of the antibody from the culture of step (a).

BRIEF DESCRIPTION OF DRAWINGS

FIG. 1 shows the amino acid sequence (SEQ ID NO: 3) and the nucleotide sequence (SEQ ID NO: 2) of the heavy chain of the rat anti-GPR20 antibody 04-093.

FIG. 2 shows the amino acid sequence (SEQ ID NO: 11) and the nucleotide sequence (SEQ ID NO: 10) of the light chain of the rat anti-GPR20 antibody 04-093.

FIG. 3 shows the amino acid sequences of CDRH1 to CDRH3 (SEQ ID NOs: 5 to 9) and CDRL1 to CDRL3 (SEQ ID NOs: 13 to 15) of the rat anti-GPR20 antibody 04-093.

FIG. 4 shows the amino acid sequence (SEQ ID NO: 19) of the rabbit chimeric antibody heavy chain OcHch.

FIG. 5 shows the amino acid sequence (SEQ ID NO: 21) of the rabbit chimeric antibody light chain OcLch.

FIG. 6 shows the amino acid sequence (SEQ ID NO: 23) of the rabbit type antibody heavy chain OcH01.

FIG. 7 shows the amino acid sequence (SEQ ID NO: 25) of the rabbit type antibody heavy chain OcH02.

FIG. 8 shows the amino acid sequence (SEQ ID NO: 27) of the rabbit type antibody light chain OcL01.

FIG. 9 shows flow cytometry analysis results when a culture supernatant of a hybridoma producing an anti-human GPR20 antibody was reacted with a cell line transiently expressing human GPR20. The ordinate depicts a relative value of mean fluorescence intensity (MFI) measured by flow cytometry.

FIG. 10 shows the binding activity of an anti-human GPR20 antibody against a synthetic peptide consisting of N-terminal 48 amino acids of human GPR20.

FIG. 11-1 shows images of human cells transiently-expressing GPR20 immunostained with an anti-GPR20 antibody. FIG. 11-1 shows images of staining with a rat anti-GPR20 monoclonal antibody.

FIG. 11-2 shows images of human cells transiently-expressing GPR20 immunostained with an anti-GPR20 antibody. FIG. 11-2 shows images of staining with a commercially available rabbit anti-GPR20 polyclonal antibody.

FIG. 11-3 shows images of human cells transiently-expressing GPR20 immunostained with an anti-GPR20 antibody. FIG. 11-3 shows images of staining with a commercially available rabbit anti-GPR20 polyclonal antibody.

FIG. 12-1 shows images of gastrointestinal stromal tumor GIST immunostained with a rat anti-human GPR20 antibody and a commercially available rabbit anti-GPR20 antibody. FIG. 12-1 shows images of stained stomach-derived GIST.

FIG. 12-2 shows images of gastrointestinal stromal tumor GIST immunostained with a rat anti-human GPR20 antibody and a commercially available rabbit anti-GPR20 antibody. FIG. 12-2 shows images of stained small intestine-derived GIST.

FIG. 12-3 shows images of gastrointestinal stromal tumor GIST immunostained with a rat anti-human GPR20 antibody and a commercially available rabbit anti-GPR20 antibody. FIG. 12-3 shows images of large intestine stomach-derived GIST.

FIG. 13 shows images of GPR20 stained with the rat anti-GPR20 antibody 04-093, a rabbit chimeric anti-GPR20 antibody and a rabbit type anti-GPR20 antibody, in tumor tissues derived from subcutaneously PC-3-, GIST430-, or GIST430/654-transplanted mice.

FIG. 14-1 shows images of gastrointestinal stromal tumor GIST immunostained with the rat anti-GPR20 antibody 04-093, a rabbit chimeric anti-GPR20 antibody and a rabbit type anti-GPR20 antibody. FIG. 14-1 shows images of stained stomach-derived GIST.

FIG. 14-2 shows images of gastrointestinal stromal tumor GIST immunostained with the rat anti-GPR20 antibody 04-093, a rabbit chimeric anti-GPR20 antibody and a rabbit type anti-GPR20 antibody. FIG. 14-2 shows images of stained small intestine-derived GIST.

FIG. 14-3 shows images of gastrointestinal stromal tumor GIST immunostained with the rat anti-GPR20 antibody 04-093, a rabbit chimeric anti-GPR20 antibody and a rabbit type anti-GPR20 antibody. FIG. 14-3 shows images of large intestine stomach-derived GIST.

FIG. 15 shows the binding activity of a rat anti-GPR20 monoclonal antibody against a synthetic peptide consisting of amino acid positions 1 to 48 from the N-terminus of human GPR20 and a synthetic peptide consisting of amino acid positions 30 to 48 therefrom. The abscissa depicts clone No., and the ordinate depicts the amount of the antibody bound based on chemiluminescence intensity (CPS).

FIG. 16 shows an epitope of the 04-093 antibody (SEQ ID NO: 31: amino acid sequence at positions 30 to 42 of human GPR20).

FIG. 17 is a diagram showing results of detection by Western blot using OcH1L1, OcH2L1, OcChimera, Rabbit IgG, anti-FLAG, and anti-β actin.

DESCRIPTION OF EMBODIMENTS

1. Definition

In the present invention, the term "gene" is used to mean a nucleotide comprising a nucleotide sequence encoding the amino acid sequence of a protein, or its complementary strand. The term "gene" is meant to include, for example, a polynucleotide, an oligonucleotide, DNA, mRNA, cDNA, and cRNA as the nucleotide comprising a nucleotide sequence encoding the amino acid sequence of a protein, or its complementary strand. Such a gene is a single-stranded, double-stranded, triple-stranded, or other multi-stranded nucleotide. The term "gene" is also meant to include an aggregate of DNA and RNA strands, a mixture of ribonucleotides (RNAs) and deoxyribonucleotides (DNAs) on one nucleotide strand, and a double-stranded, triple-stranded or other multi-stranded nucleotide comprising such a nucleotide strand. Examples of the "GPR20 gene" of the present invention can include DNA, mRNA, cDNA, and cRNA comprising a nucleotide sequence encoding the amino acid sequence of the GPR20 protein.

In the present invention, the term "nucleotide" is used to have the same meaning as that of the term "nucleic acid" and is also meant to include, for example, DNA, RNA, a probe, an oligonucleotide, a polynucleotide, and a primer. Such a nucleotide is a single-stranded, double-stranded, triple-stranded or other multi-stranded nucleotide. The term "nucleotide" is also meant to include an aggregate of DNA and RNA strands, a mixture of ribonucleotides (RNAs) and deoxyribonucleotides (DNAs) on one polynucleotide strand, and an aggregate of two strands or three or more strands comprising such a nucleotide strand.

In the present invention, the terms "polypeptide," "peptide," and "protein" are used to have the same meaning.

In the present invention, the term "antigen" is sometimes used to mean "immunogen".

In the present invention, the term "cell" is used to also include, for example, various cells derived from individual animals, subcultured cells, primary cultured cells, cell lines, recombinant cells, and microbial cells.

In the present invention, each antibody recognizing GPR20 is also referred to as an "anti-GPR20 antibody". Such an antibody includes a polyclonal antibody, a monoclonal antibody, a chimeric antibody, a rabbit type antibody, a humanized antibody, a human antibody, and the like.

In the present invention, the term "functional fragment of the antibody" is used to mean an antibody fragment that exerts at least a portion of the functions of the original antibody. Examples of the "functional fragment of the antibody" can include, but are not limited to, antigen-binding fragments such as Fab, F(ab')2, scFv, Fab', and single chain immunoglobulins. Such a functional fragment of the antibody may be obtained by treating a full-length molecule of the antibody protein with an enzyme such as papain or pepsin, or may be a recombinant protein produced in an appropriate host cell using a recombinant gene.

In the present invention, the "site" to which an antibody binds, i.e., the "site" recognized by an antibody, is used to mean a partial peptide or a partial conformation on an antigen that is bound or recognized by the antibody. In the present invention, such a site is also referred to as an epitope or a binding site of an antibody. Examples of the site on the GPR20 protein that is bound or recognized by the anti-GPR20 antibody of the present invention can include a partial peptide or a partial conformation on the GPR20 protein.

It is known that the heavy chain and light chain of an antibody molecule each have three complementarity determining regions (CDRs). Such a complementarity determining region is also referred to as a hypervariable domain, and is located in the variable regions of the heavy chain and light chain of an antibody. These regions have a particularly highly variable primary structure and are usually separated into three sites on the primary structure of the polypeptide chain in each of the heavy chain and light chain. In the present invention, with regard to the complementarity determining regions of an antibody, the complementarity determining regions of a heavy chain are referred to as CDRH1, CDRH2 and CDRH3, respectively, from the amino-terminal side of the amino acid sequence of the heavy chain, whereas the complementarity determining regions of a light chain are referred to as CDRL1, CDRL2 and CDRL3, respectively, from the amino-terminal side of the amino acid sequence of the light chain. These sites are located close to one another on the three-dimensional structure, and determine the specificity of the antibody to an antigen to which the antibody binds.

In the present invention, the term "antibody mutant" is used to mean a polypeptide that has an amino acid sequence derived from the amino acid sequence of the original antibody by substitution, deletion, addition and/or insertion (hereinafter, collectively referred to as a "mutation") of amino acid(s) and binds to the GPR20 protein of the present invention. The number of mutated amino acids in such an antibody mutant is 1 or 2, 1 to 3, 1 to 4, 1 to 5, 1 to 6, 1 to 7, 1 to 8, 1 to 9, 1 to 10, 1 to 12, 1 to 15, 1 to 20, 1 to 25, 1 to 30, 1 to 40 or 1 to 50. Such an antibody mutant is also included in the "antibody" of the present invention.

In the present invention, the term "several" in the phrase "one to several" is used to mean 3 to 10.

Examples of activity or properties exerted by the antibody of the present invention can include biological activities and physicochemical properties and can specifically include various biological activities, binding activity against an antigen or an epitope, stability at the time of production or preservation, and thermal stability.

In the present invention, the phrase "hybridizing under stringent conditions" is used to mean that hybridization is carried out under conditions involving hybridization at 65° C. in a solution containing 5×SSC, followed by washing at 65° C. for 20 minutes in an aqueous solution containing 2×SSC-0.1% SDS, at 65° C. for 20 minutes in an aqueous solution containing 0.5×SSC-0.1% SDS, and at 65° C. for 20 minutes in an aqueous solution containing 0.2×SSC-0.1% SDS, or under conditions equivalent thereto. SSC is an aqueous solution of 150 mM NaCl-15 mM sodium citrate, and "n×SSC" means SSC with n times the concentration.

In the present invention, the term "cytotoxicity" is used to mean that a pathologic change is caused to cells in any given way. The term not only means a direct trauma, but also means all types of structural or functional damage caused to cells, such as DNA cleavage, formation of a base dimer, chromosomal cleavage, damage to cell mitotic apparatus, and a reduction in the activities of various types of enzymes.

In the present invention, the term "cytotoxic activity" is used to mean that cytotoxicity is caused. In the present invention, the term "antibody dependent cellular cytotoxicity (ADCC) activity" is used to mean the effect or activity of damaging target cells such as tumor cells by NK cells via antibodies.

In the present invention, the term "cancer" is used to have the same meaning as that of the term "tumor".

In the present invention, the term "immunohistochemistry (IHC)" is used to mean a histological (histochemical) approach of detecting an antigen in a tissue preparation. The term "immunohistochemistry" has the same meaning as that of "immune antibody method" and also "immunostaining".

In the present invention, the term "denatured GPR20" is used to mean a GPR20 molecule in a preparation fixed in formalin. A GPR20 molecule in a preparation fixed with formalin, treated with paraffin and deparaffinized is also referred to as "denatured GPR20".

In the present invention, the term "non-denatured GPR20" is used to mean GPR20 in a sample that is not fixed in formalin. A GPR20 molecule in a preparation that is not fixed in formalin is also referred to as "non-denatured GPR20".

2. GPR20

GPR20 used in the present invention can be directly purified from the T cells or mast cells of a human or a non-human mammal (e.g., a guinea pig, a rat, a mouse, a rabbit, a pig, sheep, cattle, or a monkey) or a chicken and can then be used, or a cell membrane faction of the aforementioned cells can be prepared and can be used as GPR20. Alternatively, GPR20 can also be obtained by synthesizing it in vitro, or by allowing host cells to produce GPR20 by genetic manipulation. According to such genetic manipulation, the GPR20 protein can be obtained, specifically, by incorporating GPR20 cDNA into a vector capable of expressing the GPR20 cDNA, and then synthesizing GPR20 in a solution containing enzymes, substrate and energetic materials necessary for transcription and translation, or by transforming the host cells of other prokaryotes or eukaryotes, so as to allow them to express GPR20.

The nucleotide sequence of human GPR20 cDNA is registered in GenBank under accession No. NM_005293. The amino acid sequence of human GPR20 is also registered in GenBank under accession No. NP_005284.

The GPR20 cDNA can be obtained by, for example, the so-called PCR method in which polymerase chain reaction (hereinafter, referred to as "PCR") (Saiki, R. K., et al., Science (1988) 239, 487-491) is performed using a cDNA library from GPR20 mRNA-expressing organs or genomic DNA extracted from human cells as a template and using primers capable of specifically amplifying the GPR20 cDNA.

A polynucleotide that hybridizes under stringent conditions to a polynucleotide consisting of a nucleotide sequence complementary to a nucleotide sequence encoding human GPR20, and encodes a protein having biological activity equivalent to that of GPR20 is also included within the GPR20 cDNA. In addition, splicing variants transcribed from human GPR20 gene loci, or polynucleotides hybridizing thereto under stringent conditions, the splicing variants or the polynucleotides encoding a protein having biological activity equivalent to that of GPR20, are also included within the GPR20 cDNA.

A protein that consists of an amino acid sequence derived from the amino acid sequence of human GPR20 by the substitution, deletion, or addition of 1, 2, 3, 4 or 5 amino acids and which has biological activity equivalent to that of GPR20 is also included within the GPR20. In addition, a protein that consists of amino acid sequence encoded by a splicing variant transcribed from human GPR20 gene loci, or an amino acid sequence derived from the amino acid sequence by the substitution, deletion, or addition of 1, 2, 3, 4 or 5 amino acids and has biological activity equivalent to that of GPR20 is also included within the GPR20.

The amino acid sequence of the human GPR20 used in the present description is shown in SEQ ID NO: 1 in the sequence listing.

3. Production of Anti-GPR20 Antibody

The antibody against GPR20 of the present invention can be obtained by immunizing an animal with GPR20 or any given polypeptide selected from the amino acid sequence of GPR20 by a routine method, and then collecting and purifying an antibody produced in a living body thereof. The organism species of the antigen GPR20 is not limited to a human, and thus, an animal can also be immunized with GPR20 derived from a non-human animal such as monkey, a mouse, or a rat. In this case, an antibody applicable to the disease of a human can be selected by examining the cross-reactivity of the obtained antibody binding to the heterologous GPR20 with human GPR20. It is to be noted that the antigen GPR20 can be obtained by allowing host cells to produce the GPR20 gene according to genetic manipulation. Specifically, a vector capable of expressing the GPR20 gene is produced, and the vector is then introduced into host cells, so that the gene is expressed therein, and thereafter, the expressed GPR20 may be purified.

The antibody against GPR20 of the present invention can also be obtained by use of a DNA immunization method. The DNA immunization method is an approach which involves transfecting an animal (e.g., mouse or rat) individual with an antigen expression plasmid, and then expressing the antigen in the individual to induce immunity against the antigen. The transfection approach includes a method of directly injecting the plasmid to the muscle, a method of injecting a transfection reagent such as a liposome or polyethylenimine to the vein, an approach using a viral vector, an approach of injecting gold particles attached with the plasmid using a gene gun, a hydrodynamic method of rapidly injecting a plasmid solution in a large amount to the vein, and the like. With regard to the transfection method of injecting the expression plasmid to the muscle, a technique called in vivo electroporation, which involves applying electroporation to the intramuscular injection site of the plasmid, is known as an approach for improving an expression level (Aihara H, Miyazaki J. Nat Biotechnol. 1998 September; 16 (9): 867-70 or Mir L M, Bureau M F, Gehl J, Rangara R, Rouy D, Caillaud J M, Delaere P, Branellec D, Schwartz B, Scherman D. Proc Natl Acad Sci USA. 1999 Apr. 13; 96 (8): 4262-7). This approach further improves the expression level by treating the muscle with hyaluronidase before the intramuscular injection of the plasmid (McMahon JM1, Signori E, Wells K E, Fazio V M, Wells D J., Gene Ther. 2001 August; (16): 1264-70).

Antibody-producing cells that produce the antibody against GPR20 may be fused with myeloma cells according to a known method (e.g., Kohler and Milstein, Nature (1975) 256, p. 495-497; and Kennet, R. ed., Monoclonal Antibodies, p. 365-367, Plenum Press, N.Y. (1980)) to establish hybridomas, from which monoclonal antibodies can be obtained. Specific examples of such a method are described in International Publication Nos. WO09/48072 (published on Apr. 16, 2009) and WO10/117011 (published on Oct. 14, 2010).

Concrete examples of the rat anti-human GPR20 antibody thus established can include a 04-093 antibody. The amino acid sequence of the heavy chain of the 04-093 antibody is shown in SEQ ID NO: 3 in the sequence listing, and the nucleotide sequence encoding the heavy chain is shown in SEQ ID NO: 2 in the sequence listing. The amino acid sequence of the light chain of the 04-093 antibody is shown in SEQ ID NO: 11 in the sequence listing, and the nucleotide sequence encoding the light chain is shown in SEQ ID NO: 10 in the sequence listing. The 04-093 antibody specifically binds to a peptide comprising the amino acid sequence at amino acid positions 1 to 48 in SEQ ID NO: 1. Also, the 04-093 antibody binds to an epitope consisting of the amino acid sequence LEVPLFHLFARLD (SEQ ID NO: 31) in the peptide comprising the amino acid sequence at amino acid positions 1 to 48 in SEQ ID NO: 1.

The antibody of the present invention can be any antibody that retains all 6 CDR sequences of the 04-093 antibody and has the activity of binding to GPR20. Specifically, the heavy chain variable region of the antibody of the present invention has CDRH1 consisting of the amino acid sequence shown in SEQ ID NO: 5 or 8 (GFTFNNYWMT (based on the definition of Abm) or NYWMT (based on the definition of Kabat)), CDRH2 consisting of the amino acid sequence shown in SEQ ID NO: 6 or 9 (SITNIDGSSY (based on the definition of Abm) or SITNIDGSSYYPDSVKG (based on the definition of Kabat)), and CDRH3 consisting of the amino acid sequence shown in SEQ ID NO: 7 (GSFDY). The light chain variable region of the aforementioned antibody has CDRL1 consisting of the amino acid sequence shown in SEQ ID NO: 13 (KASQNVNKYLN), CDRL2 consisting of the amino acid sequence shown in SEQ ID NO: 14 (NTNNLQT), and CDRL3 consisting of the amino acid sequence shown in SEQ ID NO: 15 (FQHVSWLT). The amino acid sequences of these CDRs are also shown in FIG. 3.

The antibody of the present invention specifically recognizes the GPR20 protein. In other words, the preferred antibody of the present invention specifically binds to the GPR20 protein.

A certain form of the preferred antibody specifically binds to both non-denatured human GPR20 and denatured human GPR20 in a preparation fixed in formalin. More preferred examples of the antibody can include, but are not limited to, an antibody that specifically binds to both non-denatured human GPR20 and denatured human GPR20 in a preparation fixed in formalin, and does not specifically bind to the other members of the GPR family.

The antibody of the present invention also includes genetically recombinant antibodies that have been artificially modified for the purpose of reducing heterogenetic antigenicity, such as a chimeric antibody, a humanized antibody, a rabbit type antibody, and a mouse type antibody, as well as the above-described monoclonal antibody against GPR20. These antibodies can be produced by known methods.

Example of the chimeric antibody can include antibodies in which a variable region and a constant region are heterologous to each other, such as a chimeric antibody formed by conjugating the variable region of a mouse- or rat-derived antibody to a human-derived constant region (see Proc. Natl. Acad. Sci. U.S.A., 81, 6851-6855, (1984)). Other examples thereof can include a chimeric antibody formed by conjugating the variable region of a mouse- or rat-derived antibody to a rabbit-derived constant region.

Further specific examples of the rabbit chimeric antibody can include an antibody comprising a heavy chain (OcHch) comprising a heavy chain variable region derived from the 04-093 antibody and a rabbit heavy chain constant region, and a light chain (OcLch) comprising a light chain variable region derived from the 04-093 antibody and a rabbit light chain constant region. The amino acid sequence of OcHch is shown at amino acid positions 20 to 456 of SEQ ID NO: 19 in the sequence listing. The amino acid sequence of OcLch is shown at amino acid positions 21 to 232 of SEQ ID NO: 21 in the

SEQUENCE LISTING

The antibody of the present invention includes the aforementioned humanized antibody and an antibody formed by modifying the CDRs of a rabbit type antibody. These antibodies can be produced by use of known methods.

Examples of the humanized antibody can include an antibody formed by incorporating only complementarity determining regions (CDRs) into a human-derived antibody (see Nature (1986) 321, p. 522-525), and an antibody formed by transplanting the amino acid residues in some frameworks, as well as CDR sequences, into a human antibody (International Publication No. WO90/07861). Examples of the rabbit type antibody can include an antibody formed by incorporating only complementarity determining regions (CDRs) into a rabbit-derived antibody, and an antibody formed by transplanting the amino acid residues in some frameworks, as well as CDR sequences, into a rabbit antibody. The amino acid sequences of CDRs can be determined by a known method such as the definition of Kabat, the definition of Chothia, or the definition of Abm. The CDRs according to the present invention may be defined by any method.

Further specific examples of the rabbit type antibody can include rabbit type antibodies of the 04-093 antibody. More specific examples thereof can include a rabbit type antibody comprising a heavy chain (OcH01) consisting of the amino acid sequence at amino acid positions 20 to 456 of SEQ ID NO: 23 in the sequence listing or a heavy chain (OcH02) consisting of the amino acid sequence at amino acid positions 20 to 456 of SEQ ID NO: 25, and a light chain (OcL01) consisting of the amino acid sequence at amino acid positions 21 to 230 of SEQ ID NO: 27.

It is known that the lysine residue at the carboxyl terminus of the heavy chain of an antibody produced in cultured mammalian cells is deleted (Journal of Chromatography A, 705: 129-134 (1995)), and also, it is known that the two amino acid residues at the heavy chain carboxyl terminus, glycine and lysine, are deleted, and that the proline residue positioned at the carboxyl terminus is newly amidated (Analytical Biochemistry, 360: 75-83 (2007)). However, such deletion and modification of these heavy chain sequences do not have an influence on the antigen-binding activity and effector function (activation of complement, antibody-dependent cellular cytotoxicity, etc.) of an antibody. Accordingly, the present invention also includes an antibody that has undergone the aforementioned modification, and specific examples of such an antibody can include a deletion mutant comprising a deletion of 1 or 2 amino acids at the heavy chain carboxyl terminus, and a deletion mutant formed by amidating the aforementioned deletion mutant (e.g., a heavy chain in which the proline residue at the carboxyl-terminal site is amidated). However, deletion mutants involving a deletion at the carboxyl terminus of the heavy chain of the antibody according to the present invention are not limited to the above-described deletion mutants, as long as they retain antigen-binding activity and effector function. Two heavy chains constituting the antibody according to the present invention may be any one type of heavy chain selected from the group consisting of a full-length antibody and the above-described deletion mutants, or may be a combination of any two types selected from the aforementioned group. The ratio of individual deletion mutants can be influenced by the types of cultured mammalian cells that produce the antibody according to the present invention, and the culture conditions. Examples of the main ingredient of the antibody according to the present invention can include antibodies where one amino acid residue is deleted at each of the carboxyl termini of the two heavy chains.

The antibodies obtained by the above-described methods are evaluated for their binding activity against the antigen, so that a preferred antibody can be selected. One example of another indicator for comparison of the properties of antibodies can include the stability of an antibody. Differential scanning calorimetry (DSC) is a method capable of promptly and exactly measuring a thermal denaturation midpoint (Tm) serving as a good indicator for the relative structural stability of a protein. By using DSC to measure Tm values and making a comparison regarding the obtained values, differences in the thermal stability can be compared. It is known that the preservation stability of an antibody has a certain correlation with the thermal stability of the antibody (Lori Burton, et al., Pharmaceutical Development and Technology (2007) 12, p. 265-273), and thus, a preferred antibody can be selected using thermal stability as an indicator. Other examples of the indicator for selection of an antibody can include high yield in suitable host cells and low agglutination in an aqueous solution. For example, since an antibody with the highest yield does not always exhibit the highest thermal stability, it is necessary to select an antibody most suitable by comprehensively determining it based on the aforementioned indicators.

A method for obtaining a single chain immunoglobulin by linking full-length heavy and light chain sequences of an antibody via an appropriate linker is also known (Lee, H-S, et al., Molecular Immunology (1999) 36, 61-71; and Shirrmann, T. et al., mAbs (2010), 2 (1), 1-4). Such a single chain immunoglobulin can be dimerized to retain a structure and activities similar to those of the antibody, which is originally a tetramer. Also, the antibody of the present invention may be an antibody having a single heavy chain variable region and having no light chain sequence. Such an antibody, called single domain antibody (sdAb) or nanobody, is observed in camels or llamas and has been reported to retain antigen-binding ability (Muyldemans S. et al., Protein Eng. (1994) 7 (9), 1129-35; Hamers-Casterman C. et al., Nature (1993) 363 (6428) 446-8). These antibodies may be interpreted as one kind of antigen-binding fragment of the antibody according to the present invention.

Once an antibody gene is isolated, the gene can be introduced into an appropriate host to produce an antibody, using an appropriate combination of a host and an expression vector. A specific example of the antibody gene can be a combination of a gene encoding the heavy chain sequence of the antibody described in the present description and a gene encoding the light chain sequence of the antibody described therein. Upon transformation of host cells, such a heavy chain sequence gene and a light chain sequence gene may be inserted into a single expression vector, or these genes may instead each be inserted into different expression vectors. When eukaryotic cells are used as hosts, animal cells, plant cells or eukaryotic microorganisms can be used. Examples of the animal cells can include (1) mammalian cells such as COS cells which are monkey cells (Gluzman, Y., Cell (1981) 23, p. 175-182, ATCC CRL-1650), mouse fibroblasts NIH3T3 (ATCC No. CRL -1658), and a dihydrofolate reductase-deficient cell line of Chinese hamster ovary cells (CHO cells, ATCC CCL-61) (Urlaub, G. and Chasin, L. A. Proc. Natl. Acad. Sci. U.S.A. (1980) 77, p. 4126-4220). When prokaryotic cells are used as hosts, *Escherichia coli* or *Bacillus subtilis* can be used, for example. An antibody gene of interest is introduced into these cells for transformation, and the transformed cells are then cultured in vitro to obtain an antibody. In the aforementioned culture method, there are cases where yield is different depending on the sequence of the antibody, and thus, it is possible to select an antibody, which is easily produced as a medicament, from antibodies having equivalent binding activity, using the yield as an indicator.

Examples of the isotype of the antibody of the present invention can include, but are not limited to, IgG (IgG1, IgG2, IgG3, and IgG4), IgM, IgA (IgA1 and IgA2), IgD and IgE, preferably IgG or IgM, more preferably IgG1 or IgG2.

The antibody of the present invention may be an antigen-binding fragment of an antibody having the antigen-binding moiety of the antibody, or a modification thereof. A fragment of the antibody can be obtained by treating the antibody with a proteolytic enzyme such as papain or pepsin, or by modifying the antibody gene by a genetic engineering approach and allowing appropriate cultured cells to express the gene. Among such antibody fragments, a fragment that retains all or a portion of the functions of the full-length antibody molecule can be referred to as an antigen-binding fragment of the antibody. Examples of the functions of the antibody can generally include antigen-binding activity, activity of neutralizing the activity of an antigen, activity of enhancing the activity of an antigen, antibody-dependent cellular cytotoxic activity, complement-dependent cytotoxic activity, and complement-dependent cellular cytotoxic activity. The function retained by the antigen-binding fragment of the antibody according to the present invention is binding activity against GPR20.

Example of the fragment of the antibody can include Fab, F(ab')2, Fv, single chain Fv (scFv) comprising heavy chain and light chain Fv fragments linked via an appropriate linker, diabody (diabodies), linear antibodies and multispecific antibodies formed from antibody fragments. Also, Fab', which is a monovalent fragment of antibody variable regions obtained by treating F(ab')2 under reducing conditions, is included in the fragment of the antibody.

The antibody of the present invention may be a multispecific antibody having specificity for at least two different antigens. Such a molecule usually binds to two types of antigens (i.e., bispecific antibody). The "multispecific antibody" according to the present invention includes an antibody having specificity for more (e.g., three types of) antigens.

The multispecific antibody of the present invention may be an antibody consisting of a full length antibody, or a fragment of such an antibody (e.g., a F(ab')2 bispecific antibody). The bispecific antibody may be produced by connecting the heavy chains and light chains (HL pairs) of two types of antibodies, or may be produced by fusing hybridomas producing different monoclonal antibodies to produce bispecific antibody-producing fusion cells (Millstein et al., Nature (1983) 305, p. 537-539).

The antibody of the present invention may be a single chain antibody (also referred to as scFv). The single chain antibody is obtained by linking an antibody heavy chain variable region and light chain variable region via a polypeptide linker (Pluckthun, The Pharmacology of Monoclonal Antibodies, 113 (Rosenberg and Moore ed., Springer Verlag, New York, p. 269-315 (1994); and Nature Biotechnology (2005), 23, p. 1126-1136). Alternatively, a biscFv fragment, which is produced by linking two scFvs via a polypeptide linker, may be used as the bispecific antibody.

A method for producing a single chain antibody is well known in the art (see e.g., U.S. Pat. Nos. 4,946,778, 5,260, 203, 5,091,513, and 5,455,030). In this scFv, a heavy chain variable region and a light chain variable region are linked via a linker that does not form a conjugate, preferably via a polypeptide linker (Huston, J. S. et al., Proc. Natl. Acad. Sci. U.S.A. (1988), 85, 5879-5883). The heavy chain variable region and the light chain variable region in the scFv may be derived from the same antibody or may be derived from different antibodies. For example, any given single chain peptide consisting of 12 to 19 residues is used as the polypeptide linker that links these variable regions.

In order to obtain scFv-encoding DNA of the sequences of DNA encoding the heavy chain or heavy chain variable region of the antibody and DNA encoding the light chain or light chain variable region thereof, each DNA portion encoding the entire or desired amino acid sequence is used as a template and amplified by PCR using a primer pair flanking both ends of the template. Subsequently, DNA encoding the polypeptide linker moiety is further amplified in combination with a primer pair flanking both ends of the DNA so that the resulting fragment can be linked at its ends to the heavy and light chain DNAs.

Once the scFv-encoding DNA is produced, an expression vector containing the DNA, and a host transformed with the expression vector can be obtained according to routine methods, and scFv can be obtained according to a routine method using the host. These antibody fragments can be produced in hosts by obtaining and expressing their genes in the same manner as above.

The antibody of the present invention may be multimerized to enhance its affinity for the antigen. In this case, antibodies of the same type may be multimerized, or a plurality of antibodies recognizing a plurality of epitopes, respectively, of the same antigen may be multimerized. Examples of methods for multimerizing these antibodies can include the binding of two scFvs to an IgG CH3 domain, the binding of these to streptavidin, and the introduction of a helix-turn-helix motif.

The antibody of the present invention may be a polyclonal antibody, which is a mixture of plural types of anti-GPR20 antibodies differing in amino acid sequence. One example of the polyclonal antibody can include a mixture of plural types of antibodies differing in CDRs. Such a polyclonal antibody can be an antibody purified from a culture obtained by culturing a mixture of cells producing different antibodies (see WO2004/061104).

Antibodies conjugated with various molecules such as polyethylene glycol (PEG) can also be used as modifications of the antibody.

The antibody of the present invention may be a conjugate formed from the antibody and an additional drug (immunoconjugate). Examples of such an antibody can include conjugates of the antibody with a radioactive substance or a compound having a pharmacological effect (Nature Biotechnology (2005) 23, p. 1137-1146).

The obtained antibody can be purified to a homogenous state. For separation and purification of the antibody, separation and purification methods used for ordinary proteins may be used. For example, column chromatography, filtration, ultrafiltration, salting-out, dialysis, preparative polyacrylamide gel electrophoresis, and isoelectric focusing are appropriately selected and combined with one another, so that the antibody can be separated and purified (Strategies for Protein Purification and Characterization: A Laboratory Course Manual, Daniel R. Marshak et al. eds., Cold Spring Harbor Laboratory Press (1996); and Antibodies: A Laboratory Manual. Ed Harlow and David Lane, Cold Spring Harbor Laboratory (1988)), though examples of the separation and purification methods are not limited thereto.

Examples of the chromatography can include affinity chromatography, ion exchange chromatography, hydrophobic chromatography, gel filtration chromatography, reverse phase chromatography, and absorption chromatography.

These chromatographic techniques can be carried out using liquid chromatography such as HPLC or FPLC. Examples of the column used in the affinity chromatography can include a Protein A column and a Protein G column. Examples of the column involving the use of Protein A can include Hyper D, POROS, and Sepharose F. F. (Pharmacia). Also, using an antigen-immobilized carrier, the antibody can be purified by utilizing the binding activity of the antibody to the antigen.

4. Pharmaceutical Composition

The present invention provides a pharmaceutical composition comprising the anti-GPR20 antibody or the functional fragment thereof, or the modification of the antibody or the functional fragment.

The pharmaceutical composition of the present invention is useful in the treatment or prevention of various diseases that are initiated or exacerbated by abnormal or increased GPR20 signals due to overexpression of GPR20 or its ligand or GPR20 mutations or gene amplification (hereinafter, referred to as "GPR20-related diseases"), particularly, various cancers.

Examples of causes of the initiation or exacerbation of such cancers to be treated or prevented can include single nucleotide polymorphism (SNP) in the GPR20 gene, high expression of GPR20, missense mutations that constitutively activate GPR20, amplification or overexpression of the GPR20 gene, and switching of GPR20 isoforms.

Examples of such a cancer type can include gastrointestinal stromal tumor (GIST) and can preferably include gastrointestinal stromal tumor (GIST) expressing the GPR20 protein.

In the present invention, the treatment or prevention of a disease includes, but is not limited to, the prevention of the onset of the disease, preferably the disease in an individual expressing the GPR20 protein, the suppression or inhibition of exacerbation or progression thereof, the alleviation of one or two or more symptoms exhibited by an individual affected with the disease, the suppression or remission of exacerbation or progression thereof, the treatment or prevention of a secondary disease, etc.

The pharmaceutical composition of the present invention can contain a therapeutically or prophylactically effective amount of the anti-GPR20 antibody or the functional fragment of the antibody and a pharmaceutically acceptable diluent, carrier, solubilizer, emulsifier, preservative, and/or additive.

The "therapeutically or prophylactically effective amount" means an amount that has therapeutic or prophylactic effects on a particular disease by means of a particular dosage form and administration route and has the same meaning as that of "pharmacologically effective amount".

The pharmaceutical composition of the present invention can contain materials for changing, maintaining, or retaining pH, osmotic pressure, viscosity, transparency, color, tonicity, sterility, or the stability, solubility, sustained release, absorbability, permeability, dosage form, strength, properties, shape, etc., of the composition or the antibody contained therein (hereinafter, referred to as "pharmaceutical materials"). The pharmaceutical materials are not particularly limited as long as the materials are pharmacologically acceptable. For example, non-toxic or low toxicity is a property preferably possessed by these pharmaceutical materials.

Examples of pharmaceutical materials can include amino acids, antimicrobial agents, antioxidants, buffers, fillers, chelating agents, complexing agents, bulking agents, monosaccharides, disaccharides, hydrocarbons, coloring agents, corrigents, diluents, emulsifiers, hydrophilic polymers, antiseptics, solvents, sugar alcohols, suspending agents, surfactants, stability enhancers, elasticity enhancers, transport agents, diluents, excipients, and/or pharmaceutical additives. The amount of these materials added is 0.001 to 1000 times, preferably 0.01 to 100 times, and more preferably 0.1 to 10 times the weight of the anti-GPR20 antibody or the functional fragment thereof, or the modification of the antibody or the functional fragment.

An immunoliposome comprising the anti-GPR20 antibody or the functional fragment thereof, or the modification of the antibody or the functional fragment encapsulated in a liposome, or a pharmaceutical composition containing an antibody modification comprising the antibody conjugated with a liposome (U.S. Pat. No. 6,214,388, etc.) are also included in the pharmaceutical composition of the present invention.

The excipients or carriers are not particularly limited as long as they are liquid or solid materials usually used in injectable water, saline, artificial cerebrospinal fluids, and other preparations for oral or parenteral administration. Examples of saline can include neutral saline and serum albumin-containing saline.

Examples of the buffers can include a Tris buffer adjusted to bring the final pH of the pharmaceutical composition to 7.0 to 8.5, an acetate buffer adjusted to bring the final pH to 4.0 to 5.5, a citrate buffer adjusted to bring the final pH to 5.0 to 8.0, and a histidine buffer adjusted to bring the final pH to 5.0 to 8.0.

The pharmaceutical composition of the present invention is a solid, a liquid, a suspension, or the like. Another example of the pharmaceutical composition of the present invention can include a freeze-dried formulation. The freeze-dried formulation can be formed using an excipient such as sucrose.

The administration route of the pharmaceutical composition of the present invention may be any of enteral administration, local administration, and parenteral administration. Examples thereof can include intravenous administration, intra-arterial administration, intramuscular administration, intradermal administration, subcutaneous administration, intraperitoneal administration, transdermal administration, intraosseous administration, and intraarticular administration.

The composition of the pharmaceutical composition can be determined according to the administration method, the binding affinity of the antibody for the GPR20 protein, etc. As the affinity of the anti-GPR20 antibody of the present invention or the functional fragment thereof, or the modification of the antibody or the functional fragment increases (i.e., the Kd value is lowered), the pharmaceutical composition can exert medicinal effects, even if the applied dose thereof is decreased.

The dose of the anti-GPR20 antibody of the present invention is not limited as long as the dose is a pharmacologically effective amount. The dose can be appropriately determined on the basis of the species of the individual, the type of disease, symptoms, sex, age, pre-existing conditions, the binding affinity of the antibody for the GPR20 protein or its biological activity, and other factors. A dose of usually 0.01 to 1000 mg/kg, preferably 0.1 to 100 mg/kg, can be administered once per 1 to 180 days or two or three or more times daily.

Examples of the form of the pharmaceutical composition can include injections (including freeze-dried formulations and drops), suppositories, transnasal absorption formulations, transdermal absorption formulations, sublingual formulations, capsules, tablets, ointments, granules, aerosols, pills, powders, suspensions, emulsions, eye drops, and biological implant formulations.

The pharmaceutical composition comprising the anti-GPR20 antibody or the functional fragment thereof, or the modification of the antibody or the functional fragment as an active ingredient can be administered simultaneously with or separately from an additional medicament. For example, the pharmaceutical composition comprising the anti-GPR20 antibody or the functional fragment of the antibody as an active ingredient may be administered after administration of the additional medicament, or the additional medicament may be administered after administration of the pharmaceutical composition. Alternatively, the pharmaceutical composition and the additional medicament may be administered simultaneously. Examples of the additional medicament can include various anticancer agents such as chemotherapeutics and radiation therapy. These cases are collectively referred to as the "combined use with an additional medicament" of the antibody of the present invention. A pharmaceutical composition comprising the antibody of the present invention or the functional fragment thereof, or the modification of the antibody or the functional fragment as well as an additional drug is also included in the present invention.

The present invention also provides a method for treating or preventing a GPR20-related disease such as cancer, use of the antibody of the present invention for preparing a pharmaceutical composition for the treatment or prevention of the disease, and use of the antibody of the present invention for the treatment or prevention of the disease. A kit for treatment or prevention comprising the antibody of the present invention is also included in the present invention.

5. Composition for Diagnosis

The present invention provides a composition for testing or for diagnosis (hereinafter, referred to as a "composition for diagnosis") comprising the anti-GPR20 antibody or the functional fragment thereof, or the modification of the antibody or the functional fragment.

The composition for diagnosis of the present invention is useful in the testing or diagnosis of GPR20-related diseases such as cancer and gastrointestinal stromal tumor (GIST), or of GPR20 expression. In the present invention, the testing or the diagnosis includes, for example, the determination or measurement of a risk of developing a disease, the determination of the presence or absence of a disease, the measurement of the degree of progression or exacerbation of a disease, the measurement or determination of the effect of drug therapy using the pharmaceutical composition comprising the anti-GPR20 antibody or the like, the measurement or determination of the effect of therapy other than drug therapy, the measurement of a risk of recurrence of a disease, and the determination of the presence or absence of recurrence of a disease, though the testing or the diagnosis according to the present invention is not limited thereto.

The composition for diagnosis of the present invention is useful in the identification of a recipient individual for the anti-GPR20 antibody of the present invention or the functional fragment thereof, or the modification of the antibody or the functional fragment, a composition comprising the same, or a pharmaceutical composition comprising the same.

The composition for diagnosis can contain a pH buffer, an osmoregulator, salts, a stabilizer, an antiseptic, a color developer, a sensitizer, an aggregation inhibitor, and the like.

The present invention provides a method for testing or diagnosing a GPR20-related disease such as cancer, use of the antibody of the present invention for preparing a composition for diagnosis of the disease, and use of the antibody of the present invention for testing or diagnosing the disease. A kit for testing or diagnosis comprising the antibody of the present invention is also included in the present invention.

The testing or diagnosis method using the composition for diagnosis of the present invention is desirably sandwich ELISA. Any usual detection method using antibodies, such as ELISA, RIA, ELISPOT (enzyme-linked immunospot), dot blot, Ouchterlony test, CIE (counter immunoelectrophoresis), CLIA (chemiluminescent immunoassay), or FCM (flow cytometry), may be used. The antibodies can be labeled by a method using biotin or by a labeling method feasible in biochemical analysis using a luminophore or a fluorophore such as HRP, alkaline phosphatase, FITC, or ALEXA, a label such as a radioisotope, or the like. A chromogenic substrate such as TMB (3,3',5,5'-tetramethylbenzidine), BCIP (5-bromo-4-chloro-3-indolyl phosphate), p-NPP (p-nitrophenyl phosphate), OPD (o-phenylenediamine), ABTS (3-ethylbenzothiazoline-6-sulfonic acid), and SuperSignal ELISA Pico Chemiluminescent Substrate (Thermo Fisher Scientific Inc.), a fluorescent substrate QuantaBlu® Fluorogenic Peroxidase Substrate (Thermo Fisher Scientific Inc.), and a chemiluminescent substrate can be used in detection using enzymatic labeling. Samples derived from humans or non-human animals as well as artificially treated samples such as recombinant proteins can be subjected to this assay. Examples of test samples derived from individual organisms can include, but are not limited to, blood, synovial fluids, ascites, lymph, cerebrospinal fluids, tissue homogenate supernatants, and tissue sections.

The sandwich ELISA kit for testing or diagnosis comprising the antibody of the present invention may comprise a control (standard solution of a GPR20-derived peptide), a coloring reagent, a buffer solution for dilution, an antibody for solid phase, an antibody for detection, and a washing solution, and the like. For example, an absorbance, fluorescence, luminescence, or RI (radioisotope) method is preferably applied to a method for measuring the amount of the antibody bound to the antigen. An absorbance plate reader, a fluorescence plate reader, a luminescence plate reader, an RI liquid scintillation counter, or the like is preferably used in the measurement.

The antibody of the present invention can be used in the aforementioned immunohistological test as well as Western blot or dot blot which involves preparing a solubilized protein according to a routine method from cells, a tissue or an organ in a sample, or a portion thereof, and reacting a labeled antibody with the solubilized protein to confirm the presence or absence of GPR20 in the solubilized protein. The sample to be tested includes, but is not limited to, solubilized proteins prepared from exosomes or the like secreted from various cells including cells contained in body fluids such as blood, blood circulating tumor cells, and cancer cells.

The present invention provides an antibody useful for immunohistochemistry (IHC) analysis or a functional fragment thereof, and a modification of the antibody or the functional fragment, and a composition comprising the same. Such a composition is also included in the "composition for diagnosis" of the present invention.

The immunohistochemistry is not particularly limited as long as this approach involves reacting a tissue section with an antigen-binding antibody (primary antibody) and detecting the primary antibody bound with the antigen. The tissue section is preferably treated by paraffin embedding after formalin fixation. The tissue section thus embedded in paraffin is sliced, and then deparaffinized, followed by antigen retrieval treatment and nonspecific reaction inhibition treatment. Examples of methods for the antigen retrieval treatment can include heat treatment and enzymatic treatment using protease or the like. Heat treatment is preferred. The heat treatment is usually performed under preferred conditions involving a temperature of 90 to 110° C., pH 8 to 10, and a treatment time in the range of from 20 to 60 minutes. A Tris-EDTA buffer solution (e.g., a 10 mM Tris buffer solution containing 1 mM EDTA) or the like can be used in pH adjustment. A method for inactivating an endogenous enzyme having the same or similar catalytic activity as that of an enzyme used in color development is usually used as the nonspecific reaction inhibition treatment. For color development through peroxidase reaction, endogenous peroxidase present in tissues is preferably inhibited in advance using $H_2O_2$ or the like. A solvent such as water or methanol can be used for $H_2O_2$. The concentration of $H_2O_2$ is 0.1 to 3%, preferably 0.3 to 3%. The $H_2O_2$ solution can be supplemented with sodium azide. Also, a blocking method using serum or casein can also be used as the nonspecific reaction inhibition treatment. Tissues can be treated with serum or casein before the primary antibody reaction. Alternatively, serum or casein may be contained in a solvent for diluting the primary antibody.

The reaction conditions for the primary antibody are not particularly limited and involve a temperature of 4 to 50° C., preferably 20 to 37° C., and more preferably 24° C. The reaction time is 5 minutes to all night and all day, preferably 10 minutes to 4 hours, and more preferably 30 minutes to 1 hour.

Preferably, an antibody (secondary antibody) capable of being visualized and binding to the primary antibody can be used in the detection of the primary antibody. Three or more reactions may be performed using an antibody (tertiary antibody) binding to the secondary antibody itself. The secondary antibody or the tertiary antibody can be preferably visualized by use of a method involving conjugating an enzyme such as peroxidase or alkaline phosphatase to these antibodies, or adding biotin or the like to these antibodies and binding to streptavidin or the like conjugated with the enzyme, followed by reaction with a chromogenic substrate appropriate for the enzyme. Examples of the method for conjugating an enzyme to the secondary antibody or the tertiary antibody can include a method using a reagent comprising a dextrin polymer or an amino acid polymer to which many molecules of the enzyme and the secondary antibody are attached (polymer method). A chromogenic substrate such as DAB can be used in a method for reacting a biotinylated secondary antibody with peroxidase-labeled streptavidin (LSAB method). Alternatively, a secondary antibody labeled with a fluorescent dye or the like may be used. When a sample is treated with the fluorescently labeled secondary antibody, positive cells are detected under a fluorescence microscope after the treatment.

A smear method involves separating excised cells into cellular components and fluid components by application to glass or centrifugation in a centrifuge, and immunostaining the cellular components. Specifically, the cellular components can be applied onto a glass slide, fixed in an ethanol solution, a 10% formalin solution, or the like, and then immunostained in the same way as in the tissue section.

A freeze embedding method involves embedding excised tissues in an OCT compound or the like, then rapidly freezing the embedded tissues in liquid nitrogen or the like, and slicing the frozen tissues using a cryostat to prepare a slide preparation. This preparation can be fixed in a 10% formalin solution, an ethanol solution, or the like and then immunostained in the same way as in the tissue section.

The immunohistochemical procedure can be performed automatically using an immunological apparatus programmed with a reaction solution, reaction conditions, the number of washing runs, etc.

For diagnostic imaging, the antibody is labeled with a pharmaceutically acceptable radionuclide or luminescent material and administered to a test subject, and images can be taken using a diagnostic imaging technique such as PET/CT to determine or test the presence of GPR20.

The antibody or the functional fragment thereof, or the modification of the antibody or the functional fragment contained in the composition for diagnosis of the present invention is preferably an antibody binding to GPR20, i.e., an antibody having GPR20 selectivity or a functional fragment thereof, or a modification of the antibody or the functional fragment.

Examples of the antibody having human GPR20 selectivity can include an antibody comprising a heavy chain comprising the heavy chain CDRH1, CDRH2 and CDRH3 of the rat 04-093 antibody, and a light chain comprising the light chain CDRL1, CDRL2 and CDRL3 thereof, an antibody comprising the heavy chain variable region and light chain variable region of the rat 04-093 antibody, and an antibody comprising the heavy chain and light chain of the rat 04-093 antibody. Examples of such an antibody can include, but are not limited to, the rat 04-093 antibody, chimeric antibodies derived from the 04-093 antibody, rabbit type antibodies derived from the 04-093 antibody, and humanized antibodies derived from the 04-093 antibody.

In one preferred embodiment of the present invention, the composition for diagnosis is for GPR20 detection or measurement.

The present invention provides a method for detecting or measuring human GPR20 in a test sample.

The aforementioned detection or measurement method can employ the composition for diagnosis of the present invention. Such a measurement method and a composition for diagnosis are also included for the diagnosis or testing of human GPR20-positive cancer, preferably gastrointestinal stromal tumor, in the present invention.

The present invention also includes a method for identifying an individual (patient) to whom a pharmaceutical composition targeting GPR20 can be administered. In this identification method, human GPR20 is measured in a sample derived from the individual. When human GPR20 has been detected in the sample, or human GPR20 has been detected in an amount larger than that of human GPR20 detected in a sample derived from a healthy individual, it is determined that the individual is positive. Thus, the individual can be identified as an individual to whom a pharmaceutical composition targeting GPR20 can be administered.

In order to identify the individual to whom a pharmaceutical composition targeting GPR20 is administered, the expression of GPR20 in a sample derived from the test subject can be confirmed, and, in addition, the expression level of GPR20 or a staining ratio or staining intensity of immunostaining can be further used as an index. One example of such a method can include a method involving establishing scores of 0 to 3 shown in Table 1 according to the degree of staining in immunostaining with the anti-GPR20 antibody, and identifying a test subject with a score of 1 or higher, 2 or higher or 3 or higher as a patient to whom a pharmaceutical composition targeting GPR20 is administered.

TABLE 1

| Score | Criteria |
|---|---|
| 0 | Not stained, less than 30% tumor cells are stained with a given level of intensity, or only the tumor stroma is stained |
| 1 | 30% or more tumor cells are slightly or weakly stained at their membrane moieties<br>Less than 30% tumor cells are moderately or strongly stained (using 10× or more objective lens) |
| 2 | 30% or more tumor cells are moderately or strongly stained at their membrane moieties<br>Less than 30% tumor cells are strongly stained (using 10× objective lens) |
| 3 | 30% or more tumor cells are strongly stained at their membrane moieties (using 4× objective lens) |

The aforementioned method can employ the composition for diagnosis of the present invention.

In a preferred form of such an identification method, the individual can be used to determine that the individual has cancer, preferably gastrointestinal stromal tumor, or has the risk of developing it.

In one embodiment, the pharmaceutical composition of the present invention can be administered to an individual that has been determined to be positive in such an identification method.

6. Reagent

The antibody of the present invention or the antigen-binding fragment thereof, or the modification of the antibody or the antigen-binding fragment is also useful as a reagent. Such a reagent is used for the aforementioned testing or diagnosis, for research and for other purposes.

EXAMPLES

Hereinafter, the present invention will be specifically described in the following examples. Furthermore, these examples should not be construed in a limited manner by any means. It is to be noted that, in the following examples, unless otherwise specified, individual operations regarding genetic manipulation have been carried out according to the method described in "Molecular Cloning" (Sambrook, J., Fritsch, E. F. and Maniatis, T., published by Cold Spring Harbor Laboratory Press in 1989), or when commercially available reagents or kits have been used, the examples have been carried out in accordance with the instructions included in the commercially available products. In the present description, reagents, solvents and starting materials are readily available from commercially available sources, unless otherwise specified.

Example 1: Production of Rat Anti-Human GPR20 Antibody

1)-1 Construction of Human GPR20 Expression Vector

Using human brain-derived cDNA as a template, cDNA encoding human GPR20 protein (NP_005284) was amplified by PCR according to a method known to a person skilled in the art, and the amplification product was incorporated into a vector for mammalian expression to produce human GPR20 expression vector pcDNA3.1-hGPR20. The amino acid sequence of the human GPR20 is shown in SEQ ID NO: 1 in the sequence listing. An EndoFree Plasmid Giga Kit (Qiagen N.V.) was used for mass production of pcDNA3.1-hGPR20 plasmid DNA.

1)-2 Immunization of Rats

For immunization, 6-week-old WKY/Izm female rats (Japan SLC, Inc.) were used. First, the lower limbs of each rat were pre-treated with Hyaluronidase (Sigma-Aldrich Co. LLC), and thereafter, the human GPR20 expression vector pcDNA3.1-hGPR20 was intramuscularly injected into the same sites. Subsequently, employing ECM830 (BTX), in vivo electroporation was carried out on the same sites using a two-needle electrode. Once every two weeks, the same in vivo electroporation was repeated. On the 79th day, lymph nodes were collected from the rat, and then used in production of hybridomas.

1)-3 Production of Hybridomas

The lymph node cells were fused with mouse myeloma SP2/0-ag14 cells by way of electrical cell fusion, using a Hybrimune Hybridoma Production System (Cyto Pulse Sciences, Inc.), and the cells were then suspended and diluted with ClonaCell-HY Selection Medium D (StemCell Technologies Inc.), and then cultured under conditions of 37° C. and 5% $CO_2$. Individual hybridoma colonies that appeared in the culture were collected as monoclonal hybridomas, then suspended in ClonaCell-HY Selection Medium E (StemCell Technologies Inc.), and then cultured under conditions of 37° C. and 5% $CO_2$. After moderate proliferation of cells, frozen stocks of individual hybridoma cells were produced, while a culture supernatant was collected from each hybridoma, and used to screen for anti-GPR20 antibody-producing hybridomas.

1)-4 Antibody-Producing Hybridoma Screening According to Cell-ELISA Method

1)-4-1 Preparation of Antigen Gene-Expressing Cells for Use in Cell-ELISA

293α cells (a stable expression cell line derived from HEK293 cells expressing integrin αv and integrin β3) were prepared at $5\times10^6$ cells/10 mL in DMEM medium supplemented with 10% FBS. In accordance with transduction procedures for using Lipofectamine 2000 (Invitrogen Corp.), DNA of pcDNA3.1-hGPR20 or pcDNA3.1 as a negative control was introduced into the 293α cells, and the cells were dispensed in an amount of 100 μL/well to a 96-well plate (Corning Inc.). Thereafter, the cells were cultured under conditions of 37° C. and 5% $CO_2$ in DMEM medium supplemented with 10% FBS for 24 to 27 hours. The obtained transfected cells were used for Cell-ELISA in an adhesive state.

1)-4-2 Cell-ELISA

The culture supernatant of the 293α cells transfected with the expression vector prepared in Example 1)-4-1 was removed, and the culture supernatant from each hybridoma was then added to the 293α cells transfected either with pcDNA3.1-hGPR20 or pcDNA3.1. The cells were left standing at 4° C. for 1 hour. The cells in the wells were washed once with PBS (+) supplemented with 5% FBS, and thereafter, Anti-Rat IgG-Peroxidase antibody produced in rabbit (Sigma-Aldrich Co. LLC) that had been 500-fold diluted with PBS (+) supplemented with 5% FBS was added to the wells. The cells were left standing at 4° C. for 1 hour. The cells in the wells were washed three times with PBS (+) supplemented with 5% FBS, and thereafter, OPD coloring solution (which had been prepared by dissolving o-phenylenediamine dihydrochloride (Wako Pure Chemical Industries, Ltd.) and $H_2O_2$ in an OPD solution (0.05 M trisodium citrate, 0.1 M disodium hydrogen phosphate 12-water; pH 4.5), so that the substances became 0.4 mg/ml and 0.6% (v/v), respectively) was added in an amount of 100 μL/well to the wells. A coloring reaction was carried out with occasional stirring. Thereafter, 1 M HCl was added to the plate (100 μL/well) to terminate the coloring reaction, followed by measurement of the absorbance at 490 nm using a plate reader (ENVISION: PerkinElmer, Inc.). In order to select hybridomas that produce an antibody specifically binding to human GPR20 expressed on the surface of a cell membrane, hybridomas that produced a culture supernatant exhibiting higher absorbance in the 293α cells transfected with the pcDNA3.1-hGPR20 expression vector than that in the 293α cells transfected with the control pcDNA3.1 were selected as anti-human GPR20 antibody production-positive hybridomas.

1)-5 Human GPR20-Binding Antibody Screening According to Flow Cytometry

1)-5-1 Preparation of Antigen Gene-Expressing Cells for Use in Flow Cytometry Analysis 293T cells were seeded in a 225-cm² flask (manufactured by Sumitomo Bakelite Co., Ltd.) at $5\times10^4$ cells/cm², and the cells were then cultured overnight under conditions of 37° C. and 5% $CO_2$ in DMEM medium supplemented with 10% FBS. On the next day, pcDNA3.1-hGPR20 or pcDNA3.1 as a negative control was introduced into the 293T cells using Lipofectamine 2000, and the cells were further cultured overnight under conditions of 37° C. and 5% $CO_2$. On the next day, the 293T cells transfected with each expression vector were treated with TrypLE Express (manufactured by Life Technologies Corp.), and the cells were washed with DMEM supplemented with 10% FBS, and then suspended in PBS supplemented with 5% FBS. The obtained cell suspension was used in flow cytometry analysis.

1)-5-2 Flow Cytometry Analysis

The binding specificity to human GPR20 of an antibody produced from hybridomas that had been determined to be positive by Cell-ELISA in Example 1)-4-2 was further confirmed by flow cytometry. The suspension of the transiently expressing 293T cells prepared in Example 1)-5-1 was centrifuged, and a supernatant was then removed. Thereafter, the cells were suspended by the addition of the culture supernatant from each hybridoma. The cells were left standing at 4° C. for 1 hour. The cells were washed twice with PBS supplemented with 5% FBS, and thereafter, the cells were suspended by the addition of Anti-Rat IgG FITC conjugate (manufactured by Sigma-Aldrich Co. LLC) that had been 500-fold diluted with PBS supplemented with 5% FBS. The cells were left standing at 4° C. for 1 hour. The cells were washed twice with PBS supplemented with 5% FBS, and then re-suspended in PBS supplemented with 5% FBS and 2 μg/ml 7-aminoactinomycin D (manufactured by Molecular Probes, Inc.), followed by detection using a flow cytometer (FC500; manufactured by Beckman Coulter, Inc.). The data was analyzed using Flowjo (manufactured by Tree Star, Inc.). After dead cells were removed from analysis by gating out 7-aminoactinomycin D-positive cells, a histogram of the FITC fluorescence intensity of live cells was generated. Hybridomas producing human GPR20-binding antibodies (178 clones) were selected based on results where the histogram for the antibody shifted to the strong fluorescence intensity side in the 293T cells transfected with pcDNA3.1-hGPR20 compared with the 293T cells transfected with the control pcDNA3.1. FIG. 9 shows results for clone Nos. 04-093, 13-001, 13-006, 13-010, 13-040 and 13-046, and the negative control without the addition of the primary antibody (w/o 1st Ab) as examples of antibodies specifically binding to human GPR20. The abscissa of FIG.

9 depicts clone No., and the ordinate thereof depicts the amount of the antibody bound based on MFI (mean fluorescence intensity).

1)-6 Screening by Peptide-ELISA

Binding activity against N-terminal 48 amino acids of human GPR20 was evaluated by peptide-ELISA. NeutrAvidin (Pierce/Thermo Fisher Scientific Inc.) diluted into 1 µg/mL with PBS was added at 100 µL/well to 96-well Maxisorp plate (Nunc), and the plate was left standing overnight at 4° C. The solution was removed, and the plate was washed three times with 300 µL/well of PBS containing 0.05% Tween 20 (hereinafter, referred to as PBST). Then, C-terminally biotinylated synthetic peptide 1 consisting of amino acids at positions 1 to 48 (SEQ ID NO: 29) from the N-terminus of human GPR20 was dissolved at 10 nM in PBS, and this solution was added at 100 µL/well. The plate was left standing at room temperature for 1 hour. Likewise, a plate supplemented with a C-terminally biotinylated synthetic peptide having a sequence different from the amino acid sequence of GPR20 was prepared as a negative control and then treated in the same way as in the aforementioned plate. The solution was removed from the plate, and each well was washed three times with PBST. Then, PBS containing 1% BSA was added at 100 µL/well, and the plate was left standing overnight at room temperature. The solution was removed, and each well was washed three times with PBST. Then, the culture supernatant from each anti-human GPR20 antibody-producing hybridoma 2-fold diluted with PBS containing 1% BSA was added at 100 µL/well, and the plate was left standing at room temperature for 1 hour. The solution was removed, and each well was washed three times with PBST. Then, Anti-Rat IgG-Peroxidase antibody produced in rabbit (Sigma-Aldrich Co. LLC) 500-fold diluted with PBS was added at 100 µL/well, and the plate was left standing at room temperature for 1 hour. The solution was removed, and each well was washed three times with PBST. Then, SuperSignal ELISA Pico Chemiluminescent Substrate was added at 100 µl/well, and the plate was left standing at room temperature for 10 minutes, followed by the measurement of chemiluminescence using a plate reader (ARVO, PerkinElmer, Inc.). FIG. 10 shows typical reaction examples of 6 antibodies that exhibited specific binding to the amino acids at positions 1 to 48 from the N-terminus of human GPR20. The abscissa of FIG. 10 depicts clone No., and the ordinate thereof depicts the amount of the antibody bound based on chemiluminescence intensity (CPS).

1)-7 Determination of Subclass and Type of Rat Monoclonal Antibody

The heavy chain subclasses and light chain types of the rat anti-human GPR20 monoclonal antibodies were determined using RAT MONOCLONAL ANTIBODY ISOTYPING TEST KIT (DS Pharma Biomedical Co., Ltd.). As a result, it was confirmed that all of 04-093, 13-001, 13-006, 13-010, 13-040 and 13-046 had IgG2b and κ chains. As a result of analyzing their nucleotide sequences in the same way as the method described in Example 4, the respective amino acid sequences of the 13-001, 13-006, 13-010, and 13-040 antibodies had highly homologous sequences and were thus presumed to recognize the same epitope.

1)-8 Preparation of Rat Anti-Human GPR20 Antibody

The rat anti-human GPR20 monoclonal antibodies 04-093, 13-001 and 13-046 were purified from the hybridoma culture supernatants.

First, the volume of each anti-GPR20 antibody-producing hybridoma was sufficiently increased with ClonaCell-HY Selection Medium E, and, thereafter, the medium was exchanged with Hybridoma SFM (Life Technologies Corp.) to which 20% of Ultra Low IgG FBS (Life Technologies Corp.) had been added. Thereafter, the hybridoma was cultured for 4 to 5 days. The resulting culture supernatant was harvested, and insoluble matter was removed therefrom by passing through a 0.8-µm filter, and through a 0.2-µm filter.

An antibody was purified from the above-described culture supernatant of the hybridoma according to Protein G affinity chromatography. The antibody was adsorbed to a Protein G column (GE Healthcare Biosciences Corp.). The column was washed with PBS, followed by elution with a 0.1 M glycine/HCl aqueous solution (pH 2.7). The pH of the eluate was adjusted to 7.0 to 7.5 by the addition of 1 M Tris-HCl (pH 9.0). Thereafter, using Centrifugal UF Filter Device VIVASPIN20 (molecular weight cutoff: UF30K, Sartorius Inc.), the buffer was replaced with HBSor (25 mM histidine/5% sorbitol, pH 6.0), while the antibody was concentrated, so that the concentration of the antibody was adjusted to 0.7 mg/mL or more. Finally, the antibody was filtrated through Minisart-Plus filter (Sartorius Inc.) to obtain a purified sample.

Example 2: IHC Aptitude Evaluation of Rat Anti-Human GPR20 Antibody

2)-1 Evaluation of GPR20-Staining Property Using 293T Cell Transiently Expressing GPR20

2)-1-1 Production of Cell Block 293T cells were transfected with pcDNA3.1-hGPR20 or pcDNA3.1 (empty vector) using Lipofectamine 2000 (Life Technologies Corp.). Pellets of the GPR20-expressing 293T cells were fixed in formalin and then prepared into a paraffin-embedded block. Likewise, the 293T cells transfected pcDNA3.1 (empty vector) (control 293T cells) were also fixed in formalin and then prepared into a paraffin-embedded block.

2)-1-2 Immunostaining of 293T Cell Transiently Expressing GPR20

The GPR20-staining properties of the rat monoclonal anti-human GPR20 antibodies 04-093, 13-001 and 13-046 prepared in 1)-8 and commercially available rabbit polyclonal anti-human GPR20 antibodies were compared. All the commercially available antibodies were produced with a human GPR20-derived synthetic peptide as an antigen, and LS-A101 (C-terminus), LS-A102 (N-terminus), LS-A103 (cytoplasmic domain), LS-A104 (C-terminus), and LS-B7724 (amino acids at positions 291 to 340) manufactured by Lifespan Biosciences, Inc., ab75559 manufactured by Abcam PLC, NLS101 (C-terminus) manufactured by Novus Biologicals, and sc-87141 (N-terminus) manufactured by Santa Cruz Biotechnology, Inc. were used. A site within GPR20 for the synthetic peptide used in immunization for the production of each rabbit polyclonal antibody is indicated within the parentheses.

Deparaffinization and antigen retrieval were carried out at 97° C. for 20 minutes with an antigen retrieval solution (Target Retrieval Solution High pH; manufactured by Dako/Agilent Technologies Inc.) using a pretreatment system for Autostainer Link (PT Link; manufactured by Dako/Agilent Technologies Inc.). Subsequent staining procedures were carried out at room temperature using an automatic staining apparatus (Dako Autostainer Link 48; manufactured by Dako/Agilent Technologies Inc.). After washing once with EnVision FLEX WASH BUFFER (manufactured by Dako/Agilent Technologies Inc.), Peroxidase Block 3% H2O2 (manufactured by Dako/Agilent Technologies Inc.) was added to the cells, which were then incubated for 5 minutes and washed once with EnVision FLEX WASH BUFFER. Protein Block serum free (manufactured by Dako/Agilent Technologies Inc.) was added to the cells, which were then incubated for 15 minutes. The solution was removed by air blow. Each anti-GPR20 antibody was diluted to the concentrations described in Tables 2-1 and 2-2 with Signalstain Antibody Diluent (manufactured by Cell Signaling Technology, Inc.) and reacted with the cells for 30 minutes. After washing three times with EnVision FLEX WASH BUFFER, Histofine Simple Stain Mouse MAX PO (Rat) #414311 (manufactured by Nichirei Corp.) for a rat antibody and EnVision+ System-HRP Labelled Polymer Anti-Rabbit #K4003 (manufactured by Dako/Agilent Technologies Inc.) for a rabbit antibody were added according to the species of the primary antibody to the cells, which were then incubated for 30 minutes and then washed twice with EnVision FLEX WASH BUFFER.

DAKO Liquid DAB+Substrate Chromogen System was added to the cells, which were then incubated for a total of 10 minutes and then washed once with EnVision FLEX WASH BUFFER. EnVision FLEX Hematoxylin was added to the cells, which were incubated for 5 minutes and then washed a total of three times with EnVision FLEX WASH BUFFER and ion-exchanged water.

Typical staining results for each antibody are shown in FIGS. 11-1, 11-2, and 11-3. The staining intensity of each antibody in FIGS. 11-1, 11-2, and 11-3 was scored, and the results are shown in Tables 2-1 and 2-2. In the tables, +++ depicts strong positivity, ++ depicts positivity, + depicts weak positivity, and − depicts negativity. The rat monoclonal anti-GPR20 antibodies 04-093, 13-001, and 13-046 exhibited strong staining properties for the GPR20-expressing 293T cells (293-GPR20) as compared with the rabbit polyclonal anti-GPR20 antibodies. On the other hand, the rat monoclonal anti-GPR20 antibodies exhibited no staining properties for the negative control 293T cells (293-EV) and were therefore confirmed to have GPR20-specific staining properties.

TABLE 2-1

| Clone No. | Antibody [μg/mL] | 293-GPR20 | 293-EV |
|---|---|---|---|
| 04-093 | 1.5 | +++ | − |
|  | 5 | +++ | − |
|  | 10 | +++ | − |
| 13-001 | 1.5 | +++ | − |
|  | 5 | +++ | − |
|  | 10 | +++ | − |
| 13-046 | 1.5 | +++ | − |
|  | 5 | +++ | − |
|  | 10 | +++ | − |
| Rat IgG2b | 1.5 | − | − |
|  | 5 | − | − |
|  | 10 | − | − |

TABLE 2-2

| Clone No. | Antibody [μg/mL] | 293-GPR20 | 293-EV |
|---|---|---|---|
| LS-A101 | 5 | + | − |
|  | 10 | + | − |
| LS-A102 | 5 | +++ | + |
|  | 10 | +++ | ++ |
| LS-A103 | 5 | +++ | + |
|  | 10 | +++ | + |
|  | 0.5 | +++ | + |

TABLE 2-2-continued

| Clone No. | Antibody [μg/mL] | 293-GPR20 | 293-EV |
|---|---|---|---|
| LS-A104 | 1.5 | +++ | + |
|  | 5 | +++ | ++ |
| LS-B7724 | 5 | + | − |
|  | 10 | + | − |
| Ab75559 | 5 | + | − |
|  | 10 | + | − |
| NLS101 | 5 | + | − |
|  | 10 | + | − |
| sc-87141 | 2 | − | − |
|  | 5 | − | − |
| Rabbit IgG | 5 | − | − |
|  | 10 | − | − |

2)-2 Immunostaining of Clinical GIST Tissue Section

2)-2-1 Staining of GIST Tissue Array

The staining properties of anti-GPR20 antibodies in clinical specimens were studied using GIST481, Gastrointestinal stromal tumor tissue array, 24 cases/48 cores (manufactured by US Biomax, Inc.).

Deparaffinization and antigen retrieval were carried out at 97° C. for 20 minutes with an antigen retrieval solution (Target Retrieval Solution High pH; manufactured by Dako/Agilent Technologies Inc.) using a pretreatment system for Autostainer Link (PT Link; manufactured by Dako/Agilent Technologies Inc.). Subsequent staining procedures were carried out at room temperature using an automatic staining apparatus (Dako Autostainer Link 48; manufactured by Dako/Agilent Technologies Inc.). After washing once with EnVision FLEX WASH BUFFER (manufactured by Dako/Agilent Technologies Inc.), Peroxidase Block 3% H2O2 (manufactured by Dako/Agilent Technologies Inc.) was added to the cells, which were then incubated for 5 minutes and washed once with EnVision FLEX WASH BUFFER. Protein Block serum free (manufactured by Dako/Agilent Technologies Inc.) was added to the cells, which were then incubated for 15 minutes. The solution was removed by air blow. Each rat monoclonal anti-GPR20 antibody or rabbit polyclonal anti-GPR20 antibody was diluted to 10 μg/mL or 5 μg/mL with Signalstain Antibody Diluent (manufactured by Cell Signaling Technology, Inc.) and reacted with the cells for 30 minutes. After washing three times with EnVision FLEX WASH BUFFER, Histofine Simple Stain Mouse MAX PO (Rat) #414311 (manufactured by Nichirei Corp.) was added to the cells, which were then incubated for 30 minutes and then washed twice with EnVision FLEX WASH BUFFER.

DAKO Liquid DAB+Substrate Chromogen System was added to the cells, which were then incubated for a total of 10 minutes and then washed once with EnVision FLEX WASH BUFFER. EnVision FLEX Hematoxylin was added to the cells, which were incubated for 5 minutes and then washed a total of three times with EnVision FLEX WASH BUFFER and ion-exchanged water.

In FIG. 12, as a result of comparing the GPR20-staining properties of the antibodies for (FIG. 12-1) stomach GIST, (FIG. 12-2) small intestine GIST, and (FIG. 12-3) large intestine GIST, the rat anti-GPR20 antibody 04-093 was most highly sensitive.

Example 3: Sequence Analysis of Rat Anti-Human GPR20 Antibody 04-093

3)-1 Preparation of Total RNA from 04-093-Producing Hybridoma

In order to amplify cDNA encoding the heavy chain and light chain signal sequences and variable regions of 04-093, total RNA was prepared from the 04-093-producing hybridoma using TRIzol Reagent (Ambion, Inc.).

3)-2 Amplification of cDNA Encoding Heavy Chain Signal Sequence and Variable Region of 04-093 by 5'-RACE PCR, and Determination of Nucleotide Sequence The amplification of cDNA encoding the heavy chain signal sequence and variable region of 04-093 was carried out using approximately 1 µg of the total RNA prepared in Example 3)-1 and SMARTer RACE cDNA Amplification Kit (Clontech Laboratories, Inc.). UPM (Universal Primer A Mix; attached to SMARTer RACE cDNA Amplification Kit) and a primer designed from the sequence of the constant region of a known rat heavy chain were used as primers for amplifying the cDNA encoding the heavy chain signal sequence and variable region of 04-093 by PCR.

The cDNA encoding the heavy chain signal sequence and variable region, thus amplified by 5'-RACE PCR was cloned into a plasmid. Then, sequence analysis was conducted on the nucleotide sequence of the cDNA of the heavy chain signal sequence and variable region.

3)-3 Amplification of cDNA Encoding Light Chain Signal Sequence and Variable Region of 04-093 by 5'-RACE PCR, and Determination of Nucleotide Sequence The amplification of cDNA was carried out in the same way as in Example 3)-2 except that UPM (Universal Primer A Mix; attached to SMARTer RACE cDNA Amplification Kit) and a primer designed from the sequence of the constant region of a known rat light chain were used as primers for amplifying the cDNA encoding the light chain signal sequence and variable region of 04-093 by PCR.

The full-length sequences of the heavy chain and light chain of the 04-093 antibody were determined by linking them to known constant region sequences. The nucleotide sequence and amino acid sequence of the constant region of rat heavy chain IgG2b were used with reference to the nucleotide sequence and the amino acid sequence of AABR03048905 (IGHG2B*01) disclosed in IMGT, the international ImMunoGeneTics information system (registered trademark). The nucleotide sequence and the amino acid sequence of the constant region of rat light chain IgK were used with reference to the nucleotide sequence and amino acid sequence of V01241 (IGKC*01) also disclosed in this system.

The heavy chain of the 04-093 antibody has the amino acid sequence shown in SEQ ID NO: 3 in the sequence listing. In the heavy chain amino acid sequence shown in SEQ ID NO: 3 in the sequence listing, the amino acid sequence consisting of the amino acid residues at positions 1 to 19 is a signal sequence, the amino acid sequence consisting of the amino acid residues at positions 20 to 133 is a variable region, and the amino acid sequence consisting of the amino acid residues at positions 134 to 466 is a constant region. The aforementioned variable region has CDRH1 consisting of the amino acid sequence at positions 45 to 54 (GFTFNNYWMT) or the amino acid sequence at positions 50 to 54 (NYWMT), CDRH2 consisting of the amino acid sequence at positions 69 to 78 (SITNIDGSSY) or the amino acid sequence at positions 69 to 85 (SITNIDGSSYYPDSVKG), and CDRH3 consisting of the amino acid sequence at positions 118 to 122 (GSFDY), in SEQ ID NO: 3 in the sequence listing. The heavy chain variable region of the 04-093 antibody has the amino acid sequence shown in SEQ ID NO: 4 in the sequence listing. The CDRH1 of the 04-093 antibody has the amino acid sequence shown in SEQ ID NO: 5 or 8 in the sequence listing, the amino acid sequence of the CDRH2 has the amino acid sequence shown in SEQ ID NO: 6 or 9 in the sequence listing, and the amino acid sequence of the CDRH3 has the amino acid sequence shown in SEQ ID NO: 7 in the sequence listing. Furthermore, the amino acid sequence of the heavy chain of the 04-046 antibody is shown in FIG. 1.

The light chain of the 04-093 antibody has the amino acid sequence shown in SEQ ID NO: 11 in the sequence listing. In the light chain amino acid sequence shown in SEQ ID NO: 11 in the sequence listing, the amino acid sequence consisting of the amino acid residues at positions 1 to 19 is a signal sequence, the amino acid sequence consisting of the amino acid residues at positions 20 to 126 is a variable region, and the amino acid sequence consisting of the amino acid residues at positions 127 to 232 is a constant region. The aforementioned variable region has CDRL1 consisting of the amino acid sequence at positions 43 to 53, CDRL2 consisting of the amino acid sequence at positions 69 to 75, and CDRL3 consisting of the amino acid sequence at positions 108 to 115, in SEQ ID NO: 11 in the sequence listing. The light chain variable region of the 04-093 antibody has the amino acid sequence shown in SEQ ID NO: 12 in the sequence listing. The CDRL1 of the 04-093 antibody has the amino acid sequence shown in SEQ ID NO: 13 (KASQNVNKYLN) in the sequence listing, the amino acid sequence of the CDRL2 has the amino acid sequence shown in SEQ ID NO: 14 (NTNNLQT) in the sequence listing, and the amino acid sequence of the CDRL3 has the amino acid sequence shown in SEQ ID NO: 15 (FQHVSWLT) in the sequence listing. Furthermore, the amino acid sequence of the light chain of the 04-093 antibody is shown in FIG. 2.

The heavy chain amino acid sequence of the 04-093 antibody is encoded by the nucleotide sequence shown in SEQ ID NO: 2 in the sequence listing. In the nucleotide sequence shown in SEQ ID NO: 2 in the sequence listing, the nucleotide sequence consisting of the nucleotides at positions 1 to 57 is a signal sequence. In the nucleotide sequence shown in SEQ ID NO: 2 in the sequence listing, the nucleotide sequence consisting of the nucleotides at positions 58 to 399 encodes the heavy chain variable region of the 04-093 antibody, and the nucleotide sequence consisting of the nucleotides at positions 400 to 1398 encodes the heavy chain constant region of the 04-093 antibody. The nucleotide sequence encoding the aforementioned variable region has a polynucleotide consisting of the nucleotide sequence at nucleotide positions 133 to 162 or nucleotide positions 118 to 162 encoding CDRH1, a polynucleotide consisting of the nucleotide sequence at nucleotide positions 205 to 234 or nucleotide positions 205 to 183 encoding CDRH2, and a polynucleotide consisting of the nucleotide sequence at nucleotide positions 352 to 366 encoding CDRH3, in SEQ ID NO: 2. The nucleotide sequences of the heavy chain signal sequence and variable region of the 04-093 antibody are also shown in SEQ ID NO: 16 in the sequence listing. In the nucleotide sequence shown in SEQ ID NO: 16 in the sequence listing, the nucleotide sequence consisting of the nucleotides at positions 1 to 57 represents the signal sequence, and the nucleotide sequence consisting of the nucleotides at positions 58 to 399 encodes the heavy chain variable region. The sequence of SEQ ID NO: 2 is also shown in FIG. 1.

The light chain amino acid sequence of the 04-093 antibody is encoded by the nucleotide sequence shown in SEQ ID NO: 10 in the sequence listing. In the nucleotide sequence shown in SEQ ID NO: 10 in the sequence listing, the nucleotide sequence consisting of the nucleotides at positions 1 to 57 is a signal sequence. In the nucleotide sequence shown in SEQ ID NO: 10 in the sequence listing, the nucleotide sequence consisting of the nucleotides at positions 58 to 378 encodes the light chain variable region of the 04-093 antibody, and the nucleotide sequence consisting of the nucleotides at positions 379 to 696 encodes the light chain constant region of the 04-093 antibody. The nucleotide sequence encoding the aforementioned variable region has a polynucleotide consisting of the nucleotide sequence at nucleotide positions 127 to 159 encoding CDRL1, a polynucleotide consisting of the nucleotide sequence at nucleotide positions 205 to 225 encoding CDRL2, and a polynucleotide consisting of the nucleotide sequence at nucleotide positions 322 to 345 encoding CDRL3, in SEQ ID NO: 10. The nucleotide sequences of the light chain signal sequence and variable region of the 04-093 antibody are also shown in SEQ ID NO: 17 in the sequence listing. In the nucleotide sequence shown in SEQ ID NO: 17 in the sequence listing, the nucleotide sequence consisting of the nucleotides at positions 1 to 57 represents the signal sequence, and the nucleotide sequence consisting of the nucleotides at positions 58 to 378 encodes the light chain variable region. The sequence of SEQ ID NO: 10 is also shown in FIG. 2.

Example 4: Production of Rabbit Chimeric Anti-GPR20 Antibody and Rabbit Type Anti-GPR20 Antibody 4)-1 Design of Rabbit Chimeric Form of Anti-GPR20 Antibody 04-093

A rabbit chimeric sequence was designed by linking rabbit heavy chain constant region IGHG*02 and rabbit light chain constant region IGKC2*01 to the heavy chain and light chain variable regions, respectively, of the clone 04-093 with reference to IMGT®, the international ImMunoGeneTics information System®.

The rabbit chimeric antibody heavy chain was named OcHch. The amino acid sequence thereof is shown in SEQ ID NO: 19. In SEQ ID NO: 19, the amino acid sequence at amino acid positions 1 to 19 represents the amino acid sequence of a signal sequence, the amino acid sequence at positions 20 to 133 represents the amino acid sequence of a heavy chain variable region, and the amino acid sequence at positions 134 to 456 represents the amino acid sequence of a heavy chain constant region.

The rabbit chimeric antibody light chain was named OcLch. The amino acid sequence thereof is shown in SEQ ID NO: 21. In SEQ ID NO: 21, the amino acid sequence at amino acid positions 1 to 20 represents the amino acid sequence of a signal sequence, the amino acid sequence at positions 21 to 127 represents the amino acid sequence of a light chain variable region, and the amino acid sequence at positions 128 to 232 represents the amino acid sequence of a light chain constant region.

4)-2 Design of Rabbit Type Form of Anti-GPR20 Antibody 04-093

The amino acid sequences of the variable regions of a rabbit type antibody were designed by CDR grafting (Proc. Natl. Acad. Sci. USA 86, 10029-10033 (1989)). Heavy chain acceptor sequences IGHV1S7*01 and IGHJ3*01, and light chain acceptor sequences IGKV1S39*01 and IGKJ1-2*01 were selected based on the amino acid sequence identity of the variable regions and moderation for a rabbit germline sequence. The constructed homology models of the clone 04-093 were analyzed using the protein three-dimensional structure analysis program BioLuminate (manufactured by Schrodinger, LLC), and donor residues to be grafted onto the acceptors were selected based on the criteria given by Queen et al. (Proc. Natl. Acad. Sci. USA 86, 10029-10033 (1989)). Rabbit IGHG*02 was selected as a heavy chain constant region, and rabbit IGKC1*01 was selected as a light chain constant region.

Two types of rabbit type antibody heavy chains, OcH01 and OcH02, were designed. The amino acid sequences thereof are shown in SEQ ID NOs: 23 and 25, respectively. In SEQ ID NOs: 23 and 25, the amino acid sequence at positions 1 to 19 represents a signal sequence, the amino acid sequence at positions 20 to 133 represents a variable region, and the amino acid sequence at positions 134 to 456 represents a constant region.

One type of rabbit type antibody light chain, OcL01, was designed. The amino acid sequence thereof is shown in SEQ ID NO: 27. In SEQ ID NO: 27, the amino acid sequence at positions 1 to 20 represents a signal sequence, the amino acid sequence at positions 21 to 127 represents a variable region, and the amino acid sequence at positions 128 to 230 represents a constant region.

4)-2 Production of Recombinant Antibody

4)-2-1 Construction of Rabbit Chimeric Anti-GPR20 Antibody Heavy Chain Expression Vector 4)-2-1-1 Construction of Antibody Expression Vector pCMA-LK An approx. 5.4-kb fragment, which had been obtained by digesting plasmid pcDNA3.3-TOPO/LacZ (Invitrogen Corp.) with the restriction enzymes XbaI and PmeI, was bound to a DNA fragment comprising a DNA sequence (SEQ ID NO: 28) encoding the amino acid sequences of a human light chain signal sequence and a human κ chain constant region, using an In-Fusion Advantage PCR cloning kit (Clontech Laboratories, Inc.), to produce pcDNA3.3/LK.

A neomycin expression unit was removed from pcDNA3.3/LK to construct pCMA-LK.

4)-2-1-2 Construction of Rabbit Chimeric Antibody Heavy Chain OcHch Expression Vector A DNA fragment comprising a DNA sequence (SEQ ID NO: 18) encoding the amino acid sequence of the rabbit chimeric antibody heavy chain OcHch was synthesized (GENEART). In the nucleotide sequence shown in SEQ ID NO: 18 in the sequence listing, the nucleotide sequence consisting of the nucleotides at positions 26 to 82 encodes a signal sequence, the nucleotide sequence consisting of the nucleotides at positions 83 to 424 encodes the heavy chain variable region, and the nucleotide sequence consisting of the nucleotides at positions 425 to 1393 encodes the constant region.

Using an In-Fusion HD PCR cloning kit (Clontech Laboratories, Inc.), the synthesized DNA fragment was bound to a DNA fragment, which had been obtained by digesting pCMA-LK with XbaI and PmeI to remove the DNA sequence encoding the light chain signal sequence and the human κ chain constant region therefrom, so as to construct a rabbit chimeric antibody heavy chain OcHch expression vector.

4)-2-2 Construction of Rabbit Chimeric Anti-GPR20 Antibody Light Chain Expression Vector 4)-2-2-1 Construction of Rabbit Chimeric Antibody Light Chain OcLch Expression Vector A DNA fragment comprising a DNA sequence (SEQ ID NO: 20) encoding the amino acid sequence of the rabbit chimeric antibody light chain OcLch was synthesized (GENEART). In the nucleotide sequence shown in SEQ ID NO: 20 in the sequence listing, the nucleotide sequence consisting of the nucleotides at positions 26 to 85 encodes a signal sequence, the nucleotide sequence consisting of the nucleotides at positions 86 to 406 encodes the light chain variable region, and the nucleotide sequence consisting of the nucleotides at positions 407 to 721 encodes the constant region. A rabbit chimeric antibody light chain OcLch expression vector was constructed in the same way as in Example 4)-2-1-2.

4)-2-3 Construction of Rabbit Type Anti-GPR20 Antibody Heavy Chain Expression Vector 4)-2-3-1 Construction of Rabbit Type Antibody Heavy Chain OcH01 Expression Vector A DNA fragment comprising a DNA sequence (SEQ ID NO: 22) encoding the amino acid sequence of the rabbit type antibody heavy chain OcH01 was synthesized (GENEART). In the nucleotide sequence shown in SEQ ID NO: 22 in the sequence listing, the nucleotide sequence consisting of the nucleotides at positions 26 to 82 encodes a signal sequence, the nucleotide sequence consisting of the nucleotides at positions 83 to 424 encodes the heavy chain variable region, and the nucleotide sequence consisting of the nucleotides at positions 425 to 1393 encodes the constant region. A rabbit type antibody heavy chain OcH01 expression vector was constructed in the same way as in Example 4)-2-1-2.

4)-2-3-2 Construction of Rabbit Type Antibody Heavy Chain OcH02 Expression Vector A DNA fragment comprising a DNA sequence (SEQ ID NO: 24) encoding the amino acid sequence of the rabbit type antibody heavy chain OcH02 was synthesized (GENEART). In the nucleotide sequence shown in SEQ ID NO: 24 in the sequence listing, the nucleotide sequence consisting of the nucleotides at positions 26 to 82 encodes a signal sequence, the nucleotide sequence consisting of the nucleotides at positions 83 to 424 encodes the heavy chain variable region, and the nucleotide sequence consisting of the nucleotides at positions 425 to 1393 encodes the constant region. A rabbit type antibody heavy chain OcH02 expression vector was constructed in the same way as in Example 4)-2-1-2.

4)-2-4 Construction of Rabbit Type Anti-GPR20 Antibody Light Chain Expression Vector 4)-2-4-1 Construction of Rabbit Type Antibody Light Chain OcL01 Expression Vector A DNA fragment comprising a DNA sequence (SEQ ID NO: 26) encoding the amino acid sequence of the rabbit type antibody light chain OcL01 was synthesized (GENEART). In the nucleotide sequence shown in SEQ ID NO: 26 in the sequence listing, the nucleotide sequence consisting of the nucleotides at positions 26 to 85 encodes a signal sequence, the nucleotide sequence consisting of the nucleotides at positions 86 to 406 encodes the light chain variable region, and the nucleotide sequence consisting of the nucleotides at positions 407 to 721 encodes the constant region. A rabbit type antibody light chain OcL01 expression vector was constructed in the same way as in Example 5)-2-1-2.

4)-2-5 Preparation of Recombinant Antibody

4)-2-5-1 Production of Recombinant Antibody

In accordance with the manual, FreeStyle 293F cells (Invitrogen Corp.) were cultured and passaged. $1.2 \times 10^9$ FreeStyle 293F cells (Invitrogen Corp.) in the logarithmic growth phase were seeded on 3-L Fernbach Erlenmeyer Flask (Corning Inc.), then diluted with FreeStyle 293 expression medium (Invitrogen Corp.) at $2.0 \times 10^6$ cells/mL. 0.24 mg of the heavy chain expression vector, 0.36 mg of the light chain expression vector, and 1.8 mg of Polyethyleneimine (Polyscience #24765) were added to 40 mL of Opti-Pro SFM medium (Invitrogen Corp.), and the obtained mixture was gently stirred. After incubation for 5 minutes, the mixture was added to the FreeStyle 293F cells. The cells were shake-cultured at 90 rpm in an 8% $CO_2$ incubator at 37° C. for 4 hours, and thereafter, 600 mL of EX-CELL VPRO medium (SAFC Biosciences Inc.), 18 mL of GlutaMAX I (GIBCO), and 30 mL of Yeastolate Ultrafiltrate (GIBCO) were added to the culture. The cells were further shake-cultured at 90 rpm in an 8% $CO_2$ incubator at 37° C. for 7 days. The obtained culture supernatant was filtered through Disposable Capsule Filter (Advantec #CCS -045-E1H).

OcChimera was produced by the combination of the OcHch and OcLch expression vectors in the expression of the recombinant antibody. OcH1L1 was produced by the combination of the OcH01 and OcL01 expression vectors. An OcH2L1 antibody was produced by the combination of the OcH02 and OcL01 expression vectors.

4)-2-5-2 Purification of Recombinant Antibody

The antibody was purified from the culture supernatant obtained in Example 4)-2-5-1, by a one-step process of rProtein A affinity chromatography. The culture supernatant was applied to a column that had been packed with MabSelectSuRe (manufactured by GE Healthcare Biosciences Corp.) equilibrated with PBS. The column was washed with PBS in an amount of two or more times the volume of the column. Subsequently, elution was carried out using a 2 M arginine hydrochloride solution (pH 4.0), so that a fraction containing an antibody was collected. This fraction was dialyzed (Thermo Fisher Scientific Inc., Slide-A-Lyzer Dialysis Cassette), so that the buffer was replaced with PBS. The antibody was concentrated with Centrifugal UF Filter Device VIVASPIN20 (molecular weight cutoff: UF10K, Sartorius Inc.), thereby adjusting the IgG concentration to 2 mg/mL. Finally, the antibody was filtrated through Minisart-Plus filter (Sartorius Inc.) to obtain a purified sample.

Example 5: Immunostaining Using Rabbit Chimeric Anti-GPR20 Antibody and Rabbit Type Anti-GPR20 Antibody 5)-1 Immunostaining of GIST Cell Line The staining properties of the rabbit chimeric anti-GPR20 antibody and the rabbit type anti-GPR20 antibodies produced in Example 4)-2-5 were studied using paraffin-embedded preparations of GIST cell lines (GIST430 and GIST430/654) and a prostate cancer cell line (PC-3) as a negative control. Deparaffinization and antigen retrieval were carried out at 97° C. for 40 minutes with an antigen retrieval solution (Target Retrieval Solution High pH; manufactured by Dako/Agilent Technologies Inc.) using a pretreatment system for Autostainer Link (PT Link; manufactured by Dako/Agilent Technologies Inc.). Subsequent staining procedures were carried out at room temperature using an automatic staining apparatus (Dako Autostainer Link 48; manufactured by Dako/Agilent Technologies Inc.). After washing once with EnVision FLEX WASH BUFFER (manufactured by Dako/Agilent Technologies Inc.), Peroxidase Block 3% H2O2 (manufactured by Dako/Agilent Technologies Inc.) was added to the cells, which were then incubated for 5 minutes and washed once with EnVision FLEX WASH BUFFER. Protein Block serum free (manufactured by Dako/Agilent Technologies Inc.) was added to the cells, which were then incubated for 30 minutes. The solution was removed by air blow. A rat monoclonal anti-GPR20 antibody, a rabbit chimeric anti-GPR20 antibody or a rabbit type anti-GPR20 antibody was diluted into 1.0 μg/mL to 10 μg/mL with REAL Antibody Diluent (manufactured by Dako/Agilent Technologies Inc.) and reacted with the cells for 30 minutes. After washing three times with EnVision FLEX WASH BUFFER, Histofine simple stain mouse MAX PO (Rat) #414311 (manufactured by Nichirei Corp.) for a rat antibody and EnVision+ System-HRP Labelled Polymer Anti-Rabbit #K4003 (manufactured by Dako/Agilent Technologies Inc.) for a rabbit antibody were added to the cells, which were then incubated for 30 minutes and then washed twice with EnVision FLEX WASH BUFFER.

DAKO Liquid DAB+Substrate Chromogen System was added to the cells, which were then incubated for a total of 10 minutes and then washed once with EnVision FLEX WASH BUFFER. EnVision FLEX Hematoxylin was added to the cells, which were incubated for 5 minutes and then washed a total of three times with EnVision FLEX WASH BUFFER and ion-exchanged water.

FIG. 13 shows typical staining images. The rabbit chimeric antibody OcChimera and the rabbit type antibodies OcH1L1 and OcH2L1 exhibited highly sensitive staining properties for the GIST cell lines as compared with the rat antibody 04-093. These antibodies exhibited no staining properties for the prostate cancer cell line that did not express GPR20.

5)-2 Immunostaining of Clinical GIST

The staining properties of the rabbit chimeric anti-GPR20 antibody and the rabbit type anti-GPR20 antibodies in clinical specimens were studied using GIST801, Gastrointestinal stromal tumor tissue array, 80 cases/80 cores (manufactured by US Biomax, Inc.). Staining was carried out in the same way as in Example 5)-1.

In FIG. 14, as a result of comparing the GPR20-staining properties of the antibodies for (FIG. 14-1) stomach GIST, (FIG. 14-2) small intestine GIST, and (FIG. 14-3) large intestine GIST, all of the rabbit chimeric anti-GPR20 antibody and the rabbit type anti-GPR20 antibodies were found to be more highly sensitive than the rat anti-GPR20 antibody 04-093.

Example 6: Identification of Epitope

6)-1 Evaluation of Binding Ability by Peptide-ELISA

The binding of the rat anti-human GPR20 antibody 04-093 to synthetic peptides given below was evaluated by peptide-ELISA. NeutrAvidin (Pierce/Thermo Fisher Scientific Inc.) diluted to 1 μg/mL with PBS was added at 100 μL/well to 96-well Maxisorp plate (Nunc), and the plate was left standing overnight at 4° C. The solution was removed, and the plate was washed three times with 300 μL/well of PBS containing 0.05% Tween 20 (hereinafter, referred to as PBST). Then, C-terminally biotinylated synthetic peptide 1 consisting of amino acid positions 1 to 48 (SEQ ID NO: 29) of human GPR20, synthetic peptide 2 consisting of amino acid positions 30 to (SEQ ID NO: 30) of human GPR20, and a negative control synthetic peptide having a sequence different from the amino acid sequence of GPR20 were each dissolved at 10 nM in PBS, and this solution was added at 100 μL/well. The plate was left standing at room temperature for 1 hour. The solution was removed from the plate, and each well was washed three times with PBST. Then, Blocker Casein in PBS (Thermo Fisher Scientific Inc.) was added at 100 μL/well, and the plate was left standing overnight at room temperature. The solution was removed, and each well was washed three times with PBST. Then, the 04-093 antibody diluted to 1 μg/mL with Blocker Casein in PBS was added at 100 μL/well, and the plate was left standing at room temperature for 1 hour. The solution was removed, and each well was washed three times with PBST. Then, Anti-Rat IgG-Peroxidase antibody produced in rabbit (Jackson ImmunoResearch Laboratories, Inc.) 500-fold diluted with PBS was added at 100 μL/well, and the plate was left standing at room temperature for 1 hour. The solution was removed, and each well was washed three times with PBST. Then, SuperSignal ELISA Pico Chemiluminescent Substrate was added at 100 μl/well, and the plate was left standing at room temperature for 10 minutes, followed by the measurement of chemiluminescence using a plate reader (SpectraMax M3, Molecular Devices, LLC). FIG. 15 shows reaction examples of various antibodies. The abscissa of FIG. 15 depicts clone No., and the ordinate thereof depicts the amount of the antibody bound based on chemiluminescence intensity (CPS). The 04-093 antibody exhibited equivalent binding activity against the synthetic peptide 1 and the synthetic peptide 2. On the other hand, the other anti-GPR20 antibodies exhibited no binding activity against the synthetic peptide 2. These results indicated that the 04-093 antibody binds to an amino acid sequence consisting of amino acid positions 30 to 48 (SEQ ID NO: 30: LEVPLFHLFARLDEELHGT) of GPR20.

6)-2 Evaluation of Binding Ability Using GPR20 Fragment Peptide

For the detailed analysis of the epitope, a peptide consisting of amino acid positions 29 to 48 of GPR20, and peptides in which a terminal amino acid residue was continuously truncated one by one from this peptide, were synthesized, and then N-terminally biotinylated and C-terminally amidated to produce a GPR20 fragment peptide library (Sigma-Aldrich Japan G.K.). The dissociation constant of the 04-093 antibody for the produced GPR20 fragment peptides was measured by using an Octet RED384 system (manufactured by Pall ForteBio Corp.), capturing the GPR20 fragment peptides as ligands on sensor chips, and using the 04-093 antibody as an analyte. PBS-T was used as a buffer solution, and the sensor chips used were streptavidin sensor chips (manufactured by Pall ForteBio Corp.). For each GPR20 fragment peptide, a sensor chip was dipped in 1 μg/mL peptide solution for 300 seconds and then dipped in serially diluted solutions of the 04-093 antibody (3-fold dilution series from 0.247 to 20 nM, 5 concentrations) for 90 seconds, and an association phase was monitored. Subsequently, the sensor chip was dipped in the buffer solution, and a dissociation phase was monitored for 270 seconds. After measurement of the 04-093 antibody with each concentration, the sensor chip was dipped in a citrate buffer solution (pH 2.2) for 20 seconds for regeneration, and further dipped in the buffer solution for 20 seconds for equilibration. The data was analyzed using 1:1 binding models to calculate association rate constant ka, dissociation rate constant kd and dissociation constant KD (KD=kd/ka). The results are shown in Table 3.

TABLE 3

| Peptide sequence | KD(M) |
|---|---|
| GLEVPLFHLFARLDEELHGT | <1.0 × 10$^{-12}$ |
| GLEVPLFHLFARLDEE | <1.0 × 10$^{-12}$ |
| GLEVPLFHLFARLDE | <1.0 × 10$^{-12}$ |
| GLEVPLFHLFARLD | <1.0 × 10$^{-12}$ |
| GLEVPLFHLFARL | 1.1 × 10$^{-9}$ |
| GLEVPLFHLFAR | 1.3 × 10$^{-8}$ |
| GLEVPLFHLFA | Unmeasurable |
| GLEVPLFHLFARLDEEL | <1.0 × 10$^{-12}$ |
| LEVPLFHLFARLDEEL | <1.0 × 10$^{-12}$ |
| EVPLFHLFARLDEEL | 1.1 × 10$^{-9}$ |
| VPLFHLFARLDEEL | 5.7 × 10$^{-9}$ |
| PLFHLFARLDEEL | Unmeasurable |

The GPR20 fragment peptide (GLEVPLFHLFARLD: amino acid positions 29 to 42 of SEQ ID NO: 29) exhibited strong binding to the 04-093 antibody, whereas the binding was reduced in the GPR20 fragment peptide (GLEVPLFHL-FARL: amino acid positions 29 to 41 of SEQ ID NO: 29). Furthermore, the GPR20 fragment peptide (LEVPLFHL-FARLDEEL: amino acid positions 30 to 45 of SEQ ID NO: 29) exhibited strong binding to the 04-093 antibody, whereas the binding was reduced in the GPR20 fragment peptide (EVPLFHLFARLDEEL: amino acid positions 31 to 45 of SEQ ID NO: 29). From these results, amino acid positions 30 to 42 (LEVPLFHLFARLD: SEQ ID NO: 31) of SEQ ID NO: 29 was identified as the epitope of the 04-093 antibody.

Example 7: Detection of GPR20 Protein by Western Blotting

GPR20 protein transiently expressed in 293T cells was detected by Western blotting. 293T cells were transfected with human GPR20 expression vector pcDNA3.1-hGPR20, N-terminally FLAG-tagged human GPR20 expression vector pFLAG-GPR2, or pcDNA3.1 (empty vector) using Lipofectamine 2000 (Life Technologies Corp.). A protein solution of a membrane fraction was prepared from the cells using a Mem-PER Plus Membrane Protein Extraction Kit (Thermo Fisher Scientific Inc.), and the protein concentration was measured using a BCA protein assay (Thermo Fisher Scientific Inc.). To the concentration-adjusted protein solution, NuPAGE™ LDS Sample Buffer (4×) and NuPAGE™ Sample Reducing Agent (10×) (Thermo Fisher Scientific Inc.) were added to attain 1× concentration. After heating at 70° C. for 10 minutes, 20 μg/lane of the protein was electrophoresed by SDS-PAGE using Tris/glycine/SDS buffer according to the standard method. The protein was transferred from the gel after electrophoresis to Immobilon-FL membrane (Merck Millipore). This Immobilon-FL membrane was blocked with Odyssey Blocking Buffer (LI-COR, Inc.) for 1 hour, and then shaken overnight at 4° C. in a primary antibody reaction solution of a rabbit chimeric anti-GPR20 antibody or a rabbit type anti-GPR20 antibody diluted with 0.1% Tween 20/Odyssey Blocking Buffer. Likewise, rabbit IgG, a mouse anti-FLAG antibody, and a mouse anti-β actin antibody were used as controls in primary antibody reaction solutions. The membrane was washed three times with TBS-0.1% Tween 20 buffer using a SNAP i.d. system (Merck Millipore), then reacted in a secondary antibody solution (IRDye 680CW Goat anti-rabbit IgG was used when the primary antibody was a rabbit antibody, and IRDye 800CW Goat anti-mouse IgG was used when the primary antibody was a mouse antibody) diluted with 0.1% Tween 20/Odyssey Blocking Buffer, and then washed twice with TBS -0.1% Tween 20 buffer and once with TBS. Fluorescence was detected using an Odyssey Infrared Imaging System (LI-COR, Inc.). In FIG. 17, the rabbit type anti-GPR20 antibodies OcH1L1 and OcH2L1 and the rabbit chimeric anti-GPR20 antibody OcChimera exhibited reactivity with 293T-pcDNA3.1-GPR20 cells expressing human GPR20 or 293T-pFLAG-GPR20 cells expressing N-terminally FLAG-tagged human GPR20, and a plurality of bands were detected. On the other hand, no band was detected in the negative control 293T-pcDNA3.1 cells. Furthermore, the mouse anti-FLAG antibody exhibited reactivity only with 293T-pFLAG-GPR20, and a plurality of bands were detected. These results indicated that the rabbit chimeric anti-GPR20 antibody and the rabbit type anti-GPR20 antibody are useful in the detection of GPR20 by Western blotting.

INDUSTRIAL APPLICABILITY

Use of the anti-GPR20 antibody provided by the present invention enables testing or diagnosis of various cancers expressing GPR20. Thus, the present invention can provide a kit and the like for the testing or diagnosis of various cancers expressing GPR20, comprising the anti-GPR20 antibody of the present invention. The present invention can also provide a pharmaceutical composition and the like comprising the anti-GPR20 antibody of the present invention as an active ingredient.

SEQUENCE LISTING FREE TEXT

SEQ ID NO: 18: Nucleotide sequence of a DNA fragment comprising a sequence encoding the amino acid sequence of rabbit chimeric antibody heavy chain OcHch SEQ ID NO: 19: Amino acid sequence of the rabbit chimeric antibody heavy chain OcHch SEQ ID NO: 20: Nucleotide sequence of a DNA fragment comprising a sequence encoding the amino acid sequence of rabbit chimeric antibody light chain OcLch SEQ ID NO: 21: Amino acid sequence of the rabbit chimeric antibody light chain OcLch SEQ ID NO: 22: Nucleotide sequence of a DNA fragment comprising a sequence encoding the amino acid sequence of rabbit type antibody heavy chain OcH01

SEQ ID NO: 23: Amino acid sequence of the rabbit type antibody heavy chain OcH01

SEQ ID NO: 24: Nucleotide sequence of a DNA fragment comprising a sequence encoding the amino acid sequence of rabbit type antibody heavy chain OcH02

SEQ ID NO: 25: Amino acid sequence of the rabbit type antibody heavy chain OcH02

SEQ ID NO: 26: Nucleotide sequence of a DNA fragment comprising a sequence encoding the amino acid sequence of rabbit type antibody light chain OcL01

SEQ ID NO: 27: Amino acid sequence of the rabbit type antibody light chain OcL01

SEQ ID NO: 28: DNA fragment comprising a DNA sequence encoding the amino acid sequences of a human light chain signal sequence and a human κ chain constant region SEQ ID NO: 29: Synthetic peptide 1 (amino acid sequence at positions 1 to 48 of human GPR20)

The invention claimed is:

1. An antibody that specifically binds to a peptide comprising an amino acid sequence of amino acids 1 to 48 of SEQ ID NO: 1, or an antigen-binding fragment of the antibody, wherein the antibody or antigen-binding fragment comprises:
 a heavy chain sequence comprising a variable region comprising a CDRH1 comprising SEQ ID NO: 5 or 8, a CDRH2 comprising SEQ ID NO: 6 or 9, and a CDRH3 comprising SEQ ID NO: 7; and
 a light chain sequence comprising a variable region comprising a CDRL1 comprising SEQ ID NO: 13, a CDRL2 comprising SEQ ID NO: 14, and a CDRL3 comprising SEQ ID NO: 15.

2. The antibody or the antigen-binding fragment of the antibody according to claim 1, which binds to an epitope consisting of the amino acid sequence LEVPLFHLFARLD (SEQ ID NO: 31).

3. The antibody or the antigen-binding fragment of the antibody according to claim 1, which comprises a heavy chain variable region consisting of the amino acid sequence shown in SEQ ID NO: 4 and a light chain variable region consisting of the amino acid sequence shown in SEQ ID NO: 12.

4. The antibody or the antigen-binding fragment of the antibody according to claim 1, which consists of a heavy chain comprising the amino acid sequence at amino acid positions 20 to 466 in SEQ ID NO: 3, and a light chain comprising the amino acid sequence at amino acid positions 20 to 232 in SEQ ID NO: 11.

5. The antibody or the antigen-binding fragment of the antibody according to claim 1, which is a chimeric antibody.

6. The chimeric antibody according to claim 5, wherein the constant region is derived from a rabbit antibody.

7. The antibody or the antigen-binding fragment of the antibody according to claim 1, which comprises a heavy chain consisting of the amino acid sequence at amino acid positions 20 to 456 in SEQ ID NO: 19 and a light chain consisting of the amino acid sequence at amino acid positions 21 to 232 in SEQ ID NO: 21.

8. The antibody or the antigen-binding fragment of the antibody according to claim 1, which is of rabbit type.

9. The antibody or the antigen-binding fragment of the antibody according to claim 1, which is humanized.

10. The antibody or the antigen-binding fragment of the antibody according to claim 1, which comprises the following heavy chain (a) or (b) and light chain (c):
 (a) a heavy chain consisting of the amino acid sequence at amino acid positions 20 to 456 in SEQ ID NO: 23,
 (b) a heavy chain consisting of the amino acid sequence at amino acid positions 20 to 456 in SEQ ID NO: 25, and
 (c) a light chain consisting of the amino acid sequence at amino acid positions 21 to 230 in SEQ ID NO: 27.

11. The antibody or the antigen-binding fragment of the antibody according to claim 1, which consists of a heavy chain comprising the amino acid sequence at amino acid positions 20 to 456 in SEQ ID NO: 23 and a light chain comprising the amino acid sequence at amino acid positions 21 to 230 in SEQ ID NO: 27.

12. The antibody or the antigen-binding fragment of the antibody according to claim 1, which consists of a heavy chain comprising the amino acid sequence at amino acid positions 20 to 456 in SEQ ID NO: 25 and a light chain comprising the amino acid sequence at amino acid positions 21 to 230 in SEQ ID NO: 27.

13. The antigen-binding fragment of the antibody according to claim 1, which is selected from the group consisting of Fab, F(ab')2, Fab' and Fv.

14. The antibody according to claim 1, which is scFv.

15. A composition comprising the antibody or the antigen-binding fragment of the antibody according to claim 1.

16. A method for detecting or measuring GPR20 in a tissue preparation comprising obtaining a tissue preparation treated by paraffin embedding and then deparaffinization and contacting the tissue preparation with a composition according to claim 15.

17. The method according to claim 16, further comprising a step of determining that the tissue preparation is positive when GPR20 has been detected or measured in the tissue preparation, or the expression level of GPR20 in the tissue preparation is equivalent to or higher than a predetermined reference, and determining that the tissue preparation is negative when GPR20 has not been detected or measured in the tissue preparation, or the expression level of GPR20 in the tissue preparation is equivalent to or lower than a predetermined reference.

* * * * *